US009364532B2

(12) United States Patent
Stojdl

(10) Patent No.: US 9,364,532 B2
(45) Date of Patent: Jun. 14, 2016

(54) COMPOSITIONS AND METHODS FOR GLIOBLASTOMA TREATMENT

(75) Inventor: David F. Stojdl, Ottawa (CA)

(73) Assignee: CHILDREN'S HOSPITAL OF EASTERN ONTARIO RESEARCH INSTITUTE INC., Ottawa (CA)

( * ) Notice: Subject to any disclaimer, the term of this patent is extended or adjusted under 35 U.S.C. 154(b) by 0 days.

(21) Appl. No.: 14/123,057

(22) PCT Filed: Jun. 7, 2012

(86) PCT No.: PCT/CA2012/050385

§ 371 (c)(1), (2), (4) Date: Nov. 27, 2013

(87) PCT Pub. No.: WO2012/167382

PCT Pub. Date: Dec. 13, 2012

(65) Prior Publication Data

US 2014/0093527 A1 Apr. 3, 2014

Related U.S. Application Data

(60) Provisional application No. 61/494,628, filed on Jun. 8, 2011.

(51) Int. Cl.

*A61K 39/205* (2006.01)
*A61K 39/12* (2006.01)

(Continued)

(52) U.S. Cl.

CPC ............. *A61K 39/205* (2013.01); *A61K 35/766* (2013.01); *C07K 14/005* (2013.01); *C12N 7/00* (2013.01); *A61K 38/00* (2013.01);

(Continued)

(58) Field of Classification Search

None

See application file for complete search history.

(56) References Cited

U.S. PATENT DOCUMENTS 4,554,101 A 11/1985 Hopp
4,683,195 A 7/1987 Mullis et al.

(Continued)

FOREIGN PATENT DOCUMENTS

CA 2739963 A1 4/2010
EP 0320308 6/1989

(Continued)

OTHER PUBLICATIONS

Parato et al., "Recent Progress in the Battle Between Oncolytic Viruses and Tumours," Nature Reviews Cancer, vol. 5, 965-976 (2005).*

(Continued)

*Primary Examiner* — Benjamin P Blumel
*Assistant Examiner* — M. Franco Salvoza
(74) *Attorney, Agent, or Firm* — David Nauman; Borden Ladner Gervais LLP

(57) ABSTRACT

The present disclosure concerns an oncolytic virus for the treatment of cancer, such as in brain cancer, for example glioblastoma. The oncolytic virus may exhibit reduced levels of neurotoxicity. The oncolytic virus may be an isolated viral particle capable of producing a cDNA polynucleotide that includes a sequence according to SEQ ID NO: 1 when the virus is in a host cell. The oncolytic virus may be an isolated viral particle that includes an RNA polynucleotide that includes a sequence according to SEQ ID NO: 2. The oncolytic virus may be an isolated viral particle having a genome that includes open reading frames that encode: proteins having sequences comprising SEQ ID NOs: 3, 4, 5, 6 and 7; or variants thereof.

8 Claims, 16 Drawing Sheets

Farmington Virus:

-Rhabdovirus isolated from a healthy wild bird captured in Connecticut (R. Wallis 1969)

FMT 1 2 3 4 L
LNYV L
50% similarity

(51) Int. Cl.

| | |
|---|---|
| ***A61K 35/766*** | (2015.01) |
| ***C07K 14/005*** | (2006.01) |
| ***C12N 7/00*** | (2006.01) |
| *A61K 38/00* | (2006.01) |

(52) U.S. Cl.

CPC ................ *C12N2760/20021* (2013.01); *C12N 2760/20022* (2013.01); *C12N 2760/20032* (2013.01)

(56) References Cited

U.S. PATENT DOCUMENTS

| | | | |
|---|---|---|---|
| 4,683,202 | A | 7/1987 | Mullis |
| 4,684,611 | A | 8/1987 | Schilperoort et al. |
| 4,800,159 | A | 1/1989 | Mullis et al. |
| 4,879,236 | A | 11/1989 | Smith et al. |
| 4,883,750 | A | 11/1989 | Whiteley et al. |
| 4,946,773 | A | 8/1990 | Maniatis et al. |
| 4,952,500 | A | 8/1990 | Finnerty et al. |
| 5,220,007 | A | 6/1993 | Pederson et al. |
| 5,279,721 | A | 1/1994 | Schmid |
| 5,284,760 | A | 2/1994 | Feinstone et al. |
| 5,302,523 | A | 4/1994 | Coffee et al. |
| 5,322,783 | A | 6/1994 | Tomes et al. |
| 5,354,670 | A | 10/1994 | Nickoloff et al. |
| 5,366,878 | A | 11/1994 | Pederson et al. |
| 5,384,253 | A | 1/1995 | Krzyzek et al. |
| 5,389,514 | A | 2/1995 | Taylor |
| 5,399,363 | A | 3/1995 | Liversidge et al. |
| 5,464,765 | A | 11/1995 | Coffee et al. |
| 5,466,468 | A | 11/1995 | Schneider et al. |
| 5,538,877 | A | 7/1996 | Lundquist et al. |
| 5,538,880 | A | 7/1996 | Lundquist et al. |
| 5,543,158 | A | 8/1996 | Gref et al. |
| 5,550,318 | A | 8/1996 | Adams et al. |
| 5,563,055 | A | 10/1996 | Townsend et al. |
| 5,580,859 | A | 12/1996 | Felgner et al. |
| 5,589,466 | A | 12/1996 | Felgner et al. |
| 5,591,616 | A | 1/1997 | Hiei et al. |
| 5,610,042 | A | 3/1997 | Chang et al. |
| 5,635,377 | A | 6/1997 | Pederson et al. |
| 5,641,515 | A | 6/1997 | Ramtoola et al. |
| 5,656,610 | A | 8/1997 | Shuler et al. |
| 5,702,932 | A | 12/1997 | Hoy et al. |
| 5,736,524 | A | 4/1998 | Content et al. |
| 5,739,169 | A | 4/1998 | Ocain et al. |
| 5,780,448 | A | 7/1998 | Davis |
| 5,789,166 | A | 8/1998 | Bauer et al. |
| 5,789,215 | A | 8/1998 | Berns et al. |
| 5,798,208 | A | 8/1998 | Crea |
| 5,801,005 | A | 9/1998 | Cheever et al. |
| 5,824,311 | A | 10/1998 | Greene et al. |
| 5,830,650 | A | 11/1998 | Crea |
| 5,830,880 | A | 11/1998 | Sedlacek et al. |
| 5,840,873 | A | 11/1998 | Nelson et al. |
| 5,843,640 | A | 12/1998 | Patterson et al. |
| 5,843,650 | A | 12/1998 | Segev |
| 5,843,651 | A | 12/1998 | Stimpson et al. |
| 5,843,663 | A | 12/1998 | Stanley et al. |
| 5,846,225 | A | 12/1998 | Rosengart et al. |
| 5,846,233 | A | 12/1998 | Lilley et al. |
| 5,846,708 | A | 12/1998 | Hollis et al. |
| 5,846,709 | A | 12/1998 | Segev |
| 5,846,717 | A | 12/1998 | Brow et al. |
| 5,846,726 | A | 12/1998 | Nadeau et al. |
| 5,846,729 | A | 12/1998 | Wu et al. |
| 5,846,783 | A | 12/1998 | Wu et al. |
| 5,846,945 | A | 12/1998 | McCormick |
| 5,849,481 | A | 12/1998 | Urdea et al. |
| 5,849,483 | A | 12/1998 | Shuber et al. |
| 5,849,486 | A | 12/1998 | Heller et al. |
| 5,849,487 | A | 12/1998 | Hase et al. |
| 5,849,497 | A | 12/1998 | Steinman |
| 5,849,546 | A | 12/1998 | Sousa et al. |
| 5,849,547 | A | 12/1998 | Cleuziat et al. |
| 5,851,770 | A | 12/1998 | Babon et al. |
| 5,851,772 | A | 12/1998 | Mirzabekov et al. |
| 5,853,990 | A | 12/1998 | Winger et al. |
| 5,853,992 | A | 12/1998 | Glazer et al. |
| 5,853,993 | A | 12/1998 | Dellinger et al. |
| 5,856,092 | A | 1/1999 | Dale et al. |
| 5,858,652 | A | 1/1999 | Laffler et al. |
| 5,861,244 | A | 1/1999 | Wang et al. |
| 5,863,732 | A | 1/1999 | Richards |
| 5,863,753 | A | 1/1999 | Haugland et al. |
| 5,866,331 | A | 2/1999 | Singer et al. |
| 5,866,337 | A | 2/1999 | Schon |
| 5,866,366 | A | 2/1999 | Kallender |
| 5,871,986 | A | 2/1999 | Boyce |
| 5,882,864 | A | 3/1999 | An et al. |
| 5,900,481 | A | 5/1999 | Lough et al. |
| 5,905,024 | A | 5/1999 | Mirzabekov et al. |
| 5,910,407 | A | 6/1999 | Vogelstein et al. |
| 5,912,124 | A | 6/1999 | Kumar |
| 5,912,145 | A | 6/1999 | Stanley |
| 5,912,148 | A | 6/1999 | Eggerding |
| 5,916,776 | A | 6/1999 | Kumar |
| 5,916,779 | A | 6/1999 | Pearson et al. |
| 5,919,626 | A | 7/1999 | Shi et al. |
| 5,919,630 | A | 7/1999 | Nadeau et al. |
| 5,922,574 | A | 7/1999 | Minter |
| 5,925,517 | A | 7/1999 | Tyagi et al. |
| 5,925,525 | A | 7/1999 | Fodor et al. |
| 5,925,565 | A | 7/1999 | Berlioz et al. |
| 5,928,862 | A | 7/1999 | Morrison |
| 5,928,869 | A | 7/1999 | Nadeau et al. |
| 5,928,870 | A | 7/1999 | Lapidus et al. |
| 5,928,905 | A | 7/1999 | Stemmer et al. |
| 5,928,906 | A | 7/1999 | Koster et al. |
| 5,929,227 | A | 7/1999 | Glazer et al. |
| 5,932,413 | A | 8/1999 | Celebuski |
| 5,932,451 | A | 8/1999 | Wang et al. |
| 5,935,791 | A | 8/1999 | Nadeau et al. |
| 5,935,819 | A | 8/1999 | Eichner et al. |
| 5,935,825 | A | 8/1999 | Nishimura et al. |
| 5,939,291 | A | 8/1999 | Loewy et al. |
| 5,942,391 | A | 8/1999 | Zhang et al. |
| 5,945,100 | A | 8/1999 | Fick |
| 5,981,274 | A | 11/1999 | Tyrrell et al. |
| 5,994,624 | A | 11/1999 | Trolinder et al. |

FOREIGN PATENT DOCUMENTS

| | | |
|---|---|---|
| EP | 0329822 | 8/1989 |
| GB | 2202328 | 9/1988 |
| JP | 2004-525855 T | 8/2004 |
| WO | 87/06270 | 10/1987 |
| WO | 88/10315 | 12/1988 |
| WO | 89/06700 | 7/1989 |
| WO | 89/09284 | 10/1989 |
| WO | 91/09944 | 7/1991 |
| WO | 95/06128 | 3/1995 |
| WO | 01/19380 A2 | 3/2001 |
| WO | 2009/016433 A2 | 2/2009 |

OTHER PUBLICATIONS

Rudikoff et al.,"Single amino acid substitution altering antigen-binding specificity," Proc Natl Acad Sci USA 79:1979-1983 (1982).*

Pearson, "Silent Mutations Speak Up," Nature (Dec. 2006).*

Kaufman et al., "Oncolytic viruses: a new class of immunotherapy drugs," Nature Review Drug Discovery 14(9): 642-64 (2015).*

Heiber, "Characterization and Development of Vesicular Stomatitis Virus for Use as an Oncolytic Vector," Open Access Dissertations, Paper 600 (2011).*

Ferguson et al., "Systemic Delivery of Oncolytic Viruses: Hopes and Hurdles," Advances in Virology, Hindawi Publishing Corporation (2012).*

Ikeda et al., "Oncolytic virus therapy of multiple tumors in the brain requires suppression of innate and elicited antiviral responses," Nature Medicine vol. 5, No. 8 (1999).*

Stylli et al., "Mouse models of glioma," Journal of Clinical Neuroscience, 22: 619-626 (2015).*

(56) References Cited

OTHER PUBLICATIONS

Palacios et al., "Characterization of Farmington virus, a novel virus from birds that is distantly related to members of the family Rhabdoviridae," Virology Journal 10: 219 (2013).*
Palacios et al., "Farmington virus, complete genome", Genbank Accession #HM627182.
Written Opinion and Search Report for corresponding International Application No. PCT/CA2012/050385 dated Aug. 24, 2012.
Written Opinion and Search Report for corresponding International Application No. PCT/CA2012/050893 dated Aug. 28, 2013.
Beyer, R.J. et al. "Oncoretrovirus and Lentivirus Vectors Pseudotyped with Lymphocytic Choriomeningitis Virus Glycoprotein: Generation, Concentration, and Broad Host Range" Journal of Virology. 2002. vol. 76, No. 3, pp. 1488-1495.
Watson, D.J. et al. "Targeted Transduction Patterns in the Mouse Brain by Lentivirus Vectors Pseudotyped with VSV, Ebola, Mokola, LCMV, or MuLVEnvelope Proteins" Molecular Therapy. 2002. vol. 5, No. 5, pp. 528-537.
Brun, J. et al. "Identification of Genetically Modified Maraba Virus as an Oncolytic Rhabdovirus" Molecular Therapy. 2010. vol. 18, No. 8, pp. 1440-1449.
Written Opinion and Search Report for corresponding International Application No. PCT/IB2010/003396 dated Jul. 12, 2011.
Brun et al., "Identification of Genetically Modified Maraba Virus as an Oncolytic Rhabdovirus", Molecular Therapy, published online Jun. 15, 2010, vol. 18, No. 8, pp. 1440-1449.
Sanjuan et al., The contribution of epistasis to the architecture of fitness in an RNA virus, Proceedings of the National Academy of Science, Oct. 26, 2004, vol. 101, No. 43, pp. 15376-15379.
Almendro et al., "Cloning of the Human Platelet Endothelial Cell Adhesion Molecule-1 Promoter and its Tissue-Specific Expression", The Journal of Immunology, 157(12), Dec. 1996, pp. 5411-5421.
Altomonte et al., "Enhanced oncolytic potency of vesicular stomatitis virus through vector-mediated inhibition of NK and NKT cells", Cancer Gene Therapy, 2009, published online Oct. 10, 2008, vol. 16, pp. 266-278.
Abschuetz et al., "Oncolytic murine autonomous parvovirus, a candidate vector for glioma gene therapy, is innocuous to normal and immunocompetent mouse glial cells", Cell Tissue Res. published online May 3, 2006, vol. 325, pp. 423-426.
Angel et al., "Phorbol Ester-Inducible Genes Contain a Common Cis Element Recognized by a TPA-Modulated Trans-Action Factor", Cell, vol. 49, Jun. 19, 1987, pp. 729-739.
Angel et al., "12-0-Tetradecanoyl-Phorbol-13-Acetate Induction of the Human Collagenase Gene is Mediated by an Inducible Enhancer Element Located in the 5'-Flanking Region", Molecular and Cellular Biology, Jun. 1987, vol. 7, No. 6, pp. 2256-2266.
Austin-Ward et al., "Gene Therapy and its applications", Rev. Med. Chile, vol. 126, No. 7, Jul. 1998, pp. 838-845.
Bakhshi et al., "Cloning the Chromosomal Breakpoint of t(14;18) Human Lymphomas: Clustering around Jh on Chromosome 14 and near a Transcriptional Unit on 18", Cell, vol. 41, Jul. 1985, pp. 899-906.
Banerji et al., "Expression of a beta-Globin Gene is Enhanced by Remote SV40 DNA Sequences", Cell., vol. 27, Dec. 1981, Part 1, pp. 299-308.
Banerji et al., "A Lymphocyte-Specific Cellular Enhancer is Located Downstream of the Joining Region in Immunoglobulin Heavy Chain Genes", Cell., vol. 33, Jul. 1983, pp. 729-740.
Bermann et al., "A Genetically Engineered Influenza A Virus with ras-Dependent Oncolytic Properties", Cancer Research, 2001, vol. 61, pp. 8188-8193.
Berkhout et al., "Tat Trans-Activates the Human Immunodeficiency Virus through a Nascent RNA Target", Cell., vol. 59, Oct. 20, 1989, pp. 273-282.
Blanar et al., "A gamma-interferon-induced factor that binds the interferon response sequence of the MHC class I gene, H-2Kb", The EMBO Journal, vol. 8, No. 4, Apr. 1989, pp. 1139-1144.
Bodine et al., "An enhancer element lies 3' to the human A gamma globin gene", The EMBO Journal. vol. 6, No. 10, Oct. 1987, pp. 2997-3004.
Boshart et al., "A Very Strong Enhancer is Located Upstream of an Immediate Early Gene of Human Cytomegalovirus", Cell., vol. 41, Jun. 1985, pp. 521-530.
Bosze et al., "A transcriptional enhancer with specificity for erythroid cells is located in the long terminal repeat of the Friend murine leukemia virus", The EMBO Journal, vol. 5, No. 7, Jul. 1986, pp. 1615-1623.
Braddock et al., "HIV-1 TAT "Activates" Presynthesized RNA in the Nucleus", Cell, vol. 58, Jul. 28, 1989, pp. 269-279.
Braisted et al., "Minimizing a binding domain from protein A", Proc. Natl. Acad. Sci. USA, vol. 93, Jun. 1996, pp. 5688-5692.
Bukowski et al., "Signal transduction abnormalities in T lymphocytes from patients with advanced renal carcinoma: clinical relevant and effects of cytokine therapy", Clinical Cancer Research, vol. 4, No. 10, Oct. 1998, pp. 2337-2347.
Bulla et al., "The hepatitis B virus enhancer modulates transcription of the hepatitis B virus surface antigen gene from an internal location", Journal of Virology, vol. 4, Apr. 1988, p. 1437-1441.
Burton et al., "Human Antibodies from Combinatorial Libraries", Advances in Immunology, vol. 57, 1994, pp. 191-280.
Choi et al., "An Altered Pattern of Cross-Resistance in Multidrug-Resistant Human Cells Results from Spontaneous Mutations in the mdr1 (P-Glycoprotein) Gene," Cell, vol. 53, May 20, 1988, pp. 519-529.
Christodoulides et al., "Immunization with recombinant class I outermembrane protein from Neisseria meningitidis: influence of liposomes and adjuvants on antibody avidity, recognition of native protein and the induction of a bactericidal immune response against meningococci", Microbiology, vol. 144, No. 11, Nov. 1998, pp. 3027-3037.
Cleary et al., "Nucleotide sequence of a t(14;18) chromosomal breakpoint in follicular lymphoma and demonstration of a breakpoint-cluster region near a transcriptionally active locus of chromosome 18", Proc. Natl. Acad. Sci., USA, vol. 82, Nov. 1985, pp. 7439-7443.
Cleary et al., "Detection of a Second t(14;18) Breakpoint Cluster Region in Human Follicular Lymphomas", J. Exp. Med., vol. 164(1), Jul. 1986, pp. 315-320.
Cocea, "Duplication of a Region in the Multiple Cloning Site of a Plasmid Vector to Enhance Cloning-Mediated Addition of Restriction Sites to a DNA Fragment", Biotechniques, vol. 23(5), Nov. 1997, pp. 814-816.
Coffey et al., "Reovirus Therapy of Tumors with Activated Ras Pathway", Science, vol. 282, No. 5392, Nov. 13, 1998, pp. 1332-1334.
Cohen et al., "Serotonin Receptor Activation of Phosphoinositide Turnover in Uterine, Fundal, Vascular, and Tracheal Smooth Muscle", Journal of Cardiovascular Pharmacology, 1987, accepted for publication Nov. 7, 1986, vol. 10, pp. 176-181.
Connor et al., "Role of Residues 121 to 124 Vesicular Stomatitis Virus Matrix Protein in Virus Assembly and Virus-Host Interaction", Journal of Virology, Apr. 2006, vol. 80, No. 8, pp. 3701-3711.
Costa et al., "The cell-specific enhancer of the mouse transthyretin (prealbumin) gene binds a common factor at one site and a liver-specific factor(s) at two other sites", Molecular and Cellular Biology, Jan. 1988, vol. 8, No. 1, pp. 81-90.
Campbell et al., "Functional analysis of the individual enhancer core sequences of polyomavirus: cell-specific uncoupling of DNA replication from transcription", Molecular and Cellular Biology, May 1988, vol. 8, No. 5, pp. 1993-2004.
Campere et al., "Postnatal repression of the alpha-fetoprotein gene is enhancer independent", Genes & Development, vol. 3, 1989, revised version accepted for publication Feb. 15, 1989, pp. 537-546.
Campo et al., Transcriptional control signals in the genome of bovine papillomavirus type 1, Nature, vol. 303, May 1983, pp. 77-80.
Carbonelli et al., "A plasmid vector for isolation of strong promoters in *Escherichia coli*", FEMS Microbiology Letters, vol. 177, Aug. 1999, pp. 75-82.

(56) References Cited

OTHER PUBLICATIONS

Celander et al., "Glucocorticoid regulation of murine leukemia virus transcription elements is specified by determinants within the viral enhancer region", Journal of Virology, Feb. 1987, vol. 6, No. 2, pp. 269-275.
Celander et al., "Regulatory Elements with in the Murine Leukemia Virus Enhancer Regions Mediate Clucocorticoid Responsiveness", Journal of Virology, vol. 62, now. 4, Apr. 1988, pp. 1314-1322.
Chandler et al., "RNA splicing specificity determined by the coordinated action of RNA recognition motifs in SR proteins", Proc. Natl. Acad. Sci. USA, vol. 94, Apr. 1997, pp. 3596-3601.
Chaterjee et al., "Negative regulation of the thyroid-stimulating hormone alpha gene by thyroid hormone: Receptor interaction adjacent to the TATA box", Proc. Natl. Acad. Sci, USA, vol. 86, Dec. 1989, pp. 9114-9118.
Chen et al., "High-efficiency transformation of mammalian cells by plasmid DNA", Molecular and Cellular Biology, Aug. 1987, vol. 7, No. 8, pp. 2745-2752.
Cripe et al., "Transcriptional regulation of the human papillomavirus-16 E6-E7 promoter by a heratinocyte-dependent enhancer, and by viral E2 trans-activator and repressor gene products: implications for cervical carcinogenesis", The EMBO Journal, vol. 6, No. 12, Dec. 1, 1987, pp. 3745-3753.
Culotta et al., "Fine Mapping of a Mouse Metallothionein Gene Metal Response Element", Molecular and Cellular Biology, Mar. 1989, vol. 9, No. 3, pp. 1376-1380.
Culver et al., In Vivo Gene Transfer with Retroviral Vector-Producer Cells for Treatment of Experimental Brain Tumors, Science, vol. 256, No. 5063, Jun. 12, 1992, pp. 1550-1552.
Cunningham et al., "High-Resolution Epitope Mapping of hGH-Receptor Interactions by Alanine-Scanning Mutagenesis", Science, vol. 244, No. 4908, Jun. 2, 1989, pp. 1081-1085.
Cybinski et al., "Isolation of Tibrogargan Virus, A New Australian Rhabdovirus, from Culicoides Brevitarsis", Veterinary Microbiology, 1980, accepted for publication Jun. 26, 1980, vol. 5, pp. 301-308.
Dandolo et al., "Regulation of polyoma virus transcription in murine embryonal carcinoma cells", Journal of Virology, Jul. 1983, vol. 47, No. 1, pp. 55-64.
Davidson et al., "Intralesional Cytokine Therapy in Cancer: A Pilot Study of GM-CSF Infusion in Mesothelioma", Journal of Immunotherapy, 1998, accepted for publication May 5, 1997, vol. 21, No. 5, pp. 389-398.
Deschamps et al., "Indentification of a Transcriptional Enhancer Element Upstream from the Proto-Oncogene fos", Science, vol. 230, No. 4730, Dec. 6, 1985, pp. 1174-1177.
de Villiers et al., "Polyoma virus DNA replication requires an enhancer", Nature, vol. 312, No. 5991, Nov. 15, 1984, pp. 242-246.
Dhar et al., "Effect of Preexisting Immunity on Oncolytic Adenovirus Vector INGN 007 Antitumor Efficacy in Immunocompetent and Immunosuppressed Syrian Hamsters", Journal of Virology, Mar. 2009, vol. 83, No. 5, pp. 2130-2139.
Dilman, "Perceptions of Herceptin: A Monoclonal Antibody for the Treatment of Breast Cancer", Cancer Biotherapy & Radiopharmaceuticals, vol. 14, No. 1, Feb. 1999, pp. 5-10.
Doherty et al., "Isolation of Arboviruses from Mosquitoes, Biting Midges, Sandflies and Vertebrates Collected in Queensland, 1969 and 1970", Transactions of the Royal Society of Tropical Medicine and Hygiene, vol. 67, No. 4, 1973, pp. 536-543.
Edbrooke et al., "Identification of cis-Acting Sequences Responsible for Phorbol Ester Induction of Human Serum Amyloid A Gene Expression via a Nuclear Factor kB-Like Transcription Factor", Molecular and Cellular Biology, May, 1989, vol. 9, No. 5, pp. 1908-1916.
Edlund et al., "Cell-Specific Expression of the Rat Insulin Gene: Evidence for Role of Two Distinct 5' Flanking Elements", Science, vol. 230, No. 4728, Nov. 22, 1985, pp. 912-916.
Endo et al., "Virus-mediated oncolysis induces danger singal and stimulates cytotoxic T-lymphocyte activity via proteasome activator upregulation", Oncogene, 2008, published online Nov. 5, 2007, vol. 27, pp. 2375-2381.
Fechheimer et al., "Transfection of mammalian cells with plasmid DNA by scrape loading and sonication loading", Proc. Natl. Acad. Sci, USA, vol. 84, Dec. 1987, Cell Biology, pp. 8463-8467.
Feng et al., "HIV-1 tat trans-activation requires the loop sequence within tar," Nature, vol. 334, Jul. 14, 1988, pp. 165-167.
Ferran et al., "The Vesicular Stomatitis Virus Matrix Protein Inhibits Transcription from the Human Beta Interferon Promoter", Journal of Virology, Jan. 1997, vol. 71, pp. 371-377.
Firak et al., "Minimal Transcriptional Enhancer of Simian Virus 40 Us a 74-Base-Pair Sequence That Has Interacting Domains", Molecular and Cellular Biology, Nov. 1986, vol. 6, pp. 3667-3676.
Foecking et al, "Powerful and Versatile Enhancer-Promoter Unit for Mammalian Expression Vectors", Gene, vol. 45, 1986, issue 1, pp. 101-105.
Fuerst et al., "Eukaryotic transient-expression system based on recombinant vaccinia virus that synthesizes bacteriophage T7 RNA polymerase", Proc. Natl. Acad. Sco. USA, vol. 83, Nov. 1986, pp. 8122-8126.
Fujita et al., "Interferon-Beta Gene Regulation: Tandemly Repeated Sequences of a Synthetic 6 bp Oligomer Function as a Virus-Inducible Enhancer", Cell., vol. 49, May 8, 1987, pp. 357-369.
Gilles et al., "A Tissue-specific Transcription Enhancer Element is Located in the Major Intron of a Rearranged Immunoglobulin Heavy Chain Gene", Cell, vol. 33, Jul. 1983, pp. 717-728.
Gloss et al., "The upstream regulator region of the human papilloma virus-16 contains an E2 protein-independent enhancer which is specific for cervical carcinoma cells and regulated by glucocorticoid hormones", The EMBO Journal, vol. 6, Dec. 1, 1987, pp. 3735-3743.
Godbout et al., "Fine-Structure Mapping of the Three Mouse alpha-Fetoprotein Gene Enhancers", Molecular and Cellular Biology, Mar. 1988, vol. 8, No. 3, pp. 1169-1178.
Goodbourn et al., "Overlapping positive and negative regulatory domains of the human beta-interferon gene", Proc. Natl. Acad. Sci. USA, vol. 85, Mar. 1988, pp. 1447-1451.
Goodbourn et al., "The Human beta-Interferon Gene Enhancer is under Negative Control", Cell, vol. 45, May 23, 1986, pp. 601-610.
Gopal, "Gene Transfer Method for Transient Gene Expression, Stable Transformation, and Cotransformation of Suspension Cell Cultures", Molecular and Cellular Biology, May 1985, vol. 5, No. 5, pp. 1188-1190.
Graham et al., "A New Technique for the Assay of Infectivity of Human Adenovirus 5 DNA", Virology, vol. 52, 1973, accepted for publication Jan. 17, 1973, pp. 456-467.
Greene et al., "HIV-1, HTLV-1 and normal T-cell growth: transcriptional strategies and surprises", Immunology Today, vol. 10, No. 8, Aug. 1989, pp. 272-278.
Gromeier et al., "Intergeneric Poliovirus Recombinants for the Treatment of Malignant Glioma", PNAS, Jun. 6, 2000, vol. 97, No. 12, pp. 6803-6808.
Grosschedl et al., "Cell-Type Specificity of Immunoglobulin Gene Expression is Regulated by at Least Three DNA Sequence Elements", Cell., vol. 41, Jul. 1985, pp. 885-897.
Grote et al., "Live attenuated measles virus induces regression of human lymphoma xenografts in immunodeficient mice", Blood, vol. 97, No. 12, Jun. 15, 2001, pp. 3746-3754.
Hanibuchi et al., "Therapeutic Efficacy of Mouse-Human Chimeric Anti-Ganglioside GM2 Monoclonal Antibody Against Multiple Organ Micrometastases of Human Lung Cancer in NK Cell-Depleted SCID Mice", Int. J. Cancer, vol. 78, 1998, pp. 480-485.
Harland et al., "Translation of mRNA Injected into Xenopus Oocytes is Specifically Inhibited by Antisense RNA", The Journal of Cell Biology, vol. 101, Sep. 1985, pp. 1094-1099.
Haslinger et al., "Upstream promoter element of the human metallothionein-IIA gene can act like an enhancer element", Proc. Natl. Acad. Sci. USA, vol. 82, Dec. 1985, pp. 8572-8576.
Hauber et al., "Mutational Analysis of the trans-Activation-Responsive Region of the Human Immunodeficiency Virus Type I Long Terminal Repeat", Journal of Virology, Mar. 1988, vol. 62, No. 3, pp. 673-679.
Heise et al., "An adenovirus E1A mutant that demonstrates potent and selective systemic anti-tumoral efficacy", Nature Medicine, vol. 6, No. 10, Oct. 2000, pp. 1134-1139.

(56) References Cited

OTHER PUBLICATIONS

Hellstrand et al, "Histamine and Cytokine Therpay", Acta Oncologica, vol. 37, No. 4, 1998, pp. 347-353.
Hen et al. , "A mutated polyoma virus enhancer which is active in undifferentiated embryonal carcinoma cells is not repressed by adenovirus-2 E1A products", Nature, vol. 321, May 1986, pp. 249-251.
Herr et al., "The SV40 Enhancer is Composed of Multiple Functional Elements That Can Compensate for One Another", Cell, vol. 45, May 9, 1986, pp. 461-470.
Hilton et al., "Saturation Mutagenesis of the WSxWS Motif of the Erythropoietin Receptor", The Journal of Biological Chemistry, vol. 271, No. 9, Mar. 1, 1996, pp. 4699-4708.
Hirochika et al., "Enhancers and trans-Acting E2 Transcriptional Factors of Papillomaviruses", Journal of Virology, vol. 61, No. 8, Aug. 1987, pp. 2599-2606.
Hirsch et al., "Identification of Positive and Negative Regulatory Elements Governing Cell-Type-Specific Expression of the Neural Cell Adhesion Molecule Gene", Molecular and Cellular Biology, vol. 10, No. 5, May 1990, pp. 1959-1968.
Holbrook et al, "cis-Acting Transcriptional Regulatory Sequences in the Gibbon Ape Leukemia Virus (GALV) Long Terminal Repeat", Virology, vol. 157, Mar. 1987, Issue 1, pp. 211-219.
Holden et al., "The molecular structure of insecticyanin from the tobacco hornworm *Manduca sexta* L. at 2.6 A resolution", The EMBO Journal, vol. 6, No. 6, 1987, pp. 1565-1570.
Horlick et al., "The Upstream Muscle-Specific Enhancer of the Rat Muscle Creatine Kinase Gene is Composed of Multiple Elements" Molecular and Cellular Biology, Jun. 1989, vol. 9, No. 6, pp. 2396-2413.
Huang et al., "Glucocorticoid Regulation of the Ha-MuSV p21 Gene Conferred by Sequences from Mouse Mammary Tumor Virus", Cell., vol. 27, Dec. 1981, Part 1, pp. 245-255.
Hug et al., "Organization of the Murine Mx Gene and Characterization of its Interferon-and Virus-Inducible Promoter", Molecular and Cellular Biology, Aug. 1988, vol. 8, No. 8, pp. 3065-3079.
Hui et al., "Pathways for Potentiation of Immunogenicity during Adjuvant-Assisted Immunizations with Plasmodium falciparum Major Merozoite Surface Protein 1", Infection and Immunity, Nov. 1998, vol. 66, No. 11, pp. 5329-5536.
Hwang et al., "Characterization of the S-Phase-Specific Transcription Regulatory Elements in a DNA Replication-Independent Testis-Specific H2B (TH2B) Histone Gene", Molecular and Cellular Biology, vol. 10, No. 2, Feb. 1990, pp. 585-592.
Imagawa et al., "Transcription Factor AP-2 Mediates Induction by Two Different Signal-Transduction Pathways" Protein Kinase C and cAMP, Cell., vol. 51, Oct. 23, 1987, pp. 251-260.
Imbra et al., "Phorbol ester induces the transcriptional stimulatory activity of the SV40 enhancer", Nature, vol. 323, Oct. 9, 1986, pp. 555-558.
Imler et al., "Negative Regulation Contributes to Tissue Specificity of the Immunoglobulin Heavy-Chain Enhancer", Molecular and Cellular Biology, Jul. 1987, vol. 7, No. 7, pp. 2558-2567.
Imperiale et al., "Adenovirus 5 E2 Transcription Unit: an E1A-Inducible Promoter with an Essential Element That Functions Independently of Position or Orientation", Molecular and Cellular Biology, vol. 4, No. 5, May 1984, pp. 875-882.
Innis et al, "DNA sequencing with Thermus aquaticus DNA polymerase and direct sequencing of polymerase chain reaction-amplified DNA", Proc. Natl. Acad. Sci. USA, vol. 85, Dec. 1988, pp. 9436-9440.
Inouye et al., "Up-promoter mutations in the Ipp gene of *Escherichia coli*", Nucleic Acids Research, vol. 13, No. 9, received Mar. 4, 1985, accepted Apr. 5, 1985, pp. 3101-3109.
Irie et al., "Regression of cutaneous metastatic melanoma by intralesional injection with human monoclonal antibody to ganglioside GD2", Proc. Natl. Acad. Sci. USA, vol. 83, Nov. 1986, pp. 8694-8698.
Jakobovits et al., "A Discrete Element 3' of Human Immunodeficiency Virus 1 (HIV-1) and HIV-2 mRNA Initiation Sites Mediates Transcriptional Activation by an HIV trans Activator", Molecular and Cellular Biology, Jun. 1988, vol. 8, No. 6, pp. 2555-2561.
Jameel et al., "The Human Hepatitis B Virus Enhancer Requires trans-Acting Cellular Factor(s) for Activity", Molecular and Cellular Biology. Feb. 1986, vol. 6, No. 2, pp. 710-715.
Jaynes et al., "The Muscle Creatine Kinase Gene is Regulated by Multiple Upstream Elements, Including a Muscle-Specific Enhancer", Molecular and Cellular Biology, Jan. 1988, vol. 8, No. 1, pp. 62-70.
Johnson et al., "Protein kinase inhibitor prevents pulmonary edema in response to H2O2", American Journal of Physiology, vol. 256, 1989, pp. H1012-1022.
Ju et al., "Interleukin-18 gene transfer increases antitumor effects of suicide gene therapy through efficient induction of antitumor immunity", Gene Therapy, 2000, vol. 7, pp. 1672-1679.
Kadesch et al., "Effects of the Position of the Simian Virus 40 Enhancer on Expression of Multiple Transcription Units in a Single Plasmid", Molecular and Cellular Biology, Jul. 1986, vol. 6, No. 7, pp. 2593-2601.
Kaeppler et al., Silicon carbide fiber-mediated DNA delivery into plant cells, Plant Cell Reports, 1990, vol. 9, pp. 415-418.
Kaneda et al., "Increased Expression of DNA Cointroduced with Nuclear Protein in Adult Rat Liver", Science, vol. 243, No. 4889, Jan. 20, 1989, pp. 375-378.
Karin et al., Metal-Responsive Elements Act as Positive Modulators of Human Metallothionein-IIa Enhancer Activity, Molecular and Cellular Biology, Feb. 1987, vol. 7. No. 2, pp. 606-613.
Katinka et al., "Expression of Polyoma Early Functions in Mouse Embryonal Carcinoma Cells Depends on Sequence Rearrangements in the Beginning of the Late Region", Cell, vol. 20, Jun. 1980, pp. 393-399.
Katinka et al., "Polyoma DNA sequences involved in control of viral gene expression in murine embryonal carcinoma cells", Nature, vol. 290, Apr. 1981, pp. 720-722.
Kato et al., "Expression of Hepatitis B Virus Surface Antigen in Adult Rat Liver", The Journal of Biological Chemistry, vol. 266, No. 6, Feb. 25, 1991, pp. 3361-3364.
Kawamoto et al., "Identification of the Human Beta-Actin Enhancer and its Binding Factor", Molecular and Cellular Biology, Jan. 1988, vol. 8, No. 1, pp. 267-272.
Kerr et al., "Apoptosis: A Basic biological Phenomenon with Wide-Ranging Implications in Tissue Kinetics", Br. J. Cancer, received for publication Apr. 1972, published 1972, vol. 26, pp. 239-257.
Kerschner et al., "Identification and Characterization of Bahia Grande, Reed Ranch and Muir Springs Viruses, Related Members of the Family Rhabdoviridae with Widespread Distribution in the United States", J. Gen. Virology, Jun. 1986,, vol. 67, No. 6, pp. 1081-1089.
Kiledjian et al., "Identification and Characterization of Two Functional Domains within the Murine Heavy-Chain Enhancer", Molecular and Cellular Biology, Jan. 1988, vol. 8, No. 1, pp. 145-152.
Kinoh et al., "Generation of a recombinant Sendai virus that is selectively activated and lyses human tumor cells expressing matrix metalloproteinases", Gene Therapy, 2004, published online Apr. 15, 2004, vol. 11, pp. 1137-1145.
Klamut et al., "Molecular and Functional Analysis of the Muscle-Specific Promoter Region of the Duchenne Muscular Dystrophy Gene", Molecular and Cellular Biology, Jan. 1990, vol. 10, No. 1, pp. 193-205.
Koch et al., "Anatomy of a New B-Cell-Specific Enhancer", Molecular and Cellular Biology, Jan. 1989, vol. 9, No. 1, pp. 303-311.
Kraus et al., "Alternative promoter usage and tissue specific expression of the mouse somatostatin receptor 2 gene", FEBS Letters 428, May 29, 1998, Issue 3, pp. 165-170.
Kriegler et al., "Enhanced Transformation by a Simian Virus 40 Recombinant Virus Containing a Harvey Murine Sarcoma Virus Long Terminal Repeat", Molecular and Cellular Biology, Mar. 1983, vol. 3, No. 3, pp. 325-339.
Kriegler et al., "Transformation Mediated by the SV40 T Antigens: Separation of the Overlapping SV40 Early Genes with a Retroviral Vector", Cell., vol. 38, Sep. 1984, pp. 483-491.

(56) References Cited

OTHER PUBLICATIONS

Kriegler et al., "A Novel Form of TNF/Cachectin is a Cell Surface Cytotoxic Transmembrane Protein: Ramifications for the Complex Physiology of TNF", Cell., vol. 53, Apr. 8, 1988, pp. 45-53.
Kuhl et al., "Reversible Silencing of Enhancers by Sequences Derived from the Human IFN-alpha Promoter", Cell., vol. 50, Sep. 25, 1987, pp. 1057-1069.
Kunz et al., "Identifications of the promoter sequences involved in the interleukin-6 dependent expression of the rat alpha2-macroglobulin gene", Nucleic Acids Research, vol. 17, No. 3, 1989, accepted for publication Jan. 13, 1989, pp. 1121-1138.
Kwoh et al., "Transcription-based amplification system and detection of amplified human immunodeficiency virus type 1 with a bead-based sandwich hybridization format", Proc. natl. Acad. Sci. USA, vol. 86, Feb. 1989, pp. 1173-1177.
Kyte et al., "A Simple Method for Displaying the Hydropathic Character of a Protein", Journal Molecular Biology, 1982, vol. 157, pp. 105-132.
Lareyre et al., "A 5-Kilbase pair Promoter Fragment of the Murine Epididymal Retinoic Acid-binding Protein Gene Drives the Tissue-specific, Cell-specific, and Androgen-regulated Expression of a Foreign Gene in the Epididymis of Transgenic Mice", The Journal of Biological Chemistry, vol. 274, No. 12, Mar. 19, 1999, pp. 8282-8290.
Larsen et al., "Repression mediates cell-type-specific expression of the rat growth hormone gene", Proc. Natl. Acad. Sci, USA, vol. 83, Nov. 1986, pp. 8283-8287.
Laspia et al., "HIV-1 Tat Protein Increases Transcriptional Initiation and Stabilizes Elongation", Cell., vol. 59, Oct. 20, 1989, pp. 283-292.
Latimer et al., "Highly Conserved Upstream Regions of the alpha1-Antitrypsin Gene in Two Mouse Species Govern Liver-Specific Expression by Different Mechanisms", Molecular and Cellular Biology, Feb. 1990, vol. 10, No. 2, pp. 760-769.
Lawson et al., "Recombinant vesicular stomatitis viruses from DNA", Proc. Natl. Acad. Sci. USA, vol. 92, May 1995, pp. 4477-4481.
Lee et al., "The Highly Basic Ribosomal Protein L41 Interacts with the beta Subunit of Protein Kinase CKII and Stimulates Phosphorylation of DNA Topoisomerase IIalpha by CKII", Biochemical and Biophysical Research Communications, vol. 238, Received Jul. 29, 1997, published 1997, pp. 462-467.
Lee et al., "Glucocorticoids regulate expression of dihydrofolate reductase cDNA in mouse mammary tumour virus chimaeric plasmids", Nature, vol. 294, Nov. 19, 1981, pp. 228-232.
Lee et al., "Functional Analysis of the steroid hormone control region of mouse mammary tumour virus", Nucleic Acids Research, vol. 12, No. 10, accepted for publication Apr. 17, 1984, published 1984, pp. 4191-4206.
Levenson et al., "Internal Ribosomal Entry Site-Containing Retroviral Vectors with Green Fluorescent Protein and Drug Resistance Markers", Human Gene Therapy, May 20, 1998, vol. 9, pp. 1233-1236.
Levinson et al., "Activation of SV40 genome by 72-base pair tandem repeats of Moloney sarcoma virus", Nature, vol. 295, Feb. 18, 1982, pp. 568-572.
Logg et al., "A Uniquely Stable Replication-Competent Retrovirus Vector Achieves Efficient Gene Delivery in Vitro and in Solid Tumors", Human Gene Therapy, vol. 12, May 20, 2001, pp. 921-932.
Luria et al., "Promoter and enhancer elements in the rearranged alpha chain gene of the human T cell receptor", The EMBO Journal, Nov. 1987, vol. 6, No. 11, pp. 3307-3312.
Lusky et al., "Transient replication of bovine papilloma virus type 1 plasmids: cis and trans requirements", Proc. Natl. Acad. Sci. USA, Jun. 1986, vol. 83, pp. 3609-3613.
Lusky et al., "Bovine Papilloma Virus Contains an Activator of Gene Expression at the Distal End of the Early Transcription Unit", Molecular and Cellular Biology, Jun. 1983, vol. 3, No. 6, pp. 1108-1122.
Macejak et al., "Internal initiation of translation mediated by the 5' leader of a cellular mRNA", Letters to Nature, vol. 353, Sep. 5, 1991, pp. 90-94.
Majors et al., "A small region of the mouse mammary tumor virus long terminal repeat confers glucocorticoid hormone regulation on a linked heterologous gene", Proc. Natl. Acad. Sci, USA, vol. 80, Oct. 1983, pp. 5866-5870.
McNeall et al., "Hyperinducible gene expression from a metallothionein promoter containing additional metal-responsive elements", Gene, accepted for publication Nov. 3, 1988, published 1989, vol. 76, pp. 81-88.
Miksicek et al., "Glucocorticoid Responsiveness of the Transcriptional Enhancer of Moloney Murine Sarcoma Virus", Cell., Jul. 18, 1986, vol. 46. pp. 283-290.
Stephens et al., "The bovine papillomavirus genome and its uses as a eukaryotic vector", Biochem. J., 1987, vol. 248, pp. 1-11.
Stillman et al., "Replication and Amplification of Novel Vesicular Stomatitis Virus Minigenomes Encoding Viral Structural Proteins", Journal of Virology, May 1995, vol. 69, No. 5, pp. 2946-2953.
Stojdl et al., "VSV strains with defects in their ability to shutdown innate immunity are potent systemic anti-cancer agents", Cancer Cell, Oct. 2003, vol. 4, p. 263-275.
Stojdl et al., "Exploiting tumor-specific defects in the interferon pathway with a previously unknown oncolytic virus", Nature Medicine, vol. 6, No. 7, Jul. 2000, pp. 821-825.
Stuart et al., "Identification of multiple metal regulatory elements in mouse metallothionein-I promoter by assaying synthetic sequences", Nature, vol. 317, Oct. 31, 1985, pp. 828-831.
Sullivan et al., "Transcriptional Enhancers in the HLA-DQ Subregion", Molecular and Cellular Biology, Sep. 1987, vol. 7, No. 9, pp. 3315-3319.
Swartzendruber et al., "Neoplastic Differentiation: Interaction of Simian Virus 40 and Polyoma Virus with Murine Teratocarcinoma Cells in Vitro", J. Cell. Physio., 1975, vol. 85, pp. 179-188.
Takada et al., "A system for functional analysis of Ebola virus glycoprotein", Proc. Natl. Acad. Sci. USA, vol. 94, Dec. 1997, pp. 14764-14769.
Takebe et al., "Sr alpha Promoter: an Efficient and Versatile Mammalian cDNA Expression System Composed of the Simian Virus 40 Early Promoter and the R-U5 Segment of Human T-Cell Leukemia Virus Type 1 Long Terminal Repeat", Molecular and Cellular Biology, Jan. 1988, vol. 8, No. 1, pp. 466-472.
Tavernier et al., "Deletion mapping of the inducible promoter of human IFN-beta gene", Nature, vol. 301, Feb. 17, 1983, pp. 634-636.
Taylor et al., "Factor Substitution in a Human HSP70 Gene Promoter: TATA-Dependent and TATA-Independent Interactions", Molecular and Cellular Biology, Jan. 1990, vol. 10, No. 1, pp. 165-175.
Taylor et al., "E1a Transactivation of Human HSP70 Gene Promoter Substitution Mutants is Independent of the Composition of Upstream and TATA Elements", Molecular and Cellular Biology, Jan. 1990, vol. 10, No. 1, pp. 176-183.
Taylor et al., "Stimulation of the Human Heat Shock Protein 70 Promoter in Vitro by Simian Virus 40 Large T Antigen", The Journal of Biological Chemistry, Sep. 25, 1989, vol. 264, No. 27, pp. 16160-16164.
Terstegen et al., "The Vesicular Stomatitis Virus Matrix Protein Inhibits Glycoprotein 130-Dependent STAT Activation", Journal of Immunology, 2001, vol. 167, pp. 5209-5216.
Thiesen et al., "A DNA Element Responsible for the Different Tissue Specificities of Friend and Moloney Retroviral Enhancers", Journal of Virology, Feb. 1988, vol. 62, No. 2, pp. 614-618.
Travassos Da Rosa et al., "Two New Rhabdoviruses (Rhabdoviridae) Isolated from Birds During Surveillance for Arboviral Encephalitis, Northeastern United States", Emerging Infectious Diseases, vol. 8, No. 6, Jun. 2002, pp. 614-618.
Treisman, "Identification of a Protein-Binding Site That Mediates Transcriptional REsponse of the c-fos Gene to Serum Factors", Cell, vol. 46, Aug. 15, 1986, pp. 567-574.
Tronche et al., "The Rat Albumin Promoter: Cooperation with Upstream Elements is Required when Binding of APF/HNF1 to the Proximal Element is Partially Impaired by Mutation or Bacterial Methylation", Molecular and Cellular Biology, Nov. 1989, vol. 9, No. 11, pp. 4759-4766.

(56) References Cited

OTHER PUBLICATIONS

Trudel et al., "A 3' enhancer contributes to the stage-specific expression of the human beta-globin gene", Genes & Development, 1987, accepted for publication Sep. 4, 1987, vol. 1, pp. 954-961.
Tsujimoto et al., "Clustering of breakpoints on chromosome 11 in human B-cell neoplasms with the t(11 ; 14) chromosome translocation", Nature, vol. 315, May 23, 1985, pp. 340-343.
Tsujimoto et al., "Analysis of the structure, transcripts and protein products of bci-2, the gene involved in human follicular lymphoma", Proc. Natl. Acad. Sco. USA, vol. 83, Jul. 1986, pp. 5214-5218.
Tsumaki et al., "Modular Arrangement of Cartilage-and Neural Tissue-specific cis-Elements in the Mouse alpha 2(XI) Collagen Promoter", The Journal of Biological Chemistry, vol. 273, No. 36, Sep. 4, 1998, pp. 22861-22864.
Unno et al., "Oncolytic Viral Therapy for Cervical and Ovarian Cancer Cells by Sindbis Virus AR339 Strain", Clin Cancer Res., Jun. 15, 2005, vol. 11, No. 12, pp. 4553-4560.
Vanice et al., "Properties of the Human Hepatitis B Virus Enhancer: Position Effects and Cell-Type Nonspecificity", Journal of Virology, Apr. 1988, vol. 62, No. 4, pp. 1305-1313.
Vasseur et al., "Isolation and characterization of polyoma virus mutants able to develop in embryonal carcinoma cells", Proc. Natl. Acad. Sci. USA, vol. 77, No. 2, Feb. 1980, pp. 1068-1072.
Walker et al., "Strand displacement amplification—an isothermal, in vitro DNA amplification technique", Nucleic Acids Research, accepted for publication Mar. 10, 1992, published 1992, vol. 20, No. 7, pp. 1691-1696.
Wang et al., "SV40 Enhancer-Binding Factors are Required at the Establishment but Not the Maintenance Step of the Enhancer-Dependent Transcriptional Activation", Cell, vol. 47, Oct. 24, 1986, pp. 241-247.
Warren et al., "A Rapid Screen of Active Site Mutants in Glycinamide Ribonucleotide Transformylase", Biochemistry, Jul. 9, 1996, vol. 35, No. 27, pp. 8855-8862.
Weber et al., "An SV40 "Enhancer Trap" Incorporated Exogenous Enhancers or Generates Enhancers from its Own Sequences", cell., vol. 36, Apr. 1984, pp. 983-992.
Weinberger et al., "Localization of a Repressive Sequence Contributing to B-Cell Specificity in the Immunoglobulin Heavy-Chain Enhancer", Molecular and Cellular Biology, Feb. 1988, vol. 8, No. 2, pp. 988-992.
Wells et al., "Selectivity and antagonism of chemokine receptors", Journal of Leukocyte Biology, vol. 59, Jan. 1996, pp. 53-60.
Whelan et al., "Efficient recovery of infectious vesicular stomatitis virus entirely from cDNA clones", Proc. Natl. Acad. Sci, USA, vol. 92, Aug. 1995, pp. 8388-8392.
Winoto et al., "alpha beta Lineage-Specific Expression of a the alpha T Cell Receptor Gene by Nearby Silencers", Cell, vol. ss59, Nov. 17, 1989, pp. 649-655.
Wong et al., "Appearance of beta-lactamase activity in animal cells upon liposome-mediated gene transfer", Gene, vol. 10, accepted for publication Dec. 20, 1979, published 1980, pp. 87-94.
Wu et al., "CCR5 Levels and Expression Pattern Correlate with Infectability by Macrophage-tropic HIV-1, In Vitro", J. Exp. Med, vol. 185, No. 9, May 5, 1997, pp. 1681-1691.
Yelton et al., "Affinity Maturation of the BR96 Anti-Carcinoma Antibody by Codon-Based Mutagenesis", Journal of Immunology, vol. 155, No. 4, 1995, pp. 1994-2004.
Yutzey et al., "An Internal Regulatory Element Controls Troponin I Gene Expression", Molecular and Cellular Biology, Apr. 1989, vol. 9, No. 4, pp. 1397-1405.
Zheng et al., "ATP-Binding Site of Human Brain Hexokinase as Studied by Molecular Modeling and Site-Directed Mutagenesis", Biochemistry, submitted for publication Aug. 6, 1996, published 1996, vol. 35, pp. 13157-13164.
Zhao-Emonet et al., "Deletional and mutational analysis of the human CD4 gene promoter: characterization of a minimal tissue-specific promoter", Biochimica et Biophysica Acta, vol. 1442, accepted for publication Jul. 28, 1998, published 1998, pp. 109-119.
Sawyer et al., "Carboxyl-carboxylate interactions in proteins", Nature, vol. 295, Jan. 7, 1982, pp. 79-80.
Chang et al., "Glucose-Regulated Protein (GRP94 and GRP78) Genes Share Common Regulatory Domains and are Coordinately Regulated by Common trans-Acting Factors", Molecular and Cellular Biology, May 1989, vol. 9, No. 5, pp. 2153-2162.
Mouras et al., "Localization by in situ hybridization of a low copy chimaeric resistance gene introduced into plants by direct gene transfer", Mol. Gen. Genet., 1987, vol. 207, pp. 204-209.
Travassos Da Rosa et al., "Carajas and Maraba Viruses, Two New Vesiculoviruses Isolated from Phlebotomine Sand Flies in Brazil", American Journal Trop. Med. Hyg., vol. 33, No. 5, 1984, accepted for publication Mar. 2, 1984, pp. 999-1006.
Lin et al., "Chromosome localization of two human serine protease genes to region 14q11.2-q12 by in situ hybridization", Cytogenet. Cell Genet., vol. 53. 1990. pp. 169-171.
Bajorin et al., "Comparison of Criteria for Assigning Germ Cell Tumor Patients to "Good Risk" and "Poor Risk" Studies", Journal of Clinical Oncology, vol. 6, No. 5, May 1988, pp. 786-792.
Morton et al., "Technical Details of Intraoperative Lymphatic Mapping for Early Stage Melanoma", Arch. Surg. vol. 127, Apr. 1992, pp. 392-399.
Chiocca, "The host response to cancer virotherapy", Current Opinion in Molecular Therapeutics, Feb. 2008, vol. 10, No. 1, pp. 38-45.
Tronche et al., "Anatomy of the Rat Albumin Promoter", Molecular Biology Med., received for publication Jul. 12, 1989, published 1990, vol. 7, pp. 173-185.
Hensel et al., "PMA-Responsive 5' Flanking Sequences of the Human tNF Gene", Lymphokine Reearch, vol. 8, No. 3, 1989, pp. 347-351.
Frohman et al., "Rapid production of full-length cDNAs from rare transcripts: Amplification using a single gene-specific oligonucleotide primer", Proc. Natl. Acad. Sci, USA, vol. 85, Dec. 1988, pp. 8998-9002.
Mineta et al., "Attenuated multi-mutated herpes simplex virus-1 for the treatment of malignant gliomas", Nature Medicine, vol. 1, No. 9, Sep. 1995,pp. 938-943.
Mitchell et al., "Active Specific Immunotherapy of Melanoma With Allogeneic Cell Lysates", NY Acad. Sci., 1993, vol. 690, pp. 153-166.
Mordacq et al., "Co-localization of elements required for phorbol ester stimulation and glucocorticoid repression of proliferin gene expression", Genes & Development, accepted for publication Apr. 7, 1989, published 1989, vol. 3, pp. 760-769.
Moreau et al., "The SV40 72 base repair repeat has a striking effect on gene expression both in SV40 and other chimeric recombinants", Nucleic Acids Research, vol. 9, No. 22, 1981, received for publication Oct. 16, 1981, published 1981, pp. 6047-6088.
Muesing et al., "Regulation of mRNA Accumulation by a Human Immunodeficiency Virus Trans-Activator Protein", Cell., vol. 48, Feb. 27, 1987, pp. 691-701.
Nakaya et al., "Recombinant Newcastle Disease Virus as a Vaccine Vector", Journal of Virology, Dec. 2001, vol. 75, No. 23, pp. 11868-11873.
Ng et al., "Regulation of the human beta-actin promoter by upstream and intron domains", Nucleic Acids Research, vol. 17., No. 2, 1989, accepted for publication Dec. 20, 1988, pp. 601-615.
Nicolau et al., "Liposome-Mediated DNA Transfer in Eukaryotic Cells, Dependence of the transfer Efficiency Upon the Type of Liposomes Used and the Host Cell Cycle Stage", Biochimica et Biophysica Acta, vol. 721, Received for publication Mar. 31, 1982, published 1982, pp. 185-190.
Nicolau et al., "Liposomes as Carriers for in Vivo Gene Transfer and Expression", Methods in Enzymology, vol. 149, 1987, pp. 157-176.
Nomoto et al., "Cloning and Characterization of the alternative promoter regions of the human LIMK2 gene responsible for alternative transcripts with tissue-specific expression", Gene, vol. 236, accepted for publication Jun. 24, 1999, published 1999, pp. 259-271.
Ohara et al., "One-sided polymerase chain reaction: The amplification of cDNA", Proc. Natl. Acad. Sci. USA, Aug. 1989, vol. 86, pp. 5673-5677.

(56) References Cited

OTHER PUBLICATIONS

Omirulleh et al., "Activity of a chimeric promoter with the doubled CaMV 35S enhancer element in protoplast-derived cells and transgenic plants in maize", Plant Molecular Biology, vol. 21, accepted for publication Oct. 4, 1992, published 1993, pp. 415-428.
Ornitz et al., "Promoter and Enhancer Elements from the Rat Elastase I Gene Function Independently of Each Other and of Heterologous Enhancers", Molecular and Cellular Biology, Oct. 1987, vol. 7, No. 10, pp. 3466-3472.
Ondek et al., "Discrete elements within the SV40 enhancer region display different cell-specific enhancer activities", The EMBO Journal, Apr. 1987, vol. 6, No. 4, pp. 1017-1025.
Palmiter et al., "Differential Regulation of Metallothionein-Thymidine Kinase Fusion Genes in Transgenic Mice and Their Offspring", Cell., Jun. 1982, vol. 29, pp. 701-710.
Palmiter et al., "Dramatic Growth of Mice that Develop from Eggs Microinjected with Metallothionein-Growth Hormone Fusion Genes", Nature, Dec. 16, 1982, vol. 300, pp. 611-615.
Pech et al., "Functional Identification of Regulatory Elements within the Promoter Region of Platelet-Derived Growth Faction 2", Molecular and Cellular Biology, Feb. 1989, vol. 9, No. 2, pp. 396-405.
Pelletier et al., "Internal initiation of translation of eukaryotic mRNA directed by a sequence derived from poliovirus RNA", Nature, vol. 334, Jul. 28, 1988, pp. 320-325.
Perez-Stable et al., "Roles of Fetal G-gamma-Globin Promoter Elements and the Adult beta-Globin 3' Enhancer in the Stage-Specific Expresion of Globin Genes", Molecular and Cellular Biology, Mar. 1990, vol. 10, No. 3, pp. 1116-1125.
Picard et al., "A lymphocyte-specific enhancer in the mouse immunoglobulin k gene", Nature, Jan. 5, 1984, vol. 307, pp. 80-82.
Pietras et al., "Remission of human breast cancer xenografts on therapy with humanized monoclonal antibody to HER-2 receptor and DNA-reactive drugs", Oncogene, accepted for publication May 18, 1998, published 1998, pp. 2235-2249.
Pinkert et al., "An albumin enhancer located 10kb upstream functions along with its promoter to direct efficient, liver-specific expression in transgenic mice", Genes & Development, accepted for publication Mar. 4, 1987, vol. 1, published 1987, pp. 268-276.
Ponta et al., "Hormonal response region in the mouse mammary tumor virus along terminal repeat can be dissociated from the proviral promoter and has enhancer properties", Proc. Natl., Acad. Sci. USA, Feb. 1985, vol. 82, pp. 1020-1024.
Porton et al., "Immunoglobulin Heavy-Chain Enhancer is Required to Maintain Transfected y2A Gene Expression in a Pre-B-Cell Line", Molecular and Cellular Biology, Mar. 1990, vol. 10, No. 3, pp. 1076-1083.
Qin et al., "Interferon-beta gene therapy inhibits tumor formation and causes regression of established tumors in immune-deficient mice", Proc. Natl. Acad. Sci. USA, Nov. 1998, vol. 95, pp. 1411-14416.
Queen et al., "Immunoglobulin Gene Transcription is Activated by Downstream Sequence Elements", Cell, Jul. 1983, vol. 33, pp. 741-748.
Quinn et al., "Multiple Components Are Required for Sequence Recognition of the AP1 Site in the Gibbon Ape Leukemia Virus Enhancer", Molecular and Cellular Biology, Nov. 1989, vol. 9, No. 11, pp. 4713-4721.
Ravindranath et al., Role of Gangliosides in Active Immunotherapy with Melanoma Vaccine, Intern. Rev. Immunology, vol. 7, accepted for publication Apr. 26, 1991, published 1991, pp. 303-329.
Redondo et al., "A T Cell-Specific Transcriptional Enhancer Within the Human T Cell Receptor delta Locus", Science, New Series, vol. 247, No. 4947, Mar. 9, 1990, pp. 1225-1229.
Reisman et al., "Induced Expression from the Moloney Murine Leukemia Virus Long Terminal Repeat during Differentiation of Human Myeloid Cells is Mediated Through its Transcriptional Enhancer", Molecular and Cellular Biology, Aug. 1989, vol. 9, No. 8, pp. 3571-3575.
Resendez, Jr. et al., "Identification of Highly Conserved Regulatory Domains and Protein-Binding Sites in the Promoters of the Rat and Human Genes Encoding the Stress-Inducible 78-Kilodalton Glucose-Regulated Protein", Molecular and Cellular Biology, Oct. 1988, vol. 8, No. 10, pp. 4579-4584.
Rippe et al., "Regulatory Elements in the 5'-Flanking Region and the First Intron Contribute to Transcriptional Control of the Mouse Alpha 1 Type I Collagen Gene", Molecular and Cellular Biology, May 1989, vol. 9, No. 5, pp. 2224-2227.
Rittling et al., "AP-1/jun binding sites mediate serum inducibility of the human vimentin promoter", Nucleic Acids Research, vol. 17, No. 4, accepted for publication Dec. 27, 1988, published 1989, pp. 1619-1633.
Rodriguez et al., "Regulated Expression of Nuclear Genes by T3 RNA Polymerase and lac Repressor, Using Recombinant Vaccinia Virus Vectors", Journal of Virology, Oct. 1990, vol. 64, No. 10, pp. 4851-4857.
Rosen et al., "The Location of Cis-Acting Regulatory Sequences in the Human T Cell Lymphotropic Virus Type III (HTLV-III/LAV) Long Terminal Repeat", Cell, Jul. 1985, vol. 41, pp. 813-823.
Rosenberg et al., "Experience with the Use of High-Dose Interleukin-2 in the Treatment of 652 Cancer Patients", 109th Annual Meeting of the American Surgical Association, Colorado Springs, Colorado, Apr. 10-12, 1989, pp. 474-484.
Sakai et al., "Hormone-mediated repression: a negative glucocorticoid response element from the bovine prolactin gene", Genes & Development, accepted for publication Jul. 13, 1988, published 1988, pp. 1144-1154.
Sanjuan et al., "The contribution of epistasis to the architecture of fitness in an RNA virus", PNAS, Oct. 26, 2004, vol. 101, No. 43, pp. 15376-15379.
Satake et al., "Biological Activities of Oligonucleotides Spanning the F9 Point Mutation within the Enhancer Region of Polyomavirus DNA", Journal of Virology, Mar. 1988, vol. 62, No. 3, pp. 970-977.
Schaffner et al., "Redundancy of Information in Enhancers as a Principle of Mammalian Transcription Control", J. Mol. Biol., submitted for publication Dec. 10, 1987, published 1988, vol. 201, pp. 81-90.
Schnell et al., "Infectious rabies viruses from cloned cDNA", The EMBO Journal, Sep. 15, 1994, vol. 13, No. 18, pp. 4195-4203.
Searle et al., "Building a Metal-Responsive Promoter with Synthetic Regulatory Elements", Molecular and Cellular Biology, Jun. 1985, vol. 5, No. 6, pp. 1480-1489.
Shafren et al., "Systemic Therapy of Malignant Human Melanoma Tumors by a Common Cold-Producing Enterovirus, Coxsackievirus A21", Clinical Cancer Research, Jan. 1, 2004, vol. 10, pp. 53-60.
Sharp et al., "HIV TAR: An RNA Enhancer", Cell, Oct. 20, 1989, vol. 59, pp. 229-230.
Shaul et al., "Multiple nuclear proteins in liver cells are bound to hepatitis B virus enhancer element and its upstream sequences", The EMBO Journal, Jul. 1, 1987, vol. 6, No. 7, pp. 1913-1920.
Sherman et al., "Class II Box Consensus Sequences in the HLA-DR alpha Gene: Transcriptional Function and Interaction with Nuclear Proteins", Molecular and Cellular Biology, Jan. 1989, vol. 9, No. 1, pp. 50-56.
Sleigh et al., "SV40 enhancer activation during retinoic acid-induced differentiation of F9 embryonal carcinoma cells", The EMBO Journal, Dec. 30, 1985, vol. 4, No. 13B, pp. 3831-3837.
Spalholz et al., "Transactivation of a Bovine Papilloma Virus Transcriptional Regulatory Element by the E2 Gene Product", Cell, vol. 42, Aug. 1985, pp. 183-191.
Spandau et al., "trans-Activation of Viral Enhancers by the Hepatitis B Virus X Protein", Journal of Virology, Feb. 1988, vol. 62, No. 2, pp. 427-434.
Spandidos et al., "Host-specificities of papillomavirus, Moloney murine sarcoma virus and simian virus 40 enhancer sequences,", The EMBO Journal, 1983, vol. 2, No. 7, pp. 1193-1199.
Mitchell et al., "Active-Specific Immunotherapy for Melanoma", Journal of Clinical Oncology, vol. 8, No. 5, May 1990, pp. 856-869.
Fraley et al., "The Sev System: A New Disarmed TI Plasmid Vector System for Plant Transformation", Bio/Technology, vol. 3, Jul. 1985, pp. 629-635.
Irie et al., "Human Monoclonal Antibody to Ganglioside GM2 for Melanoma Treatment", The Lancet, vol. 333, Issue 8641, Apr. 1989, 2 pages.

(56) References Cited

OTHER PUBLICATIONS

Rosenberg et al., "Special Report Use of Tumor-Infiltrating Lmphcytes and Interleukin-2 in The Immunotherapy of Patients with Metastatic Melanoma", The New England Journal of Medicine, Dec. 22, 1988, pp. 1676-1680.
Usdin et al., "SP6 RNA Polymerase Containing Vaccinia Virus for Rapid Expression of Cloned Genes in Tissue Culture", Biotechniques, Feb. 1993, vol. 14, No. 2, pp. 222-224.
Irie Takashi et al: "Modifications of the PSAP region of the matrix protein lead to attenuation of vesicular stomatitis virus in vitro and in vivo", Journal of General Virology, Society for General Microbiology, Spencers Wood, GB, vol. 88, No. Pt. 9, Sep. 1, 2007, pp. 2559-2567, XP 002569284, ISSN: 0022-1317, DOI: 10.1099/VIR.0.83096-0.
European Search Report dated Aug. 19, 2013, issued in respect of corresponding European Application No. 10835567.8.
Office Action issued against corresponding Chinese Application No. 201080063490.X dated Dec. 23, 2013, along with an English translation.
Office Action issued against corresponding Chinese Application No. 201080063490.X dated May 13, 2013, along with an English translation.
Examination Report No. 1 issued against corresponding Australian Patent Application No. 2010329551, dated May 15, 2014.
Fourth Office Action issued on corresponding Chinese Patent Application No. 201080063490.X on Jan. 22, 2015, with English translation of text.
Notice of Reasons for Rejection issued on corresponding Japanese Patent Application No. 2012-542635 dated Feb. 27, 2015, with English translation of text.
Office Action issued on Mexican Patent Application No. MX/a/2012/006508 on Feb. 27, 2015, with English summary.
Sanjuan, Rafael et al., Proc. Natl. Acad. Sci., USA, 2004, vol. 101, No. 43, p. 15376-15379.
Restriction Requirement issued on corresponding U.S. Appl. No. 13/514,837 dated Jan. 14, 2014.
Office Action issued on corresponding U.S. Appl. No. 13/514,837 dated Aug. 1, 2014.
Notice of Allowance issued on corresponding U.S. Appl. No. 13/514,837 on Feb. 2, 2015.
Office Action issued on corresponding Israeli Patent Application No. 220221 on Feb. 25, 2015, along with an English translation.
Extended European Search Report and Opinion dated Nov. 21, 2014 for corresponding European Patent Application No. 12796050.8.
Third Office Action issued on corresponding Chinese Patent Application No. 201080063490.X on Aug. 13, 2014, with English translation of text.

* cited by examiner

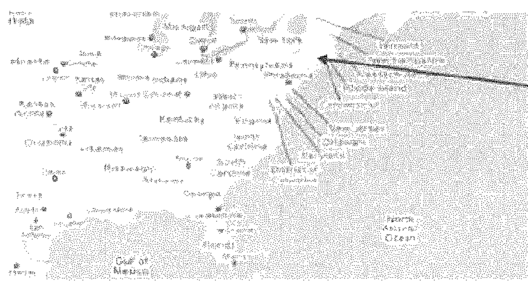
Farmington Virus:
-Rhabdovirus isolated from a healthy wild bird captured in Connecticut (R. Wallis 1969)
Fig. 1A
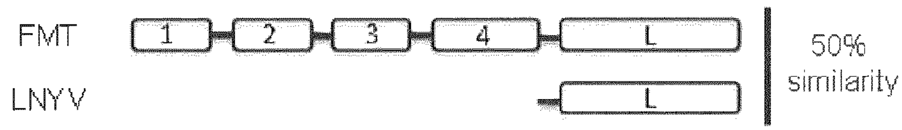
Fig. 1B
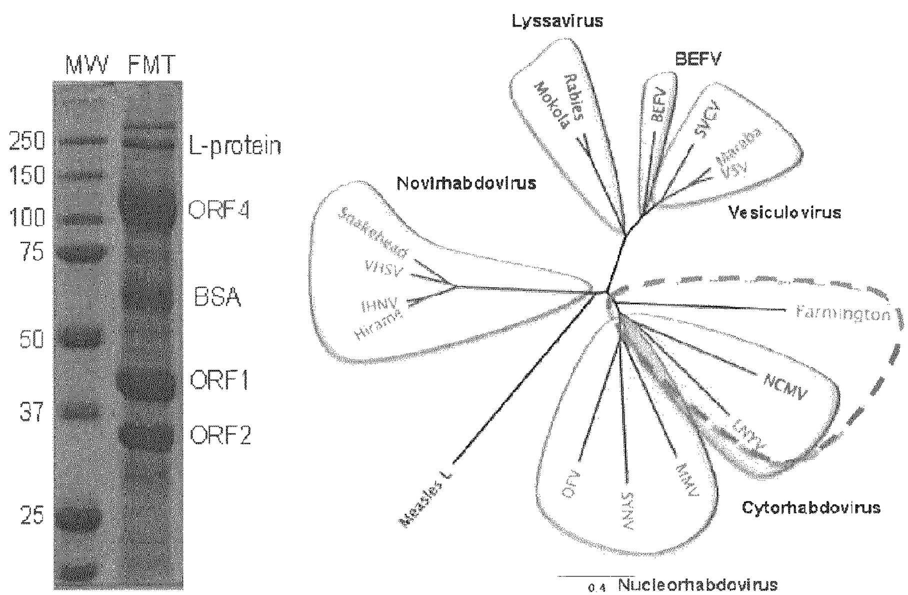
Fig. 1C
Fig. 1D

Figures 2A, 2B:
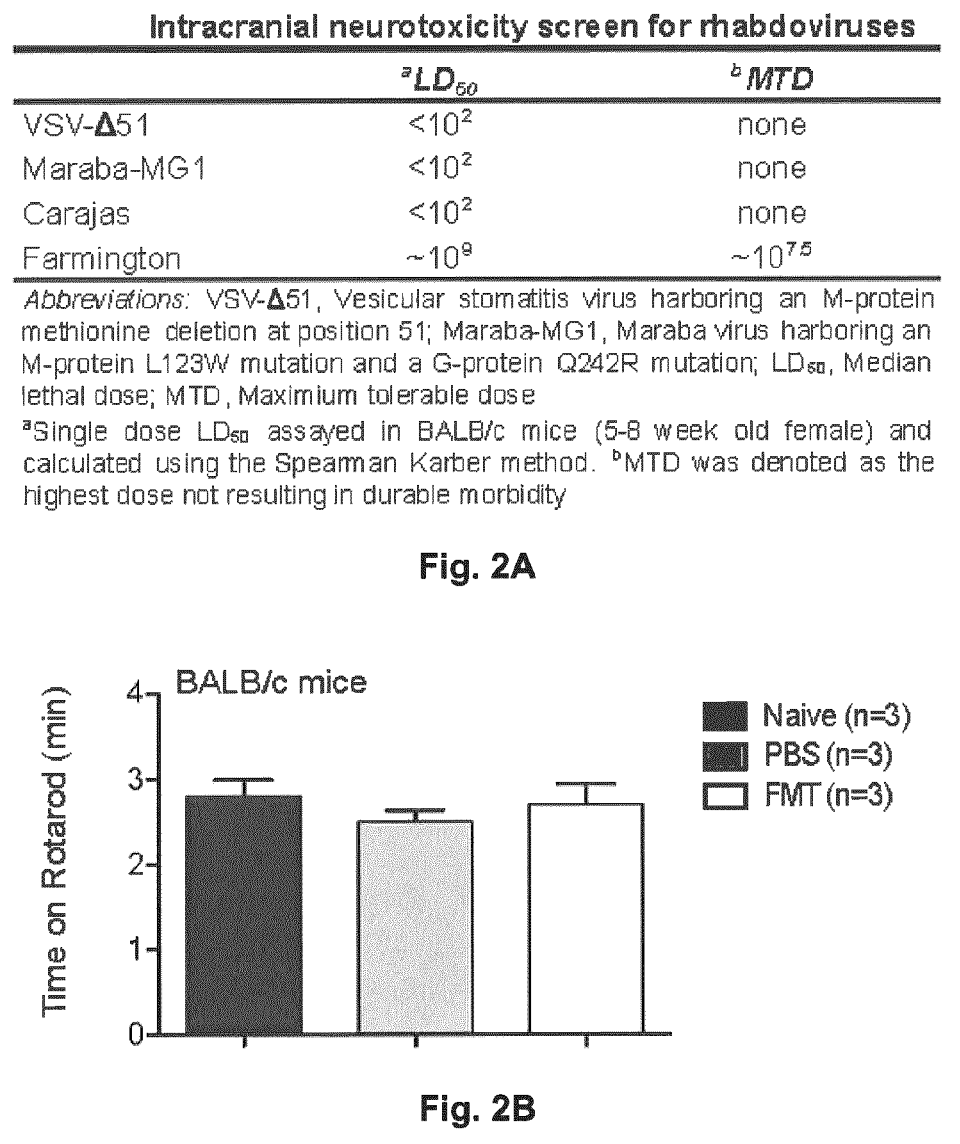

Intracranial neurotoxicity screen for rhabdoviruses

| | ${}^{a}LD_{50}$ | ${}^{b}MTD$ |
|---|---|---|
| VSV-Δ51 | <10² | none |
| Maraba-MG1 | <10² | none |
| Carajas | <10² | none |
| Farmington | ~10⁹ | ~10^7.5 |

*Abbreviations:* VSV-Δ51, Vesicular stomatitis virus harboring an M-protein methionine deletion at position 51; Maraba-MG1, Maraba virus harboring an M-protein L123W mutation and a G-protein Q242R mutation; $LD_{50}$, Median lethal dose; MTD, Maximium tolerable dose

[a]Single dose $LD_{50}$ assayed in BALB/c mice (5-8 week old female) and calculated using the Spearman Karber method. [b]MTD was denoted as the highest dose not resulting in durable morbidity

| *ROI* | *[a]3 mos* |
|---|---|
| Intracranial | 0/10 |
| Intravenous | 0/29 |

*Abbreviations:* FMT, farmington virus; ROI, route of administration

[a]denotes the number of animals treated that grew FMT virus from brain samples taken 3 mos post treatment

Farmington virus is highly lytic on GBM-derived cell lines

| | $^{a}EC_{50}$ < 0.1 moi |
|---|---|
| ***Tumor*** | |
| Human GBM-derived cell lines (9) | 100 |
| Human primary patient cells (3) | 66 |
| Mouse GBM-derived cell lines (3) | 66 |
| ***Normal*** | |
| Human normal cells (2) | 0 |
| Mouse normal cells (1) | 0 |

*Abbreviations:* GBM, glioblastoma multiforme; $EC_{50}$, half maximal effective concentration.

[a]values denote the percentage of cells within each classification that had an $EC_{50}$ < 0.1 moi. The actual $EC_{50}$ values for each cell lines are presented in Table S2.

Fig. 3A

Farmington virus is highly lytic on GBM-derived cell lines

| | $EC_{50}$ *(moi)* |
|---|---|
| ***Human GBM-derived cell lines*** | |
| SF268 | <0.001 |
| U343 | <0.001 |
| U118 | <0.001 |
| SNB19 | <0.001 |
| U87MG | <0.001 |
| SF265 | <0.01 |
| SNB75 | <0.01 |
| SF539 | <0.1 |
| U373 | <0.1 |
| ***Human primary patient cells*** | |
| GBM1 | <0.001 |
| GBM2 | <0.001 |
| GBM3 | >10 |
| ***Mouse GBM-derived cell lines*** | |
| CT-2A | <0.001 |
| DBT | <0.1 |
| GL261 | <10 |
| ***Human normal cells*** | |
| GM38 skin fibroblasts | 1 |
| Normal human astrocyte | >10 |
| ***Mouse normal cells*** | |
| 3T3 fibroblasts | >10 |

*Abbreviations*: GBM, glioblastoma multiforme; $EC_{50}$, half maximal effective concentration

Fig. 3C

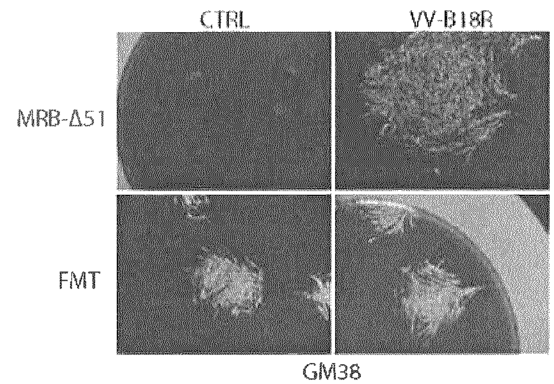
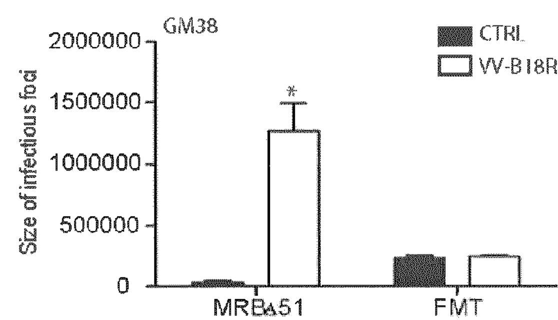
Fig. 6C
Fig. 6D
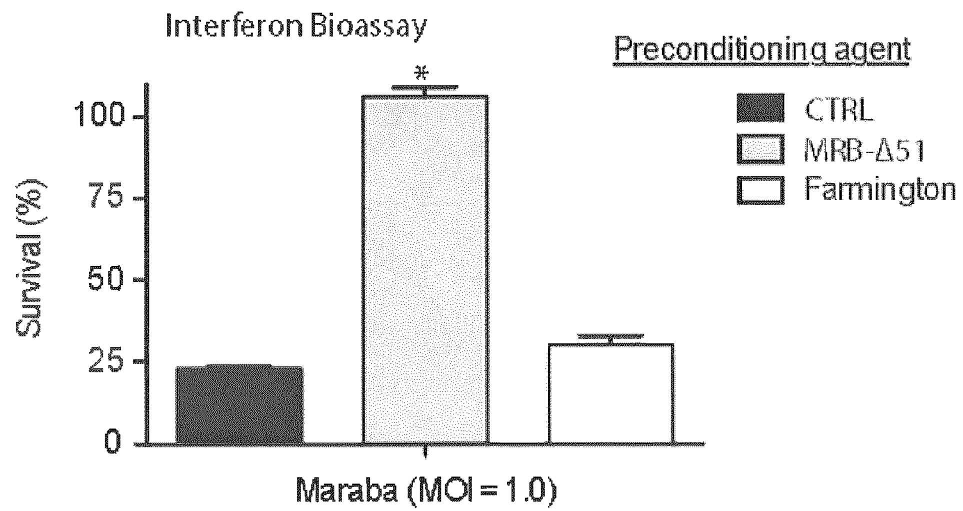
Fig. 6E

SEQUENCE LISTING

```
<160> NUMBER OF SEQ ID NOS: 12

<210> SEQ ID NO 1
<211> LENGTH: 12423
<212> TYPE: DNA
<213> ORGANISM: Farmington rhabdovirus
<220> FEATURE:
<221> NAME/KEY: promoter
<222> LOCATION: (134)..(149)
<220> FEATURE:
<221> NAME/KEY: misc_feature
<222> LOCATION: (206)..(1444)
<223> OTHER INFORMATION: ORF 1
<220> FEATURE:
<221> NAME/KEY: promoter
<222> LOCATION: (1562)..(1578)
<220> FEATURE:
<221> NAME/KEY: misc_feature
<222> LOCATION: (1640)..(2590)
<223> OTHER INFORMATION: ORF 2
<220> FEATURE:
<221> NAME/KEY: promoter
<222> LOCATION: (2799)..(2813)
<220> FEATURE:
<221> NAME/KEY: misc_feature
<222> LOCATION: (2894)..(3340)
<223> OTHER INFORMATION: ORF 3
<220> FEATURE:
<221> NAME/KEY: promoter
<222> LOCATION: (3457)..(3469)
<220> FEATURE:
<221> NAME/KEY: misc_feature
<222> LOCATION: (3603)..(5717)
<223> OTHER INFORMATION: ORF 4
<220> FEATURE:
<221> NAME/KEY: promoter
<222> LOCATION: (5766)..(5780)
<220> FEATURE:
<221> NAME/KEY: misc_feature
<222> LOCATION: (5832)..(12221)
<223> OTHER INFORMATION: ORF 5

<400> SEQUENCE: 1

ttacgacgca taagctgaga aacataagag actatgttca tagtcaccct gtattcatta     60

ttgactttta tgacctatta ttcgtgaggt catatgtgag gtaatgtcat ctgcttatgc    120

gtttgcttat aagataaaac gatagaccct tcacgggtaa atccttctcc ttgcagttct    180

cgccaagtac ctccaaagtc agacgatggc tcgtccgcta gctgctgcgc aacatctcat    240

aaccgagcgt cattcccttc aggcgactct gtcgcgggcg tccaagacca gagccgagga    300

attcgtcaaa gatttctacc ttcaagagca gtattctgtc ccgaccatcc cgacggacga    360

cattgcccag tctgggccca tgctgcttca ggccatcctg agcgaggaat acacaaaggc    420

cactgacata gcccaatcca tcctctggaa cactcccaca cccaacgggc tcctcagaga    480

gcatctagat gccgatgggg gaggctcatt cacagcgctg cccgcgtctg caatcagacc    540

cagcgacgag gcgaatgcat gggccgctcg catctccgac tcagggttgg ggcctgtctt    600

ctatgcagcc ctcgctgctt acatcatcgg ctggtcagga agaggagaga ctagccgcgt    660
```

```
gcagcagaac ataggtcaga aatggctgat gaacctgaac gcaatcttcg gcaccacgat    720
cacccatcca acaaccgtgc gtctgccaat caacgtcgtc aacaacagcc tcgcagtgag    780
gaacggactt gctgccacac tctggctata ctaccgttca tcacctcaga gtcaggacgc    840
gttcttctat gggctcatcc gtccctgttg cagtggatat ctcggcctgc tacatcgggt    900
gcaggagatt gatgagatgg agccggactt cctcagtgac ccccggatca tccaggtgaa    960
tgaggtctac agtgcactca gagccctggt tcaactggga aacgacttca agaccgccga   1020
tgatgagccc atgcaggtct gggcgtgcag gggaatcaac aacggatatc tgacatatct   1080
ctcagaaact cctgcgaaga aaggagctgt tgtgcttatg tttgcccaat gcatgctgaa   1140
gggcgactct gaggcctgga acagctaccg cactgcaacc tgggtgatgc cctattgcga   1200
caatgtggcc ctaggagcga tggcaggcta catccaagcc cgccagaaca ccagggcata   1260
tgaggtctca gcccagacag gtctcgacgt caacatggcc gcggtcaagg actttgaggc   1320
cagttcaaaa cccaaggctg ctccaatctc gctgatccca cgccccgctg atgtcgcatc   1380
ccgcacctct gagcgcccat ctattcctga ggttgacagc gacgaagagc tcggaggaat   1440
gtaaaccaat aagcttcact gccggtagtt taggcataca cacgcagttc cgttatccat   1500
cacacccgtc ccttctttta tgctgctatt atttcagttg ctaagcttcc tgatttgatt   1560
aacaaaaaac cgtagacctc ctacgtgagg tatagctaga aattggttct atcggttgag   1620
agtctttgta ctattagcca tggaggacta tttgtctagc ttagaggccg cgagagagct   1680
cgtccggacg gagctggagc ccaagcgtaa cctcatagcc agcttagagt ccgacgatcc   1740
cgatccggta atagcgccag cggtaaaacc aaaacatccc aagccatgcc tgagcactaa   1800
agaagaggat catctcccct ctcttcgcct actattcggc gcaaaacgag acacctcggt   1860
gggcgtagag cagactctcc acaagcgtct ctgcgcttgt ctcgacggtt acctgaccat   1920
gacgaagaaa gaggccaatg cctttaaggc cgcggctgaa gcagcagcat tagcagtcat   1980
ggacattaag atggagcatc agcgccagga tctagaggat ctgaccgctg ctatccctag   2040
gatagaattc aaactcaatg ccatcctgga aaacaacaag gagatagcca aggctgtaac   2100
tgctgctaag gagatggagc gggagatgtc gtggggggaa agcgccgcca gctcgctcaa   2160
gtctgtcacc ctagatgagt cgtttagggg ccctgaagag ctttcagagt catttggcat   2220
ccgatataag gtcagaacct ggaatgagtt caagaaggcg ctggaaacca gcattgtgga   2280
cctgaggcct agccctgttt catttaggga attacggact atgtggctgt ctcttgacac   2340
ctcctttagg ctcattgggt ttgccttcat tcccacatgc gagcgcctgg agaccaaagc   2400
caaatgcaag gagacaagga ctctactccc ccttgcagag tcgatcatgc gaagatggga   2460
cctgcgggat ccaaccatct tggagaaagc ctgcgtagta atgatgatcc gtgggaatga   2520
gattgcatcg ctgaatcagg taaaagatgt tctcccgacc acaattcgtg ggtggaagat   2580
cgcttattag tcactgctcc cattagtccc actagacggc atacttccat tccgcccttt   2640
aattcccctg tcagacactc atgctccgaa atcactaacc atccttgtcc accaagcaat   2700
acgcatattc agtagcactg catctcgccc tccccctatc aagccccagc gctgcagatc   2760
ttcaccacat atatacatgc atcaactaca tgtgatttag aaaaaaccag acccttcacg   2820
ggtaatagcc taactcacga acgttcctct cgtttcgtat gataaggcct taagcattgt   2880
cgatacggtc gttatgcgtc ggttcttttt aggagagagc agtgcccctg cgagggactg   2940
ggagtccgag cgacctcccc cctatgctgt tgaggtccct caaagtcacg ggataagagt   3000
caccgggtac ttccagtgca acgagcgtcc gaaatccaag aagaccctcc acagcttcgc   3060
```

```
cgtaaaactc tgcgacgcaa ttaagccggt tcgagcggat gctcccagct tgaagatagc   3120
aatatggacg gctctagatc tggccttcgt gaaacctccc aatggaactg taacaataga   3180
tgcggcggtg aaagctacac cgctaatcgg gaacacccag tacaccgtag gcgatgaaat   3240
cttccagatg ctagggagaa ggggtggcct gatcgtcatc aggaacttac cccatgatta   3300
tcctcgaacg ttgattgagt tcgcctctcc cgagccttga gcaccagggc atcggtccgc   3360
ccgccctgtg atctcccgta gccgggctca gcgatcaagc cggcccgggt cggggggggac  3420
tggtgcaaca caaggggcgg cagtggacgc tgattaacaa aaaaccacct atatagaccc   3480
ctcacggtct tagactctgt tgccagctga caaccaacac acaagacatc tctctgattc   3540
agccgacccg atcgattcct ccccacccaa ttcctaccaa cgcactcctc acaagctcca   3600
ccatgctcag gatccagatc cctccgattg ctatcattct ggtaagtctc ctcacactcg   3660
acctgtccgg tgcaaggagg acaaccacac aaagaatccc tctccttaat gattcgtggg   3720
atttgttctc gagctatggc gacattcccg aagaacttgt cgtataccag aactacagcc   3780
acaattcctc cgagttaccc cctcctggct tcgagagatg gtacataaac cgaagagtgg   3840
cagacacttc cataccgtgc aggggcccct gtctagtgcc ctacatcctt catggcctca   3900
atgacacaac tgtctctcga cggggaggag gatggcgaag gtccggaatg aagtacccaa   3960
cccacgctgt caggctaggc ccttcaacag acgacgagag agttgaggaa gacatcggct   4020
acgtcaatgt ctccgcacta tcctgcacag ggtcgcccgt tgagatggcg ataccaacaa   4080
tccccgactg caccagtgct atccatccac gatccgaggt tactgtgccc gtcaagctcg   4140
atgtcatgag acgaaatccc aactaccctc ccattagagc gtggtcgtgc atcggacaga   4200
aaatcaccaa ccgatgtgat tgggcactct tcggcgagaa cctcatatat actcaagttg   4260
aagctagctc tctagcattc aagcacacaa gagcctctct tttgaacgaa tccaacggga   4320
tagacgctga aggacgtgca gttccctata tcctcgggga tatcgaaccc gggtactgcc   4380
gaaccctatt caacacatgg gtctctagtg agatcgtgtc atgcacgccc atcgaacttg   4440
tcctagttga cctgaaccct ttgtccccgg gacatggcgg atatgctgta ttgctgccaa   4500
acggagacaa agtggatgta cacgacaagc atgcatggga tggggacaac aaaatgtgga   4560
gatgggtgta cgagaagaaa gatccctgtg cgttcgagct ggtatccagg gaagtgtgtc   4620
ttttctcact gagtaggggt agtagactga gaggagcaac ccctccccaa ggagagctcc   4680
tcacctgccc gcattcggga aaggcatttg acctgaaggg ggcccgaagg attacaccca   4740
tttcatgcaa aatcgacatg gaatatgact tgctgtcact accaaccgga gtcatcctag   4800
gcctccacct atcagaactc gggacctcct ttggcaacct ctcaatgagt cttgaaatgt   4860
atgaacctgc cacaactctg accccctgagc aaatcaactt ctcgcttaaa gagctgggaa  4920
gctggaccga ggctcaactg aagagcctgt ctcactcaat ctgcctctcc acattctcca   4980
tatgggaact atcggttggg atgatcgatc taaaccctac cagggcagca agggccttgc   5040
tccatgatga taacatactg gcaacattcg agaacggtca cttttccatc gtcagatgtc   5100
gtccggaaat agttcaagtc ccttcgcatc ctcgagcatg tcacatggat ctccgcccctt  5160
atgacaagca atcacgggca tcaaccctgg tggttcccct tgacaacagc actgccctcc   5220
tggtccccga caacatcgtg gttgaaggag tagaggccag tctatgcaac cactccgttg   5280
ccatcacgct gtcgaagaac agaactcact catacagcct ctatccccag ggtcgtcctg   5340
tgcttcgaca gaaaggtgcc gtggagctcc cgacgatagg gcccctccag ttacatcctg   5400
```

```
ccactcgagt ggacctttat acactgaaag agttccagga ggaccgaata gcgcgcagtc   5460
gagtcacaga catcaaggct gccgttgacg atctgcgtgc gaagtggcgt aaaggcaaat   5520
ttgaggcgga caccacggga gggggacttt ggtcggcgat tgtgggagtc ttcagttctc   5580
tcggggggtt cttcatgagg cccttgattg ctctcgcggc gatagtgacc tcaatcatca   5640
tcctgtatat ccttctgcgt gtactgtgtg ctgcctcatg ttcgacacac cgaagagtaa   5700
ggcaggactc ttggtaaaga ggactgcgat tgttgagtgg acaaacccta ggcctattcc   5760
gatttagaaa aaaccagacc tctcacgagg tcttttctac tagctgggtt ttcctcattc   5820
tatccagagc catggccttc gacccgaact ggcagagaga aggttatgaa tgggatccgt   5880
caagtgaggg cagaccgacc gatgagaacg aagacgacag aggtcatcgg ccaaaaaacga   5940
gacttcgtac attccttgcc cgcacgttaa atagccctat ccgagcccta ttctacacaa   6000
tattcctagg aattcgagcg gtttgggacg ggttcaaaag actcctacct gtgaggaccg   6060
aaaagggtta tgcgaggttt tctgagtgcg tcacatatgg aatgatcgga tgtgatgagt   6120
gtgtaataga cccggtgagg gttgtcattg agctgaccga gatgcagtta ccgattaaag   6180
gcaaaggctc tacgaggttg agagcaatga taactgaaga ccttctcacg gggatgcgca   6240
cagccgtgcc tcagatcaga gtgagatcga agatcctagc agagcggtta gggagagcaa   6300
tcggccgaga gaccttgccg gcaatgatcc atcatgagtg ggcatttgtg atggggaaga   6360
ttctcacttt catggcagac aatgtgggta tgaacgctga cacggtcgag ggcgttctat   6420
cactatcaga ggtcacacgg cgatgggata tcggcaactc tgtgtccgca gtgttcaatc   6480
ctgatggcct tactatcaga gtagaaaaca cgggttacat catgaccaga gagactgcct   6540
gcatgatcgg agacattcat gctcaatttg caatccaata cctagctgca tacctagacg   6600
aggtgatcgg cacaaggacg tctctctcac ccgccgaact gacctctctc aaactatggg   6660
gacttaacgt cctgaaactc ctaggacgga acggttatga ggtgatcgcc tgcatggagc   6720
ccatagggta cgctgtcctg atgatgggaa gagacaggag tcctgatccc tatgtcaatg   6780
acacctattt aaacagcatc ctctcagaat tccctgtcga ctctgacgct cgagcctgcg   6840
ttgaagccct cttaactatc tatatgagct tcggcacacc ccataaagtc tcggacgcat   6900
tcggcctctt cagaatgttg ggacatccga tggttgatgg agctgacggg attgaaaaga   6960
tgcgaaggtt aagcaagaag gtcaagatcc cagaccagtc tacagcgatc gacctcgggg   7020
ctatcatggc cgaactgttt gtgcggagtt tcgtaaagaa gcacaaaagg tggcccaact   7080
gctccatcaa tctcccgcca cgacacccct tccaccacgc ccgcctatgt gggtatgtcc   7140
cggctgaaac ccatccccta aacaacactg catcctgggc ggctgtggag ttcaaccagg   7200
aattcgagcc gccgagacag tacaaccttg cagacatcat tgatgacaag tcgtgctctc   7260
ccaacaagca tgagctatat ggtgcttgga tgaagtcaaa aacagctggg tggcaggaac   7320
aaaagaagct catactccga tggttcactg agaccatggt taaaccttcg gagctcctgg   7380
aagagattga tgcacacggc ttccgagaag aggataagtt gattggatta acaccaaagg   7440
agagagagct gaaattaaca ccaagaatgt tctccttgat gacattcaag ttcagaacct   7500
accaagtcct cactgagagt atggtcgccg atgagatcct cccgcacttc ccccagatca   7560
ccatgaccat gtccaaccac gaactcacaa agaggttgat tagcagaacg agacctcaat   7620
ctggaggagg gcgtgatgtt cacatcaccg tgaacataga tttccagaaa tggaacacaa   7680
acatgagaca cggactggtc aaacatgtct tcgagcgact ggacaacctc tttggcttca   7740
ccaacttaat cagacgaact catgaatact tccaggaggc gaaatactat ctggctgaag   7800
```

-continued

```
atggaactaa tctgtcgttc gacaggaacg gggagttaat agatggccca tacgtttaca   7860
ccggatcata cggggggaac gaggggttac gacagaagcc ctggacaata gttaccgtgt   7920
gtggaatata caaggtagct agagacctga aaatcaaaca tcagatcacc ggtcagggag   7980
ataatcaggt ggtcacccta atatttccgg atcgagagtt gccttcagat ccggtggaga   8040
ggagcaagta ctgtagagac aagagcagtc agttcctgac acgtctcagt caatatttcg   8100
ctgaggttgg tttgcccgtc aagactgaag agacatggat gtcatcacgt ctctatgctt   8160
acggtaagcg catgttctta gagggagttc cacttaagat gtttctcaag aagataggca   8220
gagctttcgc cctctcgaat gagtttgtcc cgtccctcga ggaagatctg gccagagtct   8280
ggagtgccac cagcgcagcg gtagagcttg acctaactcc ctacgtagga tatgtcctcg   8340
ggtgctgctt gtctgcgcag gcgatcagaa atcacctcat ctactcccct gttctggagg   8400
gccctctgct ggttaaggcc tacgagcgta agttcattaa ctacgacgga ggaacaaagc   8460
gggggcgat gcccggccta cgtccaacct ttgagagcct agtcaaaagt atctgctgga   8520
agccaaaggc catcggaggg tggccggtat tgatgttaga agatctcatc atcaaagggt   8580
tccctgatcc ggcgactagc gccctggctc aattgaagtc aatggtgcca tatacctctg   8640
gtatcgaccg ggagatcata ctttcctgtc tcaaccttcc cttatcgtcg gtggtatctc   8700
cgtcaatgtt gttaaaggac ccggcggcca tcaacaccat cacaaccccg tccgcgggcg   8760
acatcctgca agaggtcgcc agagactatg ttaccgatta cccactccaa aacccgcagc   8820
tcagagcagt ggtcaagaac gtgaagaccg agctagacac attggccagt gacttattca   8880
aatgtgaacc tttctttcct cctttaatga gcgatatctt ctcggcatct ctcccggcat   8940
atcaagacag gattgttcgc aagtgctcca cgacttctac aatcaggaga aaagctgccg   9000
agaggggctc cgactctctc ctcaaccgga tgaaaaggaa tgagatcaat aagatgatgt   9060
tacatctttg ggctacctgg ggaaggagcc ctctggccag attagacacc agatgtctca   9120
caacctgcac caagcaatta gcccaacagt atcggaacca gtcttgggga aagcagatcc   9180
atggagtctc agtcggccac cccttagaac tgttcggtcg aataacaccc agccatagat   9240
gcctacatga ggaggaccac ggagatttcc tgcaaacctt cgccagcgag catgtgaacc   9300
aagtggacac cgacatcacc acaactctgg ggccgttcta cccttacata ggctcggaga   9360
cgcgagaacg ggcagtcaag gttcgaaaag gagtgaatta cgtagttgag ccgcttctga   9420
aacccgcagt tcgactacta agagccatta attggttcat tcccgaggag tcagatgcgt   9480
cccatttgct gagcaatcta ttagcgtctg ttaccgacat caatcctcaa gaccactact   9540
catctaccga agtagggggg ggcaacgccg tccatcgcta cagctgccga ctatccgaca   9600
aattgagcag agtcaacaac ttatatcagt tgcatactta tttatctgtc acaacagagc   9660
ggttgaccaa gtacagtcga ggatcaaaaa acactgacgc acacttccag agcatgatga   9720
tttatgcaca aagccgtcat atagacctca tcttggagtc tctgcacacc ggagagatgg   9780
taccgttgga gtgtcatcat cacattgagt gcaatcactg tatagaggat atacccgacg   9840
agccaatcac gggggacccg gcttggactg aagtcaagtt tccttcaagt cctcaggagc   9900
cctttcttta catcaggcaa caagatctgc cggtcaaaga caaactcgag cctgtgcctc   9960
gcatgaacat cgtccgtctt gccggattgg gtccggaggc gattagtgag ctagcgcact  10020
actttgttgc attccgagtt atccgggcgt cagagacgga tgtcgaccct aacgatgttc  10080
tctcgtggac ctggctgagc cgaattgatc ctgacaaatt ggttgagtat atcgtgcatg  10140
```

-continued

```
tgttcgcttc actggaatgg catcatgtat taatgtcagg cgtgagtgtg agcgtcagag  10200
atgcattctt taagatgcta gtgtctaaaa gaatctcaga gactccgcta agttcattct  10260
attatctggc caacctgttc gttgaccctc agactcgcga agcactaatg agctctaaat  10320
acgggttcag cccccccgcc gagacagtcc ccaacgcaaa tgccgccgca gccgaaataa  10380
gaagatgctg tgcgaacagt gcgccgtcga tcttagaatc agcccttcac agccgtgagg  10440
ttgtttggat gccaggaacg aacaattatg gagacgttgt catctggtct cattacatta  10500
gattacggtt cagcgaagtt aaactagttg acattacacg atatcagcag tggtggagac  10560
agtctgagcg agacccctac gatttggtcc cggacatgca ggttcttgag agcgacctag  10620
atacgctgat gaaacggata ccgaggctca tgcgcaaggc gagacgtccc cctcttcagg  10680
taattcgaga ggacctggat gtcgcagtca tcaatgctga tcatcccgct cactctgtgc  10740
ttcagaacaa atacaggaaa ttgattttca gagagccgaa gattatcacg ggagctgtgt  10800
acaagtacct ctccctaaaa tcagagttga cagagttcac ctcagcaatg gtgatcggag  10860
acggaactgg aggtatcacc gccgccatga tggccgatgg gatagatgtg tggtatcaga  10920
cgctcgtcaa ctatgaccac gtgacacaac agggattatc cgtacaagcc ccggcagcat  10980
tggatcttct gcgcggggca ccctctggta ggctcttgaa tccgggaaga ttcgcatcat  11040
ttgggtctga cctaactgac cctcgattta cagcctactt tgatcaatat cccccgttca  11100
aggtggacac tctatggtct gacgcagagg gcgacttttg ggacaagcct tccaagttga  11160
atcaatactt tgagaacatc attgctttga gacatcggtt cgtgaagaca aatggacagc  11220
ttgtcgtgaa ggtgtatctg actcaagaca ctgctaccac aattgaagca ttcagaaaga  11280
agctgtcccc atgcgccatc atcgtgtctc tcttctcgac ggaaggctcc acagaatgct  11340
tcgtcctaag caatctcatc gcaccagaca cccctgtcga ccttgagatg gtggagaata  11400
tccctaaact aacatccctt gttccccaga ggacgacagt gaaatgctat tcccgacgag  11460
tagcgtgcat cagtaaaagg tggggacttt tcagatctcc gagcatagcc cttgaagtcc  11520
aaccgttcct tcactacatc acaaaggtca tctcagacaa aggaacacaa ctgagtctca  11580
tggcggtagc tgacacaatg atcaacagtt acaagaaggc tatctcaccc cgagtgttcg  11640
atctacaccg gcatagggcc gcactgggtt tcgggaggag atccttgcat ctcatctggg  11700
ggatgatcat ctcaccaatc gcttaccagc attttgagaa tccggccaag ttgatggatg  11760
tcctggacat gttgaccaat aacatctcag ctttcttatc gatatcgtcg tcaggatttg  11820
acctgtcatt tagtgtcagt gcagaccgag atgtccggat tgacagcaaa cttgtcagac  11880
tcccgctatt cgaaggatca gacctaaaat tcatgaaaac catcatgtct accctcggat  11940
ctgtgttcaa ccaggtcgag ccttttaagg ggatcgccat aaacccttct aaactaatga  12000
ctgtcaagag gacacaggag ttacgttaca acaacctaat ttacactaag gatgccatcc  12060
tattccccaa tgaagcggca aaaaacactg ccccgcttcg agccaacatg gtataccccg  12120
tccggggaga tctattcgcc cctaccgatc gcataccaat catgactcta gtcagcgatg  12180
agacaacacc tcagcactct cctccagagg atgaggcata actgaatcct ccctgaaggc  12240
tcacatgtcc cacgcgacgc aagatataac gacaagcaac tcgccctatt aactgtgatt  12300
aataaaaaac cgattattca gttgcttgag ggagtttcaa tccgttcagt gtatgatagg  12360
aagtttctga gatggtgggg attagggggc acctagagta tgtttgttcg ttttatgcgt  12420
cgt                                                                12423
```

<210> SEQ ID NO 2
<211> LENGTH: 12423
<212> TYPE: RNA
<213> ORGANISM: Farmington rhabdovirus

<400> SEQUENCE: 2

```
uuacgacgca uaagcugaga aacauaagag acuauguuca uagucacccu guauucauua     60

uugacuuuua ugaccuauua uucgugaggu cauaugugag guaaugucau cugcuuaugc    120

guuugcuuau aagauaaaac gauagacccu ucacggguaa auccuucucc uugcaguucu    180

cgccaaguac cuccaaaguc agacgauggc ucguccgcua gcugcugcgc aacaucucau    240

aaccgagcgu cauucccuuc aggcgacucu gucgcgggcg uccaagacca gagccgagga    300

auucgucaaa gauuucuacc uucaagagca guauucuguc ccgaccaucc cgacggacga    360

cauugcccag ucugggccca ugcugcuuca ggccauccug agcgaggaau acacaaaggc    420

cacugacaua gcccaaucca uccucuggaa cacucccaca cccaacgggc uccucagaga    480

gcaucuagau gccgaugggg gaggcucauu cacagcgcug cccgcgucug caaucagacc    540

cagcgacgag gcgaaugcau gggccgcucg caucuccgac ucaggguugg ggccugucuu    600

cuaugcagcc cucgcugcuu acaucaucgg cuggucagga agaggagaga cuagccgcgu    660

gcagcagaac auaggucaga aauggcugau gaaccugaac gcaaucuucg gcaccacgau    720

cacccaucca acaaccgugc gucugccaau caacgucguc aacaacagcc ucgcagugag    780

gaacggacuu gcugccacac ucuggcuaua cuaccguuca ucaccucaga gucaggacgc    840

guucuucuau gggcucaucc gucccuguug caguggauau cucggccugc uacaucgggu    900

gcaggagauu gaugagaugg agccggacuu ccucagugac cccggauca uccaggugaa    960

ugaggucuac agugcacuca gagcccuggu ucaacuggga aacgacuuca agaccgccga   1020

ugaugagccc augcaggucu gggcgugcag gggaaucaac aacggauauc ugacauaucu   1080

cucagaaacu ccugcgaaga aaggagcugu ugugcuuaug uuugcccaau gcaugcugaa   1140

gggcgacucu gaggccugga acagcuaccg cacugcaacc ugggugaugc ccuauugcga   1200

caauguggcc cuaggagcga uggcaggcua cauccaagcc cgccagaaca ccagggcaua   1260

ugaggucuca gcccagacag gucucgacgu caacauggcc gcggucaagg acuuugaggc   1320

caguucaaaa cccaaggcug cuccaaucuc gcugauccca cgccccgcug augucgcauc   1380

ccgcaccucu gagcgcccau cuauuccuga gguugacagc gacgaagagc ucggaggaau   1440

guaaaccaau aagcuucacu gccgguaguu uaggcauaca cacgcaguuc cguuauccau   1500

cacacccguc ccuucuuuua ugcugcuauu auuucaguug cuaagcuucc ugauuugauu   1560

aacaaaaaac cguagaccuc cuacgugagg uauagcuaga aauugguucu aucgguugag   1620

agucuuugua cuauuagcca uggaggacua uuugucuagc uuagaggccg cgagagagcu   1680

cguccggacg gagcuggagc ccaagcguaa ccucauagcc agcuuagagu ccgacgaucc   1740

cgauccggua auagcgccag cgguaaaacc aaaacauccc aagccaugcc ugagcacuaa   1800

agaagaggau caucuccccu cucuucgccu acuauucggc gcaaaacgag acaccucggu   1860

gggcguagag cagacucucc acaagcgucu cugcgcuugu cucgacgguu accugaccau   1920

gacgaagaaa gaggccaaug ccuuuaaggc cgcggcugaa gcagcagcau uagcagucau   1980

ggacauuaag auggagcauc agcgccagga ucuagaggau cugaccgcug cuaucccuag   2040

gauagaauuc aaacucaaug ccauccugga aaacaacaag gagauagcca aggcuguaac   2100

ugcugcuaag gagauggagc gggagauguc gugggggga agcgccgcca gcucgcucaa   2160
```

```
gucugucacc cuagaugagu cguuuagggg cccugaagag cuuucagagu cauuuggcau   2220
ccgauauaag gucagaaccu ggaaugaguu caagaaggcg cuggaaacca gcauugugga   2280
ccugaggccu agcccuguuu cauuuaggga auuacggacu auguggcugu cucuugacac   2340
cuccuuuagg cucauugggu uugccuucau ucccacaugc gagcgccugg agaccaaagc   2400
caaaugcaag gagacaagga cucuacuccc ccuugcagag ucgaucaugc gaagauggga   2460
ccugcgggau ccaaccaucu uggagaaagc cugcguagua augaugaucc gugggaauga   2520
gauugcaucg cugaaucagg uaaaagaugu ucucccgacc acaauucgug gguggaagau   2580
cgcuuauuag ucacugcucc cauuaguccc acuagacggc auacuuccau uccgcccuuu   2640
aauuccccug ucagacacuc augcuccgaa aucacuaacc auccuugucc accaagcaau   2700
acgcauauuc aguagcacug caucucgccc ucccccuauc aagccccagc gcugcagauc   2760
uucaccacau auauacaugc aucaacuaca ugugauuuag aaaaaaccag acccuucacg   2820
gguaauagcc uaacucacga acguuccucu cguuucguau gauaaggccu uaagcauugu   2880
cgauacgguc guuaugcguc gguucuuuuu aggagagagc agugccccug cgagggacug   2940
ggaguccgag cgaccucccc ccuaugcugu ugaggucccu caaagucacg ggauaagagu   3000
caccggguac uuccagugca acgagcgucc gaaauccaag aagacccucc acagcuucgc   3060
cguaaaacuc ugcgacgcaa uuaagccggu ucgagcggau gcucccagcu ugaagauagc   3120
aauauggacg gcucuagauc uggccuucgu gaaaccuccc aauggaacug uaacaauaga   3180
ugcggcggug aaagcuacac cgcuaaucgg gaacacccag uacaccguag gcgaugaaau   3240
cuuccagaug cuagggagaa ggggguggccu gaucgucauc aggaacuuac cccaugauua   3300
uccucgaacg uugauugagu ucgccucucc cgagccuuga gcaccagggc aucgguccgc   3360
ccgcccugug aucucccgua gccgggcuca gcgaucaagc cggcccgggu cgggggggac   3420
uggugcaaca caaggggcgg caguggacgc ugauuaacaa aaaaccaccu auauagaccc   3480
cucacggucu uagacucugu ugccagcuga caaccaacac acaagacauc ucucugauuc   3540
agccgacccg aucgauuccu ccccacccaa uuccuaccaa cgcacuccuc acaagcucca   3600
ccaugcucag gauccagauc ccuccgauug cuaucauucu gguaagucuc cucacacucg   3660
accuguccgg ugcaaggagg acaaccacac aaagaauccc ucuccuuaau gauucguggg   3720
auuuguucuc gagcuauggc gacauucccg aagaacuugu cguauaccag aacuacagcc   3780
acaauuccuc cgaguuaccc ccuccuggcu ucgagagaug guacauaaac cgaagagugg   3840
cagacacuuc cauaccgugc aggggccccu gucuagugcc cuacauccuu cauggccuca   3900
augacacaac ugucucucga cggggaggag gauggcgaag guccggaaug aaguacccaa   3960
cccacgcugu caggcuaggc ccuucaacag acgacgagag aguugaggaa gacaucggcu   4020
acgucaaugu cuccgcacua uccugcacag ggucgcccgu ugagauggcg auaccaacaa   4080
uccccgacug caccagugcu auccauccac gauccgaggu uacugugccc gucaagcucg   4140
augucaugag acgaaauccc aacuacccuc ccauuagagc gugguucgugc aucggacaga   4200
aaaucaccaa ccgaugugau ugggcacucu ucggcgagaa ccucauauau acucaaguug   4260
aagcuagcuc ucuagcauuc aagcacacaa gagccucucu uuugaacgaa uccaacggga   4320
uagacgcuga aggacgugca guucccuaua ucccucgggga uaucgaaccc ggguacugcc   4380
gaacccuauu caacacaugg gucucuagug agaucguguc augcacgccc aucgaacuug   4440
uccuaguuga ccugaacccu uuguccccgg gacauggcgg auaugcugua uugcugccaa   4500
acggagacaa aguggaugua cacgacaagc augcauggga uggggacaac aaaaugugga   4560
```

```
gaugggugua cgagaagaaa gaucccugug cguucgagcu gguauccagg gaagugugucc   4620

uuuucucacu gaguaggggu aguagacuga gaggagcaac cccuccccaa ggagagcucc   4680

ucaccugccc gcauucggga aaggcauuug accugaaggg ggcccgaagg auuacaccca   4740

uuucaugcaa aaucgacaug gaauaugacu ugcugucacu accaaccgga gucauccuag   4800

gccuccaccu aucagaacuc gggaccuccu uuggcaaccu cucaaugagu cuugaaaugu   4860

augaaccugc cacaacucug accccugagc aaaucaacuu cucgcuuaaa gagcugggaa   4920

gcuggaccga ggcucaacug aagagccugu cucacucaau cugccucucc acauucucca   4980

uaugggaacu aucgguuggg augaucgauc uaaacccuac cagggcagca agggccuugc   5040

uccaugauga uaacauacug gcaacauucg agaacgguca cuuuuccauc gucagauguc   5100

guccggaaau aguucaaguc ccuucgcauc cucgagcaug ucacauggau cuccgcccuu   5160

augacaagca aucacgggca ucaacccugg ugguuccccu ugacaacagc acugcccucc   5220

ugguccccga caacaucgug guugaaggag uagaggccag ucuaugcaac cacuccguug   5280

ccaucacgcu gucgaagaac agaacucacu cauacagccu cuauccccag ggucguccug   5340

ugcuucgaca gaaaggugcc guggagcucc cgacgauagg gccccuccag uuacauccug   5400

ccacucgagu ggaccuuuau acacugaaag aguuccagga ggaccgaaua gcgcgcaguc   5460

gagucacaga caucaaggcu gccguugacg aucugcgugc gaaguggcgu aaaggcaaau   5520

uugaggcgga caccacggga gggggacuuu ggucggcgau ugugggaguc uucaguucuc   5580

ucggggggguu cuucaugagg cccuugauug cucucgcggc gauagugacc ucaaucauca   5640

uccuguauau ccuucugcgu guacugugug cugccucaug uucgacacac cgaagaguaa   5700

ggcaggacuc uugguaaaga ggacugcgau uguugagugg acaaacccua ggccuauucc   5760

gauuuagaaa aaaccagacc ucucacgagg ucuuuucuac uagcuggguu uuccucauuc   5820

uauccagagc cauggccuuc gacccgaacu ggcagagaga agguuaugaa ugggauccgu   5880

caagugaggg cagaccgacc gaugagaacg aagacgacag aggucaucgg ccaaaaacga   5940

gacuucguac auuccuugcc cgcacguuaa auagcccuau ccgagcccua uucuacacaa   6000

uauuccuagg aauucgagcg guuugggacg gguucaaaag acuccuaccu gugaggaccg   6060

aaaaggguua ugcgagguuu ucugagugcg ucacauaugg aaugaucgga ugugaugagu   6120

guguaauaga cccggugagg guugucauug agcugaccga gaugcaguua ccgauuaaag   6180

gcaaaggcuc uacgagguug agagcaauga uaacugaaga ccuucucacg ggaugcgca   6240

cagccgugcc ucagaucaga gugagaucga agauccuagc agagcgguua gggagagcaa   6300

ucggccgaga gaccuugccg gcaaugaucc aucaugagug ggcauuugug augggggaaga   6360

uucucacuuu cauggcagac aaugugggua ugaacgcuga cacggucgag ggcguucuau   6420

cacuaucaga ggucacacgg cgaugggaua ucggcaacuc uguguccgca guguucaauc   6480

cugauggccu uacuaucaga guagaaaaca cggguuacau caugaccaga gagacugccu   6540

gcaugaucgg agacauucau gcucaauuug caauccaaua ccuagcugca uaccuagacg   6600

aggugaucgg cacaaggacg ucucucucac ccgccgaacu gaccucucuc aaacuauggg   6660

gacuuaacgu ccugaaacuc cuaggacgga acgguuauga ggugaucgcc ugcauggagc   6720

ccauagggua cgcuguccug augaugggaa gagacaggag uccugauccc uaugucaaug   6780

acaccuauuu aaacagcauc cucucagaau ucccugucga cucugacgcu cgagccugcg   6840

uugaagcccu cuuaacuauc uauaugagcu ucggcacacc ccauaaaguc ucggacgcau   6900
```

-continued

```
ucggccucuu cagaauguug ggacauccga ugguugaugg agcugacggg auugaaaaga   6960
ugcgaagguu aagcaagaag gucaagaucc cagaccaguc uacagcgauc gaccucgggg   7020
cuaucauggc cgaacuguuu gugcggaguu ucguaaagaa gcacaaaagg uggcccaacu   7080
gcuccaucaa ucucccgcca cgacaccccu uccaccacgc ccgccuaugu ggguaugucc   7140
cggcugaaac ccauccccua aacaacacug cauccugggc ggcuguggag uucaaccagg   7200
aauucgagcc gccgagacag uacaaccuug cagacaucau ugaugacaag ucgugcucuc   7260
ccaacaagca ugagcuauau ggugcuugga ugaagucaaa aacagcuggg uggcaggaac   7320
aaaagaagcu cauacuccga ugguucacug agaccauggu uaaaccuucg gagcuccugg   7380
aagagauuga ugcacacggc uuccgagaag aggauaaguu gauuggauua acaccaaagg   7440
agagagagcu gaaauuaaca ccaagaaugu ucuccuugau gacauucaag uucagaaccu   7500
accaaguccu cacugagagu auggucgccg augagauccu cccgcacuuc ccccagauca   7560
ccaugaccau guccaaccac gaacucacaa agagguugau uagcagaacg agaccucaau   7620
cuggaggagg gcgugauguu cacaucaccg ugaacauaga uuuccagaaa uggaacacaa   7680
acaugagaca cggacugguc aaacaugucu ucgagcgacu ggacaaccuc uuuggcuuca   7740
ccaacuuaau cagacgaacu caugaauacu uccaggaggc gaaauacuau cuggcugaag   7800
auggaacuaa ucugucguuc gacaggaacg gggaguuaau agauggccca uacguuuaca   7860
ccggaucaua cgggggggaac gaggggguuac gacagaagcc cuggacaaua guuaccgugu   7920
guggaauaua caagguagcu agagaccuga aaaucaaaca ucagaucacc ggucagggag   7980
auaaucaggu ggucacccua auauuuccgg aucgagaguu gccuucagau ccgguggaga   8040
ggagcaagua cuguagagac aagagcaguc aguuccugac acgucucagu caauauuucg   8100
cugagguugg uuugcccguc aagacugaag agacauggau gucaucacgu cucuaugcuu   8160
acgguaagcg cauguucuua gagggaguuc cacuuaagau guuucucaag aagauaggca   8220
gagcuuucgc ccucucgaau gaguuugucc cgucccucga ggaagaucug gccagagucu   8280
ggagugccac cagcgcagcg guagagcuug accuaacucc cuacguagga uauguccucg   8340
ggugcugcuu gucugcgcag gcgaucagaa aucaccucau cuacuccccu guucuggagg   8400
gcccucugcu gguuaaggcc uacgagcgua aguucauuaa cuacgacgga ggaacaaagc   8460
ggggggcgau gcccggccua cguccaaccu uugagagccu agucaaaagu aucugcugga   8520
agccaaaggc caucggaggg uggccgguau ugauguuaga agaucucauc aucaaagggu   8580
ucccugaucc ggcgacuagc gcccuggcuc aauugaaguc aaggugccaa uauaccucug   8640
guaucgaccg ggagaucaua cuuuccuguc ucaaccuucc cuuaucgucg gugguaucuc   8700
cgucaauguu guuaaaggac ccggcggcca ucaacaccau cacaaccccg uccgcgggcg   8760
acauccugca agaggucgcc agagacuaug uuaccgauua cccacuccaa aacccgcagc   8820
ucagagcagu ggucaagaac gugaagaccg agcuagacac auuggccagu gacuuauuca   8880
aaugugaacc uuucuuuccu ccuuuaauga gcgauaucuu cucggcaucu cucccggcau   8940
aucaagacag gauuguucgc aagugcucca cgacuucuac aaucaggaga aaagcugccg   9000
agaggggcuc cgacucucuc cucaaccgga ugaaaaggaa ugagaucaau aagaugaugu   9060
uacaucuuug ggcuaccugg ggaaggagcc cucuggccag auuagacacc agaugucuca   9120
caaccugcac caagcaauua gcccaacagu aucggaacca gucuuggggga aagcagaucc   9180
auggagucuc agucggccac ccccuuagaac uguucggucg aauaacaccc agccauagau   9240
gccuacauga ggaggaccac ggagauuucc ugcaaaccuu cgccagcgag caugugaacc   9300
```

```
aaguggacac cgacaucacc acaacucugg ggccguucua cccuuacaua ggcucggaga   9360
cgcgagaacg ggcagucaag guucgaaaag gagugaauua cguaguugag ccgcuucuga   9420
aacccgcagu ucgacuacua agagccauua auugguucau ucccgaggag ucagaugcgu   9480
cccauuugcu gagcaaucua uuagcgucug uuaccgacau caauccucaa gaccacuacu   9540
caucuaccga aguagggggg ggcaacgccg uccaucgcua cagcugccga cuauccgaca   9600
aauugagcag agucaacaac uuauaucagu ugcauacuua uuuaucuguc acaacagagc   9660
gguugaccaa guacagucga ggaucaaaaa acacugacgc acacuuccag agcaugauga   9720
uuuaugcaca aagccgucau auagaccuca ucuuggaguc ucugcacacc ggagagaugg   9780
uaccguugga gugucaucau cacauugagu gcaaucacug uauagaggau auacccgacg   9840
agccaaucac gggggacccg gcuuggacug aagucaaguu uccuucaagu ccucaggagc   9900
ccuuucuuua caucaggcaa caagaucugc cggucaaaga caaacucgag ccugugccuc   9960
gcaugaacau cguccgucuu gccggauugg guccggaggc gauuagugag cuagcgcacu  10020
acuuuguugc auuccgaguu auccgggcgu cagagacgga ugucgacccu aacgauguuc  10080
ucucguggac cuggcugagc cgaauugauc cugacaaauu gguugaguau aucgugcaug  10140
uguucgcuuc acuggaaugg caucauguau uaaugucagg cgugagugug agcgucagag  10200
augcauucuu uaagaugcua gugucuaaaa gaaucucaga gacuccgcua aguucauucu  10260
auuaucuggc caaccuguuc guugacccuc agacucgcga agcacuaaug agcucuaaau  10320
acggguucag cccccccgcc gagacagucc ccaacgcaaa ugccgccgca gccgaaauaa  10380
gaagaugcug ugcgaacagu gcgccgucga ucuuagaauc agcccuucac agccgugagg  10440
uuguuuggau gccaggaacg aacaauuaug gagacguugu caucuggucu cauuacauua  10500
gauuacgguu cagcgaaguu aaacuaguug acauuacacg auaucagcag ugguggagac  10560
agucugagcg agaccccuac gauuuggucc cggacaugca gguucuugag agcgaccuag  10620
auacgcugau gaaacggaua ccgaggcuca ugcgcaaggc gagacguccc ccucuucagg  10680
uaauucgaga ggaccuggau gucgcaguca ucaaugcuga ucaucccgcu cacucugugc  10740
uucagaacaa auacaggaaa uugauuuuca gagagccgaa gauuaucacg ggagcugugu  10800
acaaguaccu cucccuaaaa ucagaguuga cagaguucac cucagcaaug gugaucggag  10860
acggaacugg agguaucacc gccgccauga uggccgaugg gauagaugug ugguaucaga  10920
cgcucgucaa cuaugaccac gugacacaac agggauuauc cguacaagcc ccggcagcau  10980
uggaucuucu gcgcggggca cccucuggua ggcucuugaa uccgggaaga uucgcaucau  11040
uugggucuga ccuaacugac ccucgauuua cagccuacuu ugaucaauau cccccguuca  11100
agguggacac ucuauggucu gacgcagagg gcgacuuuug ggacaagccu uccaaguuga  11160
aucaauacuu ugagaacauc auugcuuuga gacaucgguu cgugaagaca aauggacagc  11220
uugucgugaa gguguaucug acucaagaca cugcuaccac aauugaagca uucagaaaga  11280
agcugucccc augcgccauc aucgugucuc ucuucucgac ggaaggcucc acagaaugcu  11340
ucguccuaag caaucucauc gcaccagaca ccccugucga ccuugagaug guggagaaua  11400
ucccuaaacu aacaucccuu guuccccaga ggacgacagu gaaaugcuau ucccgacgag  11460
uagcgugcau caguaaaagg uggggacuuu ucagaucucc gagcauagcc cuugaagucc  11520
aaccguuccu ucacuacauc acaaagguca ucucagacaa aggaacacaa cugagucuca  11580
uggcgguagc ugacacaaug aucaacaguu acaagaaggc uaucucaccc cgaguguucg  11640
```

```
aucuacaccg gcauagggcc gcacuggguu ucgggaggag auccuugcau cucaucuggg  11700

ggaugaucau cucaccaauc gcuuaccagc auuuugagaa uccggccaag uugauggaug  11760

uccuggacau guugaccaau aacaucucag cuuucuuauc gauaucgucg ucaggauuug  11820

accugucauu uagugucagu gcagaccgag auguccggau ugacagcaaa cuugucagac  11880

ucccgcuauu cgaaggauca gaccuaaaau ucaugaaaac caucaugucu acccucggau  11940

cuguguucaa ccaggucgag ccuuuuaagg ggaucgccau aaacccuucu aaacuaauga  12000

cugucaagag gacacaggag uuacguuaca acaaccuaau uuacacuaag gaugccaucc  12060

uauuccccaa ugaagcggca aaaaacacug ccccgcuucg agccaacaug guauaccccg  12120

uccggggaga ucuauucgcc ccuaccgauc gcauaccaau caugacucua gucagcgaug  12180

agacaacacc ucagcacucu ccuccagagg augaggcaua acugaauccu cccugaaggc  12240

ucacaugucc cacgcgacgc aagauauaac gacaagcaac ucgcccuauu aacugugauu  12300

aauaaaaaac cgauuauuca guugcuugag ggaguuucaa uccguucagu guaugauagg  12360

aaguuucuga gauggugggg auuagggggc accuagagua uguuuguucg uuuuaugcgu  12420

cgu                                                                12423
```

```
<210> SEQ ID NO 3
<211> LENGTH: 412
<212> TYPE: PRT
<213> ORGANISM: Farmington rhabdovirus

<400> SEQUENCE: 3

Met Ala Arg Pro Leu Ala Ala Ala Gln His Leu Ile Thr Glu Arg His
1               5                   10                  15

Ser Leu Gln Ala Thr Leu Ser Arg Ala Ser Lys Thr Arg Ala Glu Glu
            20                  25                  30

Phe Val Lys Asp Phe Tyr Leu Gln Glu Gln Tyr Ser Val Pro Thr Ile
        35                  40                  45

Pro Thr Asp Asp Ile Ala Gln Ser Gly Pro Met Leu Leu Gln Ala Ile
    50                  55                  60

Leu Ser Glu Glu Tyr Thr Lys Ala Thr Asp Ile Ala Gln Ser Ile Leu
65                  70                  75                  80

Trp Asn Thr Pro Thr Pro Asn Gly Leu Leu Arg Glu His Leu Asp Ala
                85                  90                  95

Asp Gly Gly Gly Ser Phe Thr Ala Leu Pro Ala Ser Ala Ile Arg Pro
            100                 105                 110

Ser Asp Glu Ala Asn Ala Trp Ala Ala Arg Ile Ser Asp Ser Gly Leu
        115                 120                 125

Gly Pro Val Phe Tyr Ala Ala Leu Ala Ala Tyr Ile Ile Gly Trp Ser
    130                 135                 140

Gly Arg Gly Glu Thr Ser Arg Val Gln Gln Asn Ile Gly Gln Lys Trp
145                 150                 155                 160

Leu Met Asn Leu Asn Ala Ile Phe Gly Thr Thr Ile Thr His Pro Thr
                165                 170                 175

Thr Val Arg Leu Pro Ile Asn Val Val Asn Asn Ser Leu Ala Val Arg
            180                 185                 190

Asn Gly Leu Ala Ala Thr Leu Trp Leu Tyr Tyr Arg Ser Ser Pro Gln
        195                 200                 205

Ser Gln Asp Ala Phe Phe Tyr Gly Leu Ile Arg Pro Cys Cys Ser Gly
    210                 215                 220

Tyr Leu Gly Leu Leu His Arg Val Gln Glu Ile Asp Glu Met Glu Pro
```

```
225                 230                 235                 240

Asp Phe Leu Ser Asp Pro Arg Ile Ile Gln Val Asn Glu Val Tyr Ser
                245                 250                 255

Ala Leu Arg Ala Leu Val Gln Leu Gly Asn Asp Phe Lys Thr Ala Asp
            260                 265                 270

Asp Glu Pro Met Gln Val Trp Ala Cys Arg Gly Ile Asn Asn Gly Tyr
        275                 280                 285

Leu Thr Tyr Leu Ser Glu Thr Pro Ala Lys Lys Gly Ala Val Val Leu
    290                 295                 300

Met Phe Ala Gln Cys Met Leu Lys Gly Asp Ser Glu Ala Trp Asn Ser
305                 310                 315                 320

Tyr Arg Thr Ala Thr Trp Val Met Pro Tyr Cys Asp Asn Val Ala Leu
                325                 330                 335

Gly Ala Met Ala Gly Tyr Ile Gln Ala Arg Gln Asn Thr Arg Ala Tyr
            340                 345                 350

Glu Val Ser Ala Gln Thr Gly Leu Asp Val Asn Met Ala Ala Val Lys
        355                 360                 365

Asp Phe Glu Ala Ser Ser Lys Pro Lys Ala Ala Pro Ile Ser Leu Ile
    370                 375                 380

Pro Arg Pro Ala Asp Val Ala Ser Arg Thr Ser Glu Arg Pro Ser Ile
385                 390                 395                 400

Pro Glu Val Asp Ser Asp Glu Glu Leu Gly Gly Met
                405                 410


<210> SEQ ID NO 4
<211> LENGTH: 316
<212> TYPE: PRT
<213> ORGANISM: Farmington rhabdovirus

<400> SEQUENCE: 4

Met Glu Asp Tyr Leu Ser Ser Leu Glu Ala Ala Arg Glu Leu Val Arg
1               5                   10                  15

Thr Glu Leu Glu Pro Lys Arg Asn Leu Ile Ala Ser Leu Glu Ser Asp
            20                  25                  30

Asp Pro Asp Pro Val Ile Ala Pro Ala Val Lys Pro Lys His Pro Lys
        35                  40                  45

Pro Cys Leu Ser Thr Lys Glu Glu Asp His Leu Pro Ser Leu Arg Leu
    50                  55                  60

Leu Phe Gly Ala Lys Arg Asp Thr Ser Val Gly Val Glu Gln Thr Leu
65                  70                  75                  80

His Lys Arg Leu Cys Ala Cys Leu Asp Gly Tyr Leu Thr Met Thr Lys
                85                  90                  95

Lys Glu Ala Asn Ala Phe Lys Ala Ala Ala Glu Ala Ala Ala Leu Ala
            100                 105                 110

Val Met Asp Ile Lys Met Glu His Gln Arg Gln Asp Leu Glu Asp Leu
        115                 120                 125

Thr Ala Ala Ile Pro Arg Ile Glu Phe Lys Leu Asn Ala Ile Leu Glu
    130                 135                 140

Asn Asn Lys Glu Ile Ala Lys Ala Val Thr Ala Ala Lys Glu Met Glu
145                 150                 155                 160

Arg Glu Met Ser Trp Gly Glu Ser Ala Ala Ser Ser Leu Lys Ser Val
                165                 170                 175

Thr Leu Asp Glu Ser Phe Arg Gly Pro Glu Glu Leu Ser Glu Ser Phe
            180                 185                 190
```

```
Gly Ile Arg Tyr Lys Val Arg Thr Trp Asn Glu Phe Lys Lys Ala Leu
        195                 200                 205

Glu Thr Ser Ile Val Asp Leu Arg Pro Ser Pro Val Ser Phe Arg Glu
    210                 215                 220

Leu Arg Thr Met Trp Leu Ser Leu Asp Thr Ser Phe Arg Leu Ile Gly
225                 230                 235                 240

Phe Ala Phe Ile Pro Thr Cys Glu Arg Leu Glu Thr Lys Ala Lys Cys
                245                 250                 255

Lys Glu Thr Arg Thr Leu Leu Pro Leu Ala Glu Ser Ile Met Arg Arg
            260                 265                 270

Trp Asp Leu Arg Asp Pro Thr Ile Leu Glu Lys Ala Cys Val Val Met
        275                 280                 285

Met Ile Arg Gly Asn Glu Ile Ala Ser Leu Asn Gln Val Lys Asp Val
    290                 295                 300

Leu Pro Thr Thr Ile Arg Gly Trp Lys Ile Ala Tyr
305                 310                 315


<210> SEQ ID NO 5
<211> LENGTH: 148
<212> TYPE: PRT
<213> ORGANISM: Farmington rhabdovirus

<400> SEQUENCE: 5

Met Arg Arg Phe Phe Leu Gly Glu Ser Ser Ala Pro Ala Arg Asp Trp
1               5                   10                  15

Glu Ser Glu Arg Pro Pro Pro Tyr Ala Val Glu Val Pro Gln Ser His
            20                  25                  30

Gly Ile Arg Val Thr Gly Tyr Phe Gln Cys Asn Glu Arg Pro Lys Ser
        35                  40                  45

Lys Lys Thr Leu His Ser Phe Ala Val Lys Leu Cys Asp Ala Ile Lys
    50                  55                  60

Pro Val Arg Ala Asp Ala Pro Ser Leu Lys Ile Ala Ile Trp Thr Ala
65                  70                  75                  80

Leu Asp Leu Ala Phe Val Lys Pro Pro Asn Gly Thr Val Thr Ile Asp
                85                  90                  95

Ala Ala Val Lys Ala Thr Pro Leu Ile Gly Asn Thr Gln Tyr Thr Val
            100                 105                 110

Gly Asp Glu Ile Phe Gln Met Leu Gly Arg Arg Gly Gly Leu Ile Val
        115                 120                 125

Ile Arg Asn Leu Pro His Asp Tyr Pro Arg Thr Leu Ile Glu Phe Ala
    130                 135                 140

Ser Pro Glu Pro
145


<210> SEQ ID NO 6
<211> LENGTH: 704
<212> TYPE: PRT
<213> ORGANISM: Farmington rhabdovirus

<400> SEQUENCE: 6

Met Leu Arg Ile Gln Ile Pro Pro Ile Ala Ile Ile Leu Val Ser Leu
1               5                   10                  15

Leu Thr Leu Asp Leu Ser Gly Ala Arg Arg Thr Thr Thr Gln Arg Ile
            20                  25                  30

Pro Leu Leu Asn Asp Ser Trp Asp Leu Phe Ser Ser Tyr Gly Asp Ile
        35                  40                  45
```

```
Pro Glu Glu Leu Val Val Tyr Gln Asn Tyr Ser His Asn Ser Ser Glu
    50                  55                  60

Leu Pro Pro Pro Gly Phe Glu Arg Trp Tyr Ile Asn Arg Arg Val Ala
65                  70                  75                  80

Asp Thr Ser Ile Pro Cys Arg Gly Pro Cys Leu Val Pro Tyr Ile Leu
                85                  90                  95

His Gly Leu Asn Asp Thr Thr Val Ser Arg Arg Gly Gly Gly Trp Arg
            100                 105                 110

Arg Ser Gly Met Lys Tyr Pro Thr His Ala Val Arg Leu Gly Pro Ser
        115                 120                 125

Thr Asp Asp Glu Arg Val Glu Glu Asp Ile Gly Tyr Val Asn Val Ser
    130                 135                 140

Ala Leu Ser Cys Thr Gly Ser Pro Val Glu Met Ala Ile Pro Thr Ile
145                 150                 155                 160

Pro Asp Cys Thr Ser Ala Ile His Pro Arg Ser Glu Val Thr Val Pro
                165                 170                 175

Val Lys Leu Asp Val Met Arg Arg Asn Pro Asn Tyr Pro Pro Ile Arg
            180                 185                 190

Ala Trp Ser Cys Ile Gly Gln Lys Ile Thr Asn Arg Cys Asp Trp Ala
        195                 200                 205

Leu Phe Gly Glu Asn Leu Ile Tyr Thr Gln Val Glu Ala Ser Ser Leu
    210                 215                 220

Ala Phe Lys His Thr Arg Ala Ser Leu Leu Asn Glu Ser Asn Gly Ile
225                 230                 235                 240

Asp Ala Glu Gly Arg Ala Val Pro Tyr Ile Leu Gly Asp Ile Glu Pro
                245                 250                 255

Gly Tyr Cys Arg Thr Leu Phe Asn Thr Trp Val Ser Ser Glu Ile Val
            260                 265                 270

Ser Cys Thr Pro Ile Glu Leu Val Leu Val Asp Leu Asn Pro Leu Ser
        275                 280                 285

Pro Gly His Gly Gly Tyr Ala Val Leu Leu Pro Asn Gly Asp Lys Val
    290                 295                 300

Asp Val His Asp Lys His Ala Trp Asp Gly Asp Asn Lys Met Trp Arg
305                 310                 315                 320

Trp Val Tyr Glu Lys Lys Asp Pro Cys Ala Phe Glu Leu Val Ser Arg
                325                 330                 335

Glu Val Cys Leu Phe Ser Leu Ser Arg Gly Ser Arg Leu Arg Gly Ala
            340                 345                 350

Thr Pro Pro Gln Gly Glu Leu Leu Thr Cys Pro His Ser Gly Lys Ala
        355                 360                 365

Phe Asp Leu Lys Gly Ala Arg Arg Ile Thr Pro Ile Ser Cys Lys Ile
    370                 375                 380

Asp Met Glu Tyr Asp Leu Leu Ser Leu Pro Thr Gly Val Ile Leu Gly
385                 390                 395                 400

Leu His Leu Ser Glu Leu Gly Thr Ser Phe Gly Asn Leu Ser Met Ser
                405                 410                 415

Leu Glu Met Tyr Glu Pro Ala Thr Thr Leu Thr Pro Glu Gln Ile Asn
            420                 425                 430

Phe Ser Leu Lys Glu Leu Gly Ser Trp Thr Glu Ala Gln Leu Lys Ser
        435                 440                 445

Leu Ser His Ser Ile Cys Leu Ser Thr Phe Ser Ile Trp Glu Leu Ser
    450                 455                 460

Val Gly Met Ile Asp Leu Asn Pro Thr Arg Ala Ala Arg Ala Leu Leu
```

```
465                 470                 475                 480

His Asp Asp Asn Ile Leu Ala Thr Phe Glu Asn Gly His Phe Ser Ile
                485                 490                 495

Val Arg Cys Arg Pro Glu Ile Val Gln Val Pro Ser His Pro Arg Ala
            500                 505                 510

Cys His Met Asp Leu Arg Pro Tyr Asp Lys Gln Ser Arg Ala Ser Thr
        515                 520                 525

Leu Val Val Pro Leu Asp Asn Ser Thr Ala Leu Leu Val Pro Asp Asn
    530                 535                 540

Ile Val Val Glu Gly Val Glu Ala Ser Leu Cys Asn His Ser Val Ala
545                 550                 555                 560

Ile Thr Leu Ser Lys Asn Arg Thr His Ser Tyr Ser Leu Tyr Pro Gln
                565                 570                 575

Gly Arg Pro Val Leu Arg Gln Lys Gly Ala Val Glu Leu Pro Thr Ile
            580                 585                 590

Gly Pro Leu Gln Leu His Pro Ala Thr Arg Val Asp Leu Tyr Thr Leu
        595                 600                 605

Lys Glu Phe Gln Glu Asp Arg Ile Ala Arg Ser Arg Val Thr Asp Ile
    610                 615                 620

Lys Ala Ala Val Asp Asp Leu Arg Ala Lys Trp Arg Lys Gly Lys Phe
625                 630                 635                 640

Glu Ala Asp Thr Thr Gly Gly Gly Leu Trp Ser Ala Ile Val Gly Val
                645                 650                 655

Phe Ser Ser Leu Gly Gly Phe Phe Met Arg Pro Leu Ile Ala Leu Ala
            660                 665                 670

Ala Ile Val Thr Ser Ile Ile Ile Leu Tyr Ile Leu Leu Arg Val Leu
        675                 680                 685

Cys Ala Ala Ser Cys Ser Thr His Arg Arg Val Arg Gln Asp Ser Trp
    690                 695                 700


<210> SEQ ID NO 7
<211> LENGTH: 2129
<212> TYPE: PRT
<213> ORGANISM: Farmington rhabdovirus

<400> SEQUENCE: 7

Met Ala Phe Asp Pro Asn Trp Gln Arg Glu Gly Tyr Glu Trp Asp Pro
1               5                   10                  15

Ser Ser Glu Gly Arg Pro Thr Asp Glu Asn Glu Asp Asp Arg Gly His
            20                  25                  30

Arg Pro Lys Thr Arg Leu Arg Thr Phe Leu Ala Arg Thr Leu Asn Ser
        35                  40                  45

Pro Ile Arg Ala Leu Phe Tyr Thr Ile Phe Leu Gly Ile Arg Ala Val
    50                  55                  60

Trp Asp Gly Phe Lys Arg Leu Leu Pro Val Arg Thr Glu Lys Gly Tyr
65                  70                  75                  80

Ala Arg Phe Ser Glu Cys Val Thr Tyr Gly Met Ile Gly Cys Asp Glu
                85                  90                  95

Cys Val Ile Asp Pro Val Arg Val Val Ile Glu Leu Thr Glu Met Gln
            100                 105                 110

Leu Pro Ile Lys Gly Lys Gly Ser Thr Arg Leu Arg Ala Met Ile Thr
        115                 120                 125

Glu Asp Leu Leu Thr Gly Met Arg Thr Ala Val Pro Gln Ile Arg Val
    130                 135                 140
```

```
Arg Ser Lys Ile Leu Ala Glu Arg Leu Gly Arg Ala Ile Gly Arg Glu
145                 150                 155                 160

Thr Leu Pro Ala Met Ile His His Glu Trp Ala Phe Val Met Gly Lys
                165                 170                 175

Ile Leu Thr Phe Met Ala Asp Asn Val Gly Met Asn Ala Asp Thr Val
            180                 185                 190

Glu Gly Val Leu Ser Leu Ser Glu Val Thr Arg Arg Trp Asp Ile Gly
        195                 200                 205

Asn Ser Val Ser Ala Val Phe Asn Pro Asp Gly Leu Thr Ile Arg Val
    210                 215                 220

Glu Asn Thr Gly Tyr Ile Met Thr Arg Glu Thr Ala Cys Met Ile Gly
225                 230                 235                 240

Asp Ile His Ala Gln Phe Ala Ile Gln Tyr Leu Ala Ala Tyr Leu Asp
                245                 250                 255

Glu Val Ile Gly Thr Arg Thr Ser Leu Ser Pro Ala Glu Leu Thr Ser
            260                 265                 270

Leu Lys Leu Trp Gly Leu Asn Val Leu Lys Leu Leu Gly Arg Asn Gly
        275                 280                 285

Tyr Glu Val Ile Ala Cys Met Glu Pro Ile Gly Tyr Ala Val Leu Met
    290                 295                 300

Met Gly Arg Asp Arg Ser Pro Asp Pro Tyr Val Asn Asp Thr Tyr Leu
305                 310                 315                 320

Asn Ser Ile Leu Ser Glu Phe Pro Val Asp Ser Asp Ala Arg Ala Cys
                325                 330                 335

Val Glu Ala Leu Leu Thr Ile Tyr Met Ser Phe Gly Thr Pro His Lys
            340                 345                 350

Val Ser Asp Ala Phe Gly Leu Phe Arg Met Leu Gly His Pro Met Val
        355                 360                 365

Asp Gly Ala Asp Gly Ile Glu Lys Met Arg Arg Leu Ser Lys Lys Val
    370                 375                 380

Lys Ile Pro Asp Gln Ser Thr Ala Ile Asp Leu Gly Ala Ile Met Ala
385                 390                 395                 400

Glu Leu Phe Val Arg Ser Phe Val Lys Lys His Lys Arg Trp Pro Asn
                405                 410                 415

Cys Ser Ile Asn Leu Pro Pro Arg His Pro Phe His His Ala Arg Leu
            420                 425                 430

Cys Gly Tyr Val Pro Ala Glu Thr His Pro Leu Asn Asn Thr Ala Ser
        435                 440                 445

Trp Ala Ala Val Glu Phe Asn Gln Glu Phe Glu Pro Pro Arg Gln Tyr
    450                 455                 460

Asn Leu Ala Asp Ile Ile Asp Asp Lys Ser Cys Ser Pro Asn Lys His
465                 470                 475                 480

Glu Leu Tyr Gly Ala Trp Met Lys Ser Lys Thr Ala Gly Trp Gln Glu
                485                 490                 495

Gln Lys Lys Leu Ile Leu Arg Trp Phe Thr Glu Thr Met Val Lys Pro
            500                 505                 510

Ser Glu Leu Leu Glu Glu Ile Asp Ala His Gly Phe Arg Glu Glu Asp
        515                 520                 525

Lys Leu Ile Gly Leu Thr Pro Lys Glu Arg Glu Leu Lys Leu Thr Pro
    530                 535                 540

Arg Met Phe Ser Leu Met Thr Phe Lys Phe Arg Thr Tyr Gln Val Leu
545                 550                 555                 560

Thr Glu Ser Met Val Ala Asp Glu Ile Leu Pro His Phe Pro Gln Ile
```

```
                565                 570                 575

Thr Met Thr Met Ser Asn His Glu Leu Thr Lys Arg Leu Ile Ser Arg
            580                 585                 590

Thr Arg Pro Gln Ser Gly Gly Gly Arg Asp Val His Ile Thr Val Asn
        595                 600                 605

Ile Asp Phe Gln Lys Trp Asn Thr Asn Met Arg His Gly Leu Val Lys
    610                 615                 620

His Val Phe Glu Arg Leu Asp Asn Leu Phe Gly Phe Thr Asn Leu Ile
625                 630                 635                 640

Arg Arg Thr His Glu Tyr Phe Gln Glu Ala Lys Tyr Tyr Leu Ala Glu
                645                 650                 655

Asp Gly Thr Asn Leu Ser Phe Asp Arg Asn Gly Glu Leu Ile Asp Gly
            660                 665                 670

Pro Tyr Val Tyr Thr Gly Ser Tyr Gly Gly Asn Glu Gly Leu Arg Gln
        675                 680                 685

Lys Pro Trp Thr Ile Val Thr Val Cys Gly Ile Tyr Lys Val Ala Arg
    690                 695                 700

Asp Leu Lys Ile Lys His Gln Ile Thr Gly Gln Gly Asp Asn Gln Val
705                 710                 715                 720

Val Thr Leu Ile Phe Pro Asp Arg Glu Leu Pro Ser Asp Pro Val Glu
                725                 730                 735

Arg Ser Lys Tyr Cys Arg Asp Lys Ser Ser Gln Phe Leu Thr Arg Leu
            740                 745                 750

Ser Gln Tyr Phe Ala Glu Val Gly Leu Pro Val Lys Thr Glu Glu Thr
        755                 760                 765

Trp Met Ser Ser Arg Leu Tyr Ala Tyr Gly Lys Arg Met Phe Leu Glu
    770                 775                 780

Gly Val Pro Leu Lys Met Phe Leu Lys Lys Ile Gly Arg Ala Phe Ala
785                 790                 795                 800

Leu Ser Asn Glu Phe Val Pro Ser Leu Glu Glu Asp Leu Ala Arg Val
                805                 810                 815

Trp Ser Ala Thr Ser Ala Ala Val Glu Leu Asp Leu Thr Pro Tyr Val
            820                 825                 830

Gly Tyr Val Leu Gly Cys Cys Leu Ser Ala Gln Ala Ile Arg Asn His
        835                 840                 845

Leu Ile Tyr Ser Pro Val Leu Glu Gly Pro Leu Leu Val Lys Ala Tyr
    850                 855                 860

Glu Arg Lys Phe Ile Asn Tyr Asp Gly Gly Thr Lys Arg Gly Ala Met
865                 870                 875                 880

Pro Gly Leu Arg Pro Thr Phe Glu Ser Leu Val Lys Ser Ile Cys Trp
                885                 890                 895

Lys Pro Lys Ala Ile Gly Gly Trp Pro Val Leu Met Leu Glu Asp Leu
            900                 905                 910

Ile Ile Lys Gly Phe Pro Asp Pro Ala Thr Ser Ala Leu Ala Gln Leu
        915                 920                 925

Lys Ser Met Val Pro Tyr Thr Ser Gly Ile Asp Arg Glu Ile Ile Leu
    930                 935                 940

Ser Cys Leu Asn Leu Pro Leu Ser Ser Val Val Ser Pro Ser Met Leu
945                 950                 955                 960

Leu Lys Asp Pro Ala Ala Ile Asn Thr Ile Thr Thr Pro Ser Ala Gly
                965                 970                 975

Asp Ile Leu Gln Glu Val Ala Arg Asp Tyr Val Thr Asp Tyr Pro Leu
            980                 985                 990
```

```
Gln Asn Pro Gln Leu Arg Ala Val  Val Lys Asn Val Lys  Thr Glu Leu
        995                  1000                 1005

Asp Thr  Leu Ala Ser Asp Leu  Phe Lys Cys Glu Pro  Phe Phe Pro
    1010                 1015                 1020

Pro Leu  Met Ser Asp Ile Phe  Ser Ala Ser Leu Pro  Ala Tyr Gln
    1025                 1030                 1035

Asp Arg  Ile Val Arg Lys Cys  Ser Thr Thr Ser Thr  Ile Arg Arg
    1040                 1045                 1050

Lys Ala  Ala Glu Arg Gly Ser  Asp Ser Leu Leu Asn  Arg Met Lys
    1055                 1060                 1065

Arg Asn  Glu Ile Asn Lys Met  Met Leu His Leu Trp  Ala Thr Trp
    1070                 1075                 1080

Gly Arg  Ser Pro Leu Ala Arg  Leu Asp Thr Arg Cys  Leu Thr Thr
    1085                 1090                 1095

Cys Thr  Lys Gln Leu Ala Gln  Gln Tyr Arg Asn Gln  Ser Trp Gly
    1100                 1105                 1110

Lys Gln  Ile His Gly Val Ser  Val Gly His Pro Leu  Glu Leu Phe
    1115                 1120                 1125

Gly Arg  Ile Thr Pro Ser His  Arg Cys Leu His Glu  Glu Asp His
    1130                 1135                 1140

Gly Asp  Phe Leu Gln Thr Phe  Ala Ser Glu His Val  Asn Gln Val
    1145                 1150                 1155

Asp Thr  Asp Ile Thr Thr Thr  Leu Gly Pro Phe Tyr  Pro Tyr Ile
    1160                 1165                 1170

Gly Ser  Glu Thr Arg Glu Arg  Ala Val Lys Val Arg  Lys Gly Val
    1175                 1180                 1185

Asn Tyr  Val Val Glu Pro Leu  Leu Lys Pro Ala Val  Arg Leu Leu
    1190                 1195                 1200

Arg Ala  Ile Asn Trp Phe Ile  Pro Glu Glu Ser Asp  Ala Ser His
    1205                 1210                 1215

Leu Leu  Ser Asn Leu Leu Ala  Ser Val Thr Asp Ile  Asn Pro Gln
    1220                 1225                 1230

Asp His  Tyr Ser Ser Thr Glu  Val Gly Gly Gly Asn  Ala Val His
    1235                 1240                 1245

Arg Tyr  Ser Cys Arg Leu Ser  Asp Lys Leu Ser Arg  Val Asn Asn
    1250                 1255                 1260

Leu Tyr  Gln Leu His Thr Tyr  Leu Ser Val Thr Thr  Glu Arg Leu
    1265                 1270                 1275

Thr Lys  Tyr Ser Arg Gly Ser  Lys Asn Thr Asp Ala  His Phe Gln
    1280                 1285                 1290

Ser Met  Met Ile Tyr Ala Gln  Ser Arg His Ile Asp  Leu Ile Leu
    1295                 1300                 1305

Glu Ser  Leu His Thr Gly Glu  Met Val Pro Leu Glu  Cys His His
    1310                 1315                 1320

His Ile  Glu Cys Asn His Cys  Ile Glu Asp Ile Pro  Asp Glu Pro
    1325                 1330                 1335

Ile Thr  Gly Asp Pro Ala Trp  Thr Glu Val Lys Phe  Pro Ser Ser
    1340                 1345                 1350

Pro Gln  Glu Pro Phe Leu Tyr  Ile Arg Gln Gln Asp  Leu Pro Val
    1355                 1360                 1365

Lys Asp  Lys Leu Glu Pro Val  Pro Arg Met Asn Ile  Val Arg Leu
    1370                 1375                 1380
```

```
Ala Gly  Leu Gly Pro Glu Ala  Ile Ser Glu Leu Ala  His Tyr Phe
    1385                 1390                 1395

Val Ala  Phe Arg Val Ile Arg  Ala Ser Glu Thr Asp  Val Asp Pro
    1400                 1405                 1410

Asn Asp  Val Leu Ser Trp Thr  Trp Leu Ser Arg Ile  Asp Pro Asp
    1415                 1420                 1425

Lys Leu  Val Glu Tyr Ile Val  His Val Phe Ala Ser  Leu Glu Trp
    1430                 1435                 1440

His His  Val Leu Met Ser Gly  Val Ser Val Ser Val  Arg Asp Ala
    1445                 1450                 1455

Phe Phe  Lys Met Leu Val Ser  Lys Arg Ile Ser Glu  Thr Pro Leu
    1460                 1465                 1470

Ser Ser  Phe Tyr Tyr Leu Ala  Asn Leu Phe Val Asp  Pro Gln Thr
    1475                 1480                 1485

Arg Glu  Ala Leu Met Ser Ser  Lys Tyr Gly Phe Ser  Pro Pro Ala
    1490                 1495                 1500

Glu Thr  Val Pro Asn Ala Asn  Ala Ala Ala Ala Glu  Ile Arg Arg
    1505                 1510                 1515

Cys Cys  Ala Asn Ser Ala Pro  Ser Ile Leu Glu Ser  Ala Leu His
    1520                 1525                 1530

Ser Arg  Glu Val Val Trp Met  Pro Gly Thr Asn Asn  Tyr Gly Asp
    1535                 1540                 1545

Val Val  Ile Trp Ser His Tyr  Ile Arg Leu Arg Phe  Ser Glu Val
    1550                 1555                 1560

Lys Leu  Val Asp Ile Thr Arg  Tyr Gln Gln Trp Trp  Arg Gln Ser
    1565                 1570                 1575

Glu Arg  Asp Pro Tyr Asp Leu  Val Pro Asp Met Gln  Val Leu Glu
    1580                 1585                 1590

Ser Asp  Leu Asp Thr Leu Met  Lys Arg Ile Pro Arg  Leu Met Arg
    1595                 1600                 1605

Lys Ala  Arg Arg Pro Pro Leu  Gln Val Ile Arg Glu  Asp Leu Asp
    1610                 1615                 1620

Val Ala  Val Ile Asn Ala Asp  His Pro Ala His Ser  Val Leu Gln
    1625                 1630                 1635

Asn Lys  Tyr Arg Lys Leu Ile  Phe Arg Glu Pro Lys  Ile Ile Thr
    1640                 1645                 1650

Gly Ala  Val Tyr Lys Tyr Leu  Ser Leu Lys Ser Glu  Leu Thr Glu
    1655                 1660                 1665

Phe Thr  Ser Ala Met Val Ile  Gly Asp Gly Thr Gly  Gly Ile Thr
    1670                 1675                 1680

Ala Ala  Met Met Ala Asp Gly  Ile Asp Val Trp Tyr  Gln Thr Leu
    1685                 1690                 1695

Val Asn  Tyr Asp His Val Thr  Gln Gln Gly Leu Ser  Val Gln Ala
    1700                 1705                 1710

Pro Ala  Ala Leu Asp Leu Leu  Arg Gly Ala Pro Ser  Gly Arg Leu
    1715                 1720                 1725

Leu Asn  Pro Gly Arg Phe Ala  Ser Phe Gly Ser Asp  Leu Thr Asp
    1730                 1735                 1740

Pro Arg  Phe Thr Ala Tyr Phe  Asp Gln Tyr Pro Pro  Phe Lys Val
    1745                 1750                 1755

Asp Thr  Leu Trp Ser Asp Ala  Glu Gly Asp Phe Trp  Asp Lys Pro
    1760                 1765                 1770

Ser Lys  Leu Asn Gln Tyr Phe  Glu Asn Ile Ile Ala  Leu Arg His
```

```
    1775                1780                1785

Arg Phe  Val Lys Thr Asn Gly  Gln Leu Val Val Lys  Val Tyr Leu
    1790                1795                1800

Thr Gln  Asp Thr Ala Thr Thr  Ile Glu Ala Phe Arg  Lys Lys Leu
    1805                1810                1815

Ser Pro  Cys Ala Ile Ile Val  Ser Leu Phe Ser Thr  Glu Gly Ser
    1820                1825                1830

Thr Glu  Cys Phe Val Leu Ser  Asn Leu Ile Ala Pro  Asp Thr Pro
    1835                1840                1845

Val Asp  Leu Glu Met Val Glu  Asn Ile Pro Lys Leu  Thr Ser Leu
    1850                1855                1860

Val Pro  Gln Arg Thr Thr Val  Lys Cys Tyr Ser Arg  Arg Val Ala
    1865                1870                1875

Cys Ile  Ser Lys Arg Trp Gly  Leu Phe Arg Ser Pro  Ser Ile Ala
    1880                1885                1890

Leu Glu  Val Gln Pro Phe Leu  His Tyr Ile Thr Lys  Val Ile Ser
    1895                1900                1905

Asp Lys  Gly Thr Gln Leu Ser  Leu Met Ala Val Ala  Asp Thr Met
    1910                1915                1920

Ile Asn  Ser Tyr Lys Lys Ala  Ile Ser Pro Arg Val  Phe Asp Leu
    1925                1930                1935

His Arg  His Arg Ala Ala Leu  Gly Phe Gly Arg Arg  Ser Leu His
    1940                1945                1950

Leu Ile  Trp Gly Met Ile Ile  Ser Pro Ile Ala Tyr  Gln His Phe
    1955                1960                1965

Glu Asn  Pro Ala Lys Leu Met  Asp Val Leu Asp Met  Leu Thr Asn
    1970                1975                1980

Asn Ile  Ser Ala Phe Leu Ser  Ile Ser Ser Ser Gly  Phe Asp Leu
    1985                1990                1995

Ser Phe  Ser Val Ser Ala Asp  Arg Asp Val Arg Ile  Asp Ser Lys
    2000                2005                2010

Leu Val  Arg Leu Pro Leu Phe  Glu Gly Ser Asp Leu  Lys Phe Met
    2015                2020                2025

Lys Thr  Ile Met Ser Thr Leu  Gly Ser Val Phe Asn  Gln Val Glu
    2030                2035                2040

Pro Phe  Lys Gly Ile Ala Ile  Asn Pro Ser Lys Leu  Met Thr Val
    2045                2050                2055

Lys Arg  Thr Gln Glu Leu Arg  Tyr Asn Asn Leu Ile  Tyr Thr Lys
    2060                2065                2070

Asp Ala  Ile Leu Phe Pro Asn  Glu Ala Ala Lys Asn  Thr Ala Pro
    2075                2080                2085

Leu Arg  Ala Asn Met Val Tyr  Pro Val Arg Gly Asp  Leu Phe Ala
    2090                2095                2100

Pro Thr  Asp Arg Ile Pro Ile  Met Thr Leu Val Ser  Asp Glu Thr
    2105                2110                2115

Thr Pro  Gln His Ser Pro Pro  Glu Asp Glu Ala
    2120                2125
```

<210> SEQ ID NO 8
<211> LENGTH: 1236
<212> TYPE: DNA
<213> ORGANISM: Farmington rhabdovirus

<400> SEQUENCE: 8

```
atggctcgtc cgctagctgc tgcgcaacat ctcataaccg agcgtcattc ccttcaggcg     60

actctgtcgc gggcgtccaa gaccagagcc gaggaattcg tcaaagattt ctaccttcaa    120

gagcagtatt ctgtcccgac catcccgacg gacgacattg cccagtctgg gcccatgctg    180

cttcaggcca tcctgagcga ggaatacaca aaggccactg acatagccca atccatcctc    240

tggaacactc ccacacccaa cgggctcctc agagagcatc tagatgccga tgggggaggc    300

tcattcacag cgctgcccgc gtctgcaatc agacccagcg acgaggcgaa tgcatgggcc    360

gctcgcatct ccgactcagg gttggggcct gtcttctatg cagccctcgc tgcttacatc    420

atcggctggt caggaagagg agagactagc cgcgtgcagc agaacatagg tcagaaatgg    480

ctgatgaacc tgaacgcaat cttcggcacc acgatcaccc atccaacaac cgtgcgtctg    540

ccaatcaacg tcgtcaacaa cagcctcgca gtgaggaacg gacttgctgc cacactctgg    600

ctatactacc gttcatcacc tcagagtcag gacgcgttct tctatgggct catccgtccc    660

tgttgcagtg gatatctcgg cctgctacat cgggtgcagg agattgatga gatggagccg    720

gacttcctca gtgacccccg gatcatccag gtgaatgagg tctacagtgc actcagagcc    780

ctggttcaac tgggaaacga cttcaagacc gccgatgatg agcccatgca ggtctgggcg    840

tgcaggggaa tcaacaacgg atatctgaca tatctctcag aaactcctgc gaagaaagga    900

gctgttgtgc ttatgtttgc ccaatgcatg ctgaagggcg actctgaggc ctggaacagc    960

taccgcactg caacctgggt gatgccctat tgcgacaatg tggccctagg agcgatggca   1020

ggctacatcc aagcccgcca gaacaccagg gcatatgagg tctcagccca gacaggtctc   1080

gacgtcaaca tggccgcggt caaggacttt gaggccagtt caaaacccaa ggctgctcca   1140

atctcgctga tcccacgccc cgctgatgtc gcatcccgca cctctgagcg cccatctatt   1200

cctgaggttg acagcgacga agagctcgga ggaatg                              1236
```

<210> SEQ ID NO 9
<211> LENGTH: 948
<212> TYPE: DNA
<213> ORGANISM: Farmington rhabdovirus

<400> SEQUENCE: 9

```
atggaggact atttgtctag cttagaggcc gcgagagagc tcgtccggac ggagctggag     60

cccaagcgta acctcatagc cagcttagag tccgacgatc ccgatccggt aatagcgcca    120

gcggtaaaac caaaacatcc caagccatgc ctgagcacta aagaagagga tcatctcccc    180

tctcttcgcc tactattcgg cgcaaaacga gacacctcgg tgggcgtaga gcagactctc    240

cacaagcgtc tctgcgcttg tctcgacggt tacctgacca tgacgaagaa agaggccaat    300

gcctttaagg ccgcggctga agcagcagca ttagcagtca tggacattaa gatggagcat    360

cagcgccagg atctagagga tctgaccgct gctatcccta ggatagaatt caaactcaat    420

gccatcctgg aaaacaacaa ggagatagcc aaggctgtaa ctgctgctaa ggagatggag    480

cgggagatgt cgtgggggga aagcgccgcc agctcgctca agtctgtcac cctagatgag    540

tcgtttaggg gccctgaaga gctttcagag tcatttggca tccgatataa ggtcagaacc    600

tggaatgagt tcaagaaggc gctggaaacc agcattgtgg acctgaggcc tagccctgtt    660

tcatttaggg aattacggac tatgtggctg tctcttgaca cctcctttag gctcattggg    720

tttgccttca ttcccacatg cgagcgcctg gagaccaaag ccaaatgcaa ggagacaagg    780

actctactcc cccttgcaga gtcgatcatg cgaagatggg acctgcggga tccaaccatc    840

ttggagaaag cctgcgtagt aatgatgatc cgtgggaatg agattgcatc gctgaatcag    900
```

gtaaaagatg ttctcccgac cacaattcgt gggtggaaga tcgcttat 948

<210> SEQ ID NO 10
<211> LENGTH: 444
<212> TYPE: DNA
<213> ORGANISM: Farmington rhabdovirus

<400> SEQUENCE: 10
atgcgtcggt tctttttagg agagagcagt gcccctgcga gggactggga gtccgagcga 60 cctccccccct atgctgttga ggtccctcaa agtcacggga taagagtcac cgggtacttc 120
cagtgcaacg agcgtccgaa atccaagaag accctccaca gcttcgccgt aaaactctgc 180
gacgcaatta agccggttcg agcggatgct cccagcttga agatagcaat atggacggct 240
ctagatctgg ccttcgtgaa acctcccaat ggaactgtaa caatagatgc ggcggtgaaa 300
gctacaccgc taatcgggaa cacccagtac accgtaggcg atgaaatctt ccagatgcta 360
gggagaaggg gtggcctgat cgtcatcagg aacttacccc atgattatcc tcgaacgttg 420
attgagttcg cctctcccga gcct 444

<210> SEQ ID NO 11
<211> LENGTH: 2112
<212> TYPE: DNA
<213> ORGANISM: Farmington rhabdovirus

<400> SEQUENCE: 11
atgctcagga tccagatccc tccgattgct atcattctgg taagtctcct cacactcgac 60
ctgtccggtg caaggaggac aaccacacaa agaatccctc tccttaatga ttcgtgggat 120
ttgttctcga gctatggcga cattcccgaa gaacttgtcg tataccagaa ctacagccac 180
aattcctccg agttaccccc tcctggcttc gagagatggt acataaaccg aagagtggca 240
gacacttcca taccgtgcag ggcccctgt ctagtgccct acatccttca tggcctcaat 300
gacacaactg tctctcgacg gggaggagga tggcgaaggt ccggaatgaa gtacccaacc 360
cacgctgtca ggctaggccc ttcaacagac gacgagagag ttgaggaaga catcggctac 420
gtcaatgtct ccgcactatc ctgcacaggg tcgcccgttg agatggcgat accaacaatc 480
cccgactgca ccagtgctat ccatccacga tccgaggtta ctgtgcccgt caagctcgat 540
gtcatgagac gaaatcccaa ctaccctccc attagagcgt ggtcgtgcat cggacagaaa 600
atcaccaacc gatgtgattg ggcactcttc ggcgagaacc tcatatatac tcaagttgaa 660
gctagctctc tagcattcaa gcacacaaga gcctctcttt tgaacgaatc caacgggata 720
gacgctgaag gacgtgcagt tccctatatc ctcggggata tcgaacccgg gtactgccga 780
accctattca acacatgggt ctctagtgag atcgtgtcat gcacgcccat cgaacttgtc 840
ctagttgacc tgaacccttt gtccccggga catggcggat atgctgtatt gctgccaaac 900
ggagacaaag tggatgtaca cgacaagcat gcatgggatg ggacaacaa aatgtggaga 960 tgggtgtacg agaagaaaga tccctgtgcg ttcgagctgg tatccaggga agtgtgtctt 1020
ttctcactga gtaggggtag tagactgaga ggagcaaccc ctccccaagg agagctcctc 1080
acctgcccgc attcgggaaa ggcatttgac ctgaaggggg cccgaaggat tacacccatt 1140
tcatgcaaaa tcgacatgga atatgacttg ctgtcactac caaccggagt catcctaggc 1200
ctccacctat cagaactcgg gacctccttt ggcaacctct caatgagtct tgaaatgtat 1260
gaacctgcca caactctgac ccctgagcaa atcaacttct cgcttaaaga gctgggaagc 1320

```
tggaccgagg ctcaactgaa gagcctgtct cactcaatct gcctctccac attctccata   1380

tgggaactat cggttgggat gatcgatcta aaccctacca gggcagcaag ggccttgctc   1440

catgatgata acatactggc aacattcgag aacggtcact tttccatcgt cagatgtcgt   1500

ccggaaatag ttcaagtccc ttcgcatcct cgagcatgtc acatggatct ccgcccttat   1560

gacaagcaat cacgggcatc aaccctggtg gttccccttg acaacagcac tgccctcctg   1620

gtccccgaca acatcgtggt tgaaggagta gaggccagtc tatgcaacca ctccgttgcc   1680

atcacgctgt cgaagaacag aactcactca tacagcctct atccccaggg tcgtcctgtg   1740

cttcgacaga aaggtgccgt ggagctcccg acgataggc  ccctccagtt acatcctgcc   1800

actcgagtgg acctttatac actgaaagag ttccaggagg accgaatagc gcgcagtcga   1860

gtcacagaca tcaaggctgc cgttgacgat ctgcgtgcga agtggcgtaa aggcaaattt   1920

gaggcggaca ccacgggagg gggactttgg tcggcgattg tgggagtctt cagttctctc   1980

ggggggttct tcatgaggcc cttgattgct ctcgcggcga tagtgacctc aatcatcatc   2040

ctgtatatcc ttctgcgtgt actgtgtgct gcctcatgtt cgacacaccg aagagtaagg   2100

caggactctt gg                                                       2112
```

<210> SEQ ID NO 12
<211> LENGTH: 6387
<212> TYPE: DNA
<213> ORGANISM: Farmington rhabdovirus

<400> SEQUENCE: 12

```
atggccttcg acccgaactg gcagagagaa ggttatgaat gggatccgtc aagtgagggc     60

agaccgaccg atgagaacga agacgacaga ggtcatcggc caaaaacgag acttcgtaca    120

ttccttgccc gcacgttaaa tagccctatc cgagccctat tctacacaat attcctagga    180

attcgagcgg tttgggacgg gttcaaaaga ctcctacctg tgaggaccga aaagggttat    240

gcgaggtttt ctgagtgcgt cacatatgga atgatcggat gtgatgagtg tgtaatagac    300

ccggtgaggg ttgtcattga gctgaccgag atgcagttac cgattaaagg caaaggctct    360

acgaggttga gagcaatgat aactgaagac cttctcacgg ggatgcgcac agccgtgcct    420

cagatcagag tgagatcgaa gatcctagca gagcggttag ggagagcaat cggccgagag    480

accttgccgg caatgatcca tcatgagtgg gcatttgtga tggggaagat tctcactttc    540

atggcagaca atgtgggtat gaacgctgac acggtcgagg gcgttctatc actatcagag    600

gtcacacggc gatgggatat cggcaactct gtgtccgcag tgttcaatcc tgatggcctt    660

actatcagag tagaaaacac gggttacatc atgaccagag agactgcctg catgatcgga    720

gacattcatg ctcaatttgc aatccaatac ctagctgcat acctagacga ggtgatcggc    780

acaaggacgt ctctctcacc cgccgaactg acctctctca aactatgggg acttaacgtc    840

ctgaaactcc taggacggaa cggttatgag gtgatcgcct gcatggagcc catagggtac    900

gctgtcctga tgatgggaag agacaggagt cctgatccct atgtcaatga cacctattta    960

aacagcatcc tctcagaatt ccctgtcgac tctgacgctc gagcctgcgt tgaagccctc   1020

ttaactatct atatgagctt cggcacaccc cataaagtct cggacgcatt cggcctcttc   1080

agaatgttgg gacatccgat ggttgatgga gctgacggga ttgaaaagat gcgaaggtta   1140

agcaagaagg tcaagatccc agaccagtct acagcgatcg acctcggggc tatcatggcc   1200

gaactgtttg tgcggagttt cgtaaagaag cacaaaaggt ggcccaactg ctccatcaat   1260

ctcccgccac gacacccctt ccaccacgcc cgcctatgtg ggtatgtccc ggctgaaacc   1320
```

-continued

```
catcccctaa acaacactgc atcctgggcg gctgtggagt tcaaccagga attcgagccg   1380

ccgagacagt acaaccttgc agacatcatt gatgacaagt cgtgctctcc caacaagcat   1440

gagctatatg gtgcttggat gaagtcaaaa acagctgggt ggcaggaaca aaagaagctc   1500

atactccgat ggttcactga gaccatggtt aaaccttcgg agctcctgga agagattgat   1560

gcacacggct tccgagaaga ggataagttg attggattaa caccaaagga gagagagctg   1620

aaattaacac caagaatgtt ctccttgatg acattcaagt tcagaaccta ccaagtcctc   1680

actgagagta tggtcgccga tgagatcctc ccgcacttcc cccagatcac catgaccatg   1740

tccaaccacg aactcacaaa gaggttgatt agcagaacga gacctcaatc tggaggaggg   1800

cgtgatgttc acatcaccgt gaacatagat ttccagaaat ggaacacaaa catgagacac   1860

ggactggtca aacatgtctt cgagcgactg gacaacctct ttggcttcac caacttaatc   1920

agacgaactc atgaatactt ccaggaggcg aaatactatc tggctgaaga tggaactaat   1980

ctgtcgttcg acaggaacgg ggagttaata gatggcccat acgtttacac cggatcatac   2040

gggggggaacg aggggttacg acagaagccc tggacaatag ttaccgtgtg tggaatatac   2100

aaggtagcta gagacctgaa aatcaaacat cagatcaccg gtcagggaga taatcaggtg   2160

gtcaccctaa tatttccgga tcgagagttg ccttcagatc cggtggagag gagcaagtac   2220

tgtagagaca agagcagtca gttcctgaca cgtctcagtc aatatttcgc tgaggttggt   2280

ttgcccgtca agactgaaga gacatggatg tcatcacgtc tctatgctta cggtaagcgc   2340

atgttcttag agggagttcc acttaagatg tttctcaaga agataggcag agctttcgcc   2400

ctctcgaatg agtttgtccc gtccctcgag gaagatctgg ccagagtctg gagtgccacc   2460

agcgcagcgg tagagcttga cctaactccc tacgtaggat atgtcctcgg gtgctgcttg   2520

tctgcgcagg cgatcagaaa tcacctcatc tactcccctg ttctggaggg ccctctgctg   2580

gttaaggcct acgagcgtaa gttcattaac tacgacggag gaacaaagcg gggggcgatg   2640

cccggcctac gtccaacctt tgagagccta gtcaaaagta tctgctggaa gccaaaggcc   2700

atcggagggt ggccggtatt gatgttagaa gatctcatca tcaaagggtt ccctgatccg   2760

gcgactagcg ccctggctca attgaagtca atggtgccat atacctctgg tatcgaccgg   2820

gagatcatac tttcctgtct caaccttccc ttatcgtcgg tggtatctcc gtcaatgttg   2880

ttaaaggacc cggcggccat caacaccatc acaaccccgt ccgcgggcga catcctgcaa   2940

gaggtcgcca gagactatgt taccgattac ccactccaaa acccgcagct cagagcagtg   3000

gtcaagaacg tgaagaccga gctagacaca ttggccagtg acttattcaa atgtgaacct   3060

ttctttcctc ctttaatgag cgatatcttc tcggcatctc tcccggcata tcaagacagg   3120

attgttcgca agtgctccac gacttctaca atcaggagaa aagctgccga gaggggctcc   3180

gactctctcc tcaaccggat gaaaaggaat gagatcaata agatgatgtt acatctttgg   3240

gctacctggg gaaggagccc tctggccaga ttagacacca gatgtctcac aacctgcacc   3300

aagcaattag cccaacagta tcggaaccag tcttggggaa agcagatcca tggagtctca   3360

gtcggccacc ccttagaact gttcggtcga ataacaccca gccatagatg cctacatgag   3420

gaggaccacg gagatttcct gcaaaccttc gccagcgagc atgtgaacca agtggacacc   3480

gacatcacca caactctggg gccgttctac ccttacatag gctcggagac gcgagaacgg   3540

gcagtcaagg ttcgaaaagg agtgaattac gtagttgagc cgcttctgaa acccgcagtt   3600

cgactactaa gagccattaa ttggttcatt cccgaggagt cagatgcgtc ccatttgctg   3660
```

```
agcaatctat tagcgtctgt taccgacatc aatcctcaag accactactc atctaccgaa   3720
gtaggggggg gcaacgccgt ccatcgctac agctgccgac tatccgacaa attgagcaga   3780
gtcaacaact tatatcagtt gcatacttat ttatctgtca caacagagcg gttgaccaag   3840
tacagtcgag gatcaaaaaa cactgacgca cacttccaga gcatgatgat ttatgcacaa   3900
agccgtcata tagacctcat cttggagtct ctgcacaccg gagagatggt accgttggag   3960
tgtcatcatc acattgagtg caatcactgt atagaggata tacccgacga gccaatcacg   4020
ggggacccgg cttggactga agtcaagttt ccttcaagtc ctcaggagcc ctttctttac   4080
atcaggcaac aagatctgcc ggtcaaagac aaactcgagc ctgtgcctcg catgaacatc   4140
gtccgtcttg ccggattggg tccggaggcg attagtgagc tagcgcacta ctttgttgca   4200
ttccgagtta tccgggcgtc agagacggat gtcgacccta acgatgttct ctcgtggacc   4260
tggctgagcc gaattgatcc tgacaaattg gttgagtata tcgtgcatgt gttcgcttca   4320
ctggaatggc atcatgtatt aatgtcaggc gtgagtgtga gcgtcagaga tgcattcttt   4380
aagatgctag tgtctaaaag aatctcagag actccgctaa gttcattcta ttatctggcc   4440
aacctgttcg ttgaccctca gactcgcgaa gcactaatga gctctaaata cgggttcagc   4500
ccccccgccg agacagtccc caacgcaaat gccgccgcag ccgaaataag aagatgctgt   4560
gcgaacagtg cgccgtcgat cttagaatca gcccttcaca gccgtgaggt tgtttggatg   4620
ccaggaacga acaattatgg agacgttgtc atctggtctc attacattag attacggttc   4680
agcgaagtta aactagttga cattacacga tatcagcagt ggtggagaca gtctgagcga   4740
gacccctacg atttggtccc ggacatgcag gttcttgaga gcgacctaga tacgctgatg   4800
aaacggatac cgaggctcat gcgcaaggcg agacgtcccc ctcttcaggt aattcgagag   4860
gacctggatg tcgcagtcat caatgctgat catcccgctc actctgtgct tcagaacaaa   4920
tacaggaaat tgattttcag agagccgaag attatcacgg gagctgtgta caagtacctc   4980
tccctaaaat cagagttgac agagttcacc tcagcaatgg tgatcggaga cggaactgga   5040
ggtatcaccg ccgccatgat ggccgatggg atagatgtgt ggtatcagac gctcgtcaac   5100
tatgaccacg tgacacaaca gggattatcc gtacaagccc cggcagcatt ggatcttctg   5160
cgcggggcac cctctggtag gctcttgaat ccgggaagat tcgcatcatt tgggtctgac   5220
ctaactgacc ctcgatttac agcctacttt gatcaatatc ccccgttcaa ggtggacact   5280
ctatggtctg acgcagaggg cgacttttgg gacaagcctt ccaagttgaa tcaatacttt   5340
gagaacatca ttgctttgag acatcggttc gtgaagacaa atggacagct tgtcgtgaag   5400
gtgtatctga ctcaagacac tgctaccaca attgaagcat tcagaaagaa gctgtcccca   5460
tgcgccatca tcgtgtctct cttctcgacg gaaggctcca cagaatgctt cgtcctaagc   5520
aatctcatcg caccagacac ccctgtcgac cttgagatgg tggagaatat ccctaaacta   5580
acatcccttg ttccccagag gacgacagtg aaatgctatt cccgacgagt agcgtgcatc   5640
agtaaaaggt ggggactttt cagatctccg agcatagccc ttgaagtcca accgttcctt   5700
cactacatca caaaggtcat ctcagacaaa ggaacacaac tgagtctcat ggcggtagct   5760
gacacaatga tcaacagtta caagaaggct atctcacccc gagtgttcga tctacaccgg   5820
catagggccg cactgggttt cgggaggaga tccttgcatc tcatctgggg gatgatcatc   5880
tcaccaatcg cttaccagca ttttgagaat ccggccaagt tgatggatgt cctggacatg   5940
ttgaccaata acatctcagc tttcttatcg atatcgtcgt caggatttga cctgtcattt   6000
agtgtcagtg cagaccgaga tgtccggatt gacagcaaac ttgtcagact cccgctattc   6060
```

-continued

```
gaaggatcag acctaaaatt catgaaaacc atcatgtcta ccctcggatc tgtgttcaac   6120

caggtcgagc cttttaaggg gatcgccata aacccttcta aactaatgac tgtcaagagg   6180

acacaggagt tacgttacaa caacctaatt tacactaagg atgccatcct attccccaat   6240

gaagcggcaa aaaacactgc cccgcttcga gccaacatgg tataccccgt ccggggagat   6300

ctattcgccc ctaccgatcg cataccaatc atgactctag tcagcgatga gacaacacct   6360

cagcactctc ctccagagga tgaggca                                       6387
```

COMPOSITIONS AND METHODS FOR GLIOBLASTOMA TREATMENT

CROSS REFERENCE TO RELATED APPLICATIONS

This application claims the benefit of priority of U.S. Provisional Patent Application No. 61/494,628 filed Jun. 8, 2011, which is incorporated herein by reference in its entirety.

FIELD

The present disclosure relates to rhabdoviruses and their use as an oncolytic treatment. More specifically, the present disclosure relates to Farmington rhabdovirus and its use in the treatment of glioblastoma.

BACKGROUND

This section provides background information related to the present disclosure which is not necessarily prior art.

Brain cancer is the leading cause of cancer-related death in patients younger than age 35 and accounts for roughly 10% of all cancers diagnosed in North America. Treatment of brain tumours is complicated by the fact that there are more than 120 different types, which range from low grade astrocytomas to high grade glioblastomas (GBM). Malignant gliomas, such as GBM, are by far the most common brain cancer found in adults and one of the most difficult to treat. Even with aggressive single and multimodal treatment options such as surgery, chemotherapy, radiation and small molecule inhibitors, the survival has remained unchanged over the past three decades with a median survival of less than one year after diagnosis. Reasons for the failure of conventional treatments is multifactorial including the highly infiltrative/invasive nature of GBM, limitation of drug delivery through the blood brain barrier and neural parenchyma, and genetic heterogeneity resulting in intrinsic resistance to available treatments and the rise of aggressive resistant clones. Therefore, there is a dire requirement for new treatment options, which has led to the renaissance of oncolytic viral therapy for GBM.

Currently, the efficacy and safety of several oncolytic viruses with various tumour targeting strategies are being evaluated in the lab and clinic against GBM. The rhabdovirus vesicular stomatitis virus (VSV) constitutes one of these efficacious viruses being tested preclinically. However, a desired route of viral administration for GBM is intracerebral delivery, which is not currently possible with VSV due to its neurotoxicity.

SUMMARY

It is an object of the present disclosure to obviate or mitigate at least one disadvantage of previous oncolytic viruses. For example, the oncolytic virus of the present disclosure may exhibit reduced levels of neurotoxicity.

The present technology includes systems, methods, processes, articles, and compositions that relate to rhabdoviruses, such as Farmington rhabdovirus, and related nucleotide and protein sequences thereof, and the use of such in oncolytic treatments, for example treatments for glioblastoma.

According to one aspect of the present disclosure, there is provided an isolated viral particle capable of producing a cDNA polynucleotide that includes a sequence according to SEQ ID NO: 1 when the virus is in a host cell.

According to another aspect of the present disclosure, there is provided an isolated viral particle that includes an RNA polynucleotide that includes a sequence according to SEQ ID NO: 2.

According to still another aspect of the present disclosure, there is provided an isolated viral particle having a genome that includes open reading frames that encode: a protein having a sequence comprising SEQ ID NO: 3, or a variant thereof; a protein having a sequence comprising SEQ ID NO: 4, or a variant thereof; a protein having a sequence comprising SEQ ID NO: 5, or a variant thereof; a protein having a sequence comprising SEQ ID NO: 6, or a variant thereof; and a protein having a sequence comprising SEQ ID NO: 7, or a variant thereof.

The variant of a reference protein may be a protein that has a sequence which is at least 75%, at least 80%, at least 85%, at least 90%, or at least 95% identical to the sequence of the reference protein, and where the variant protein maintains the same biological function as the reference protein.

In some examples, at least one of the open reading frames encodes a protein having a sequence which is a sequence selected from the group consisting of SEQ ID NOs: 3, 4, 5, 6, and 7. In such examples, the variant of a reference protein may be a protein having a sequence which is at least 50%, at least 55%, at least 60%, at least 65%, at least 70%, at least 75%, at least 80%, at least 85%, at least 90%, or at least 95% identical to the sequence of the reference protein, and where the variant protein maintains the same biological function as the reference protein.

The viral genome may include open reading frames that encode: a protein having a sequence comprising SEQ ID NO: 3; a protein having a sequence comprising SEQ ID NO: 4; a protein having a sequence comprising SEQ ID NO: 5; a protein having a sequence comprising SEQ ID NO: 6; and a protein having a sequence comprising SEQ ID NO: 7.

The isolated viral particle may further include at least one additional open reading frame for encoding at least one additional protein. The additional protein may be an immunogenic protein.

According to another aspect of the present disclosure, there is provided an isolated viral particle capable of producing a cDNA polynucleotide when the virus is in a host cell, the cDNA polynucleotide having a sequence that includes: SEQ ID NO: 8, or a conservative variant thereof; SEQ ID NO: 9, or a conservative variant thereof; SEQ ID NO: 10, or a conservative variant thereof; SEQ ID NO: 11, or a conservative variant thereof; SEQ ID NO: 12, or a conservative variant thereof; and promoters thereof.

The conservative variant of a sequence of nucleotides may be a sequence that is at least 75%, at least 80%, at least 85%, at least 90%, or at least 95% identical to the reference sequence of nucleotides. The conservative variant may be a sequence comprising one or more silent substitutions.

According to still another aspect of the present disclosure, an isolated viral particle according to the present disclosure may be used for the treatment of cancer. The cancer may be a brain cancer. The brain cancer may be a glioblastoma. The isolated viral particle may be used to infect a cell where the infected cell is for the treatment of cancer.

According to still another aspect of the present disclosure, an isolated viral particle according to the present disclosure may be used for inducing an immunogenic response in a person administered the virus. The immunogenic response may be an anti-cancer response. The isolated viral particle may be used to infect a cell where the infected cell is use to generate the immunogenic response.

The isolated viral particle may be formulated for direct delivery to the central nervous system, outside the blood/brain barrier, inside the blood/brain barrier, or any combination thereof. The isolated viral particle may be formulated for administration via intrathecal, intravenous or intracranial injection.

The infected cell may be formulated for direct delivery to the central nervous system, outside the blood/brain barrier, inside the blood/brain barrier, or any combination thereof. The infected cell may be formulated for administration via intrathecal, intravenous or intracranial injection.

According to still another aspect of the present disclosure, there is provided a method for treating cancer comprising administering an isolated viral particle according to the present disclosure to a patient having cancer. The cancer may be a brain cancer. The brain cancer may be a glioblastoma.

The isolated viral particle may be administered to the patient directly. For example, the isolated viral particle may be administered directly to the central nervous system, outside the blood/brain barrier, inside the blood/brain barrier, or any combination thereof. The isolated viral particle may be administered to the patient intrathecally, intravenously or via intracranial injection.

Alternatively, a cell may be infected with the isolated viral particle and the infected cell may be administered to the patient. The infected cell may be administered directly to the central nervous system, outside the blood/brain barrier, inside the blood/brain barrier, or any combination thereof. The infected cell may be administered to the patient intrathecally, intravenously or via intracranial injection.

According to still another aspect of the present disclosure, there is provided a method for inducing an immunogenic response in a patient, the method including administering an isolated viral particle according to the present disclosure to the patient.

The isolated viral particle may be administered to the patient directly. For example, the isolated viral particle may be administered directly to the central nervous system, outside the blood/brain barrier, inside the blood/brain barrier, or any combination thereof. The isolated viral particle may be administered to the patient intrathecally, intravenously or via intracranial injection.

Alternatively, a cell may be infected with the isolated viral particle and the infected cell may be administered to the patient. The infected cell may be administered directly to the central nervous system, outside the blood/brain barrier, inside the blood/brain barrier, or any combination thereof. The infected cell may be administered to the patient intrathecally, intravenously or via intracranial injection.

According to a yet further aspect of the present disclosure, there is provided a kit for the treatment of cancer in a patient, the kit including: the isolated viral particle according to the present disclosure; and instructions for administration of the isolated viral particle to the patient.

The cancer may be a brain cancer. The brain cancer may be a glioblastoma.

The isolated viral particle may be formulated for direct delivery to the central nervous system, outside the blood/brain barrier, inside the blood/brain barrier, or any combination thereof. The isolated viral particle may be formulated for administration via intrathecal, intravenous or intracranial injection.

Alternatively, the isolated viral particle may be formulated for infection of a cell where the cell is for delivery to the central nervous system, outside the blood/brain barrier, inside the blood/brain barrier, or any combination thereof. The cell may be for administration via intrathecal, intravenous or intracranial injection.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

FIG. 7. Novel Mechanism of Tumor Targeting: A) Viral titer determined in Teratocarcinoma and differentiated NT2 cells infected with the indicated viruses; B) Teratocarcinoma and differentiated NT2 cells infected with the indicated viruses and assayed for viability using Alamar blue metabolic dye; C) Western blot of several components of the cellular apoptotic signaling cascade following infection of either tumour (SNB19 or normal cells (NHA); D. Schematic of cellular apoptosis signaling cascade.

DESCRIPTION

Definitions

Figure 1E:
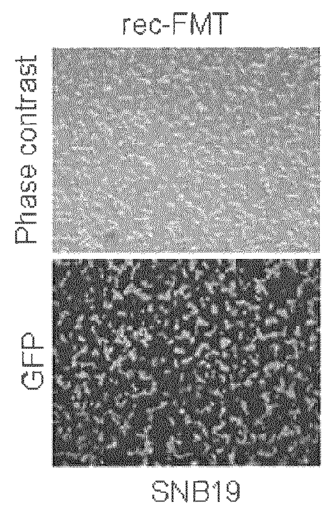
FIG. 1. Introduction to FMT Virus: A) Region isolated; B) Amino Acid Blast alignment of 5 FMT putative open reading frames (ORFs) (N, P, G, M and L) reveals little sequence homology to known sequences in the NCBI database; C) SDS PAGE gel of FMT virus showing 4 of the 5 predicted FMT ORF proteins; D) Phylogenic tree of various rhabdoviruses; E) Example of a Fully replicative GFP expressing FMT strain; and F) Electron microgram of FMT virion (adapted from Tesh et al. Emerging Infect. Dis. 2002).

Throughout the present disclosure, several terms are employed that are defined in the following paragraphs.

As used herein, the words "desire" or "desirable" refer to embodiments of the technology that afford certain benefits, under certain circumstances. However, other embodiments may also be desirable, under the same or other circumstances. Furthermore, the recitation of one or more desired embodiments does not imply that other embodiments are not useful, and is not intended to exclude other embodiments from the scope of the technology.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components or process steps, the present technology also specifically includes embodiments consisting of, or consisting essentially of, such materials, components or processes excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, all compositional percentages are by weight of the total composition, unless otherwise specified. Disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

"A" and "an" as used herein indicate "at least one" of the item is present; a plurality of such items may be present, when possible.

"About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters.

As used herein, the term "and/or" includes any and all combinations of one or more of the associated listed items.

As used herein, a virus that has "reduced levels of neurotoxicity" or "reduced neurotoxicity" would be understood to refer to a virus that, when injected into the right striatum of a mouse brain at a given dose, results in a mouse with fewer signs of neurotoxicity (for example, weigh loss, piloerection, hind leg paralysis, morbidity and mortality) than a mouse which is injected with wild-type maraba virus.

As used herein, "substantially no level of neurotoxicity" or "substantially no neurotoxicity" would be understood to refer to a virus that, when injected introcerebrally into a mouse at 1e6 pfu, results in a mouse with no detectable signs of reduced motor function as measured by time on a rotorod compared to the mouse before injection with the virus.

Detailed Description of Certain Embodiments

Of the more than 250 currently identified rhabdoviruses, several isolated wild type rhabdoviruses were determined to be effective at killing CNS tumour cell lines while retaining attenuation in normal human astrocytes and post-mitotic neurons. Several of these potent viral isolates were also determined to demonstrate remarkable attenuation, resulting in 100% survival after intracerebral inoculation. This is in striking contrast to previously tested Maraba and VSV viruses.

Generally, the present disclosure provides an oncolytic virus for the treatment of cancer. Oncolytic viruses may be used to treat cancer by directly administering the virus to a patient, or by infecting a cell with the virus and administering the infected cell to the patient to deliver the virus. The cell to be infected by the virus may be a cancer cell from the patient. In some examples, the cancer to be treated is brain cancer, such as malignant glioma. One example of a malignant glioma is glioblastoma. The oncolytic virus may exhibit reduced levels of neurotoxicity.

The oncolytic virus may be an isolated viral particle capable of producing a cDNA polynucleotide that includes a sequence according to SEQ ID NO: 1 when the virus is in a host cell.

The oncolytic virus may be an isolated viral particle that includes an RNA polynucleotide that includes a sequence according to SEQ ID NO: 2.

The oncolytic virus may be an isolated viral particle having a genome that includes open reading frames that encode: a protein having a sequence comprising SEQ ID NO: 3, or a variant thereof; a protein having a sequence comprising SEQ ID NO: 4, or a variant thereof; a protein having a sequence comprising SEQ ID NO: 5, or a variant thereof; a protein having a sequence comprising SEQ ID NO: 6, or a variant thereof; and a protein having a sequence comprising SEQ ID NO: 7, or a variant thereof.

The variant of a reference protein may be a protein that has a sequence which is at least 75%, at least 80%, at least 85%, at least 90%, or at least 95% identical to the sequence of the reference protein, and where the variant protein maintains the same biological function as the reference protein.

In some examples, at least one of the open reading frames encodes a protein having a sequence which is a sequence selected from the group consisting of SEQ ID NOs: 3, 4, 5, 6, and 7. In such examples, the variant of a reference protein may be a protein having a sequence which is at least 50%, at least 55%, at least 60%, at least 65%, at least 70%, at least 75%, at least 80%, at least 85%, at least 90%, or at least 95% identical to the sequence of the reference protein, and where the variant protein maintains the same biological function as the reference protein.

The viral genome may include open reading frames that encode: a protein having a sequence comprising SEQ ID NO: 3; a protein having a sequence comprising SEQ ID NO: 4; a protein having a sequence comprising SEQ ID NO: 5; a protein having a sequence comprising SEQ ID NO: 6; and a protein having a sequence comprising SEQ ID NO: 7.

The isolated viral particle may further include at least one additional open reading frame for encoding at least one additional protein. The additional protein may be an immunogenic protein.

The oncolytic virus may be an isolated viral particle capable of producing a cDNA polynucleotide when the virus is in a host cell, the cDNA polynucleotide having a sequence that includes: SEQ ID NO: 8, or a conservative variant thereof; SEQ ID NO: 9, or a conservative variant thereof; 2894-3340 of SEQ ID NO: 10, or a conservative variant thereof; SEQ ID NO: 11, or a conservative variant thereof; SEQ ID NO: 12, or a conservative variant thereof; and promoters thereof.

The conservative variant of a sequence of nucleotides may be a sequence that is at least 75%, at least 80%, at least 85%, at least 90%, or at least 95% identical to the reference sequence of nucleotides. The conservative variant may be a sequence comprising one or more silent substitutions.

An isolated viral particle according to the present disclosure may be used for the treatment of cancer. The cancer may be a brain cancer. The brain cancer may be a glioblastoma. The isolated viral particle may be used for the treatment of cancer by infecting a cell with the virus and the infected cell may be used to deliver the virus to a patient. Techniques for infecting a cell with a virus and using the infected cell to deliver the virus are discussed in, for example: Power A T, et al. Carrier cell-based delivery of an oncolytic virus circumvents antiviral immunity. Mol Ther. 2007 January; 15(1):123-30; and Tyler M A, et al. Neural stem cells target intracranial glioma to deliver an oncolytic adenovirus in vivo. Gene Ther. 2009 February; 16(2):262-78.

An isolated viral particle according to the present disclosure may be used to induce an immunogenic response in a person administered the virus. The immunogenic response may be an anti-cancer response. The isolated viral particle may be used induce an immunogenic response by infecting a cell with the virus and the infected cell may be used to deliver the virus to the person.

The isolated viral particle may be formulated for direct delivery to the central nervous system, outside the blood/brain barrier, inside the blood/brain barrier, or any combination thereof. For example the isolated viral particle may be formulated for administration via intrathecal, intravenous or intracranial injection.

An isolated viral particle according to the present disclosure may be used in a method for treating cancer, where the method includes administering an isolated viral particle according the present disclosure to a patient having cancer. The cancer may be a brain cancer. The brain cancer may be a glioblastoma. The isolated viral particle may be administered to the patient directly to the central nervous system, outside the blood/brain barrier, inside the blood/brain barrier, or any combination thereof. For example, the isolated viral particle may be administered intrathecally, intravenously or via intracranial injection. The isolated viral particle may be directly administered to the patient or may be administered to the patient by infecting a cell with the virus and administering the infected cell to the patient.

An isolated viral particle according to the present disclosure may be used in a method for inducing an immunogenic response in a patient, where the method includes administering an isolated viral particle according to the present disclosure to the patient. The isolated viral particle may be administered to the patient directly to the central nervous system, outside the blood/brain barrier, inside the blood/brain barrier, or any combination thereof. For example, the isolated viral particle may be administered intrathecally, intravenously or via intracranial injection.

An isolated viral particle according to the present disclosure may be included in a kit for the treatment of cancer in a patient, the kit including: the isolated viral particle according to the present disclosure; and instructions for administration of the isolated viral particle to the patient. The cancer may be a brain cancer. The brain cancer may be a glioblastoma. The isolated viral particle may be formulated for direct delivery to the central nervous system, outside the blood/brain barrier, inside the blood/brain barrier, or any combination thereof. For example the isolated viral particle may be formulated for administration via intrathecal, intravenous or intracranial injection.

One example of a rhabdovirus that was determined to be effective at killing CNS tumour cell lines while retaining attenuation in normal human astrocytes and post-mitotic neurons was Farmington rhabdovirus (FMT). See Example 1 and FIG. 1 for a discussion of the genetic components of FMT. Interestingly, FMT shows little or no sequence homology to other rhabdoviruses from the six current genera and thus may constitute a seventh genus in the Rhabdoviridae. This virus was determined to exhibit reduced neurotoxicity after intracranial administration (see Example 2 and FIG. 2). The FMT virus also demonstrated tumour selectivity in vitro (see Example 3 and FIG. 3), and safety and efficacy following intracranial or systemic administration in syngeneic and xenograft mouse models of glioblastoma (see Example 4 and FIG. 4).

As discussed above, several viruses, including Maraba (MRB), Farmington (FMT) and Carajas (CRJ), were determined to have potent killing capacity against a variety of cancer cell lines from the NC60 cell panel. These viruses were also determined to have an ability to eradicate CNS tumour cell lines. These viruses were tested for their safety and efficacy in vitro and in vivo.

Previous viruses, such as wild type and attenuated strains of VSV, are also known to be potent killers of CNS cell lines. However, they are notably neurotoxic and treatment with such viruses often results in rapid weight loss and paralysis upon intracerebral injection at very low doses. Such neurotoxicity prevents application of VSV to treating brain cancer.

As illustrated in Example 2 and FIG. 2, it was determined that, like VSV, both CRJ and MRB also resulted in neurotoxicity in Balb/C mice within a period of 2-7 days after administration. However, it was surprisingly determined that FMT demonstrated no neurotoxicity up to 30 days following direct intracranial injection (IC) of 1e6 pfu.

FMT was determined to be able to kill GBM cells at low multiplicities of infection, and was determined to possess replication kinetics and large burst sizes that rivaled those of the highly lytic Maraba virus. FMT was also determined to be poorly cytolytic in normal human astrocytes and primary neurons (see Example 3 and FIG. 3). The mechanism of tumour selectivity appears to be independent of interferon signaling, as is currently the established mechanism of selectivity governing rhabdovirus based oncolytic agents. FMT appears to infect normal cells equally to tumour cells, but only induces apoptosis in tumour cells. FMT was determined to not trigger caspase 8 in normal cells, even though there is robust virus protein synthesis. Moreover, FMT's selective cytotoxicity mechanism rendered the virus non-neurotoxic despite its strong ability to block interferon (IFN) production. This indicates that rhabdovirus infections of the CNS cannot be effectively controlled by interferon anti-virus defenses when viruses are delivered directly into the brain. When delivered peripherally, FMT was determined to be as attenuated as previously published engineered VSV deltaM51 or MR MG1 strains.

As illustrated in Example 4 and FIG. 4, the FMT virus may be used to treat human xenograft and immunocompetent syngeneic models by either local regional or systemic administration. In vivo efficacy in a human orthotopic U87MG model after a single IC or IV dose of FMT is described in Example 4. In fact, IV even achieved durable cures. Notably both modes of delivery are not only able to treat the primary glioma but are able to effectively and durably treat U87MG spinal metastasis in 100% of the animals. Based on these results, it is expected that FMT virus could be used to treat other cancers, such as, for example, medulloblastomas. It is expected that FMT virus could be used to treat primary cancers as well as metastasized cancers, such as to the CNS. Although FMT virus exhibits reduced neurotoxicity and is, for that reason, suitable for use in the treatment of neurological tumors, it should be understood that the FMT virus may be used for the treatment of non-neurological cancers. It should also be understood that other viruses according to the present disclosure could be used for the treatment of non-neurological cancers.

FMT virus has been demonstrated to induce an anti-tumor immunity. As illustrated in Example 5 and FIG. 5, mice previously harboring CT-2A tumors that had been successfully treated with IC FMT virus infusions were injected for a second time with CT-2A cells directly into the brain. It was determined that previously cured mice rejected the cells. When, concomitant with FMT virus treatment, cytotoxic T-lymphocytes (CTL) were removed using antibodies directed toward CD8, it was determined that mice stripped of their CD8+ T-cells all eventually re-grew the subsequently injected CT-2A cells and failed therapy. This suggests that in addition to direct tumour cell lysis and putative other mechanisms of action, the FMT virus induces an anti-tumor immunity when CTLs are present. Accordingly, it is expected that a virus according to the present disclosure may be used to induce an immune response in a patient exposed to the virus. The immune response may be, for example, an anti-cancer immune response.

Several groups have also shown impressive efficacy in U87MG model but seldom in a syngeneic immunocompetent GBM model. Moreover, GBM models are often treated at predetermined times when animals are still healthy and tumours presumably small. In the examples discussed herein, treatment was commenced 14 days post implantation, which is approximately 4-7 days before the animals displayed symptoms of their disease. In the orthoptopic CT-2A syngeneic GBM model, treatment was commenced at a stage (19 days post implantation) when animals started displaying overt symptoms of disease. These symptoms include lack of grooming, hydrocephaly, and hunched phenotype. This treatment protocol is believed to be particularly relevant to the clinical setting where patients are diagnosed and treated after presenting with symptoms. In the examples discussed herein, either a single IC dose or 6 IV doses of FMT was administered. The results demonstrated a similarly significant survival profile achieving a significant prolongation in survival and several mice in each group (20-30%) were durably cured beyond 100 days. The CT-2A model was chosen because it resulted in an aggressive infiltrative tumour and shares proliferative, metabolic, histological, and immunohistochemical profiles observed in human glioblastoma multiforme.

The FMT virus was also demonstrated to not distinguish tumor from non-tumor cells via differential infectivity or viral protein production (see Example 6 and FIGS. 6). The FMT virus is similarly productive in non-cancerous as compared to cancerous cells. Example 6 also demonstrated that the genome of wild type FMT virus may be mutated to include an additional protein, in the present example the additional protein added to the genome of wild type FMT virus was green fluorescent protein (GFP). The resulting mutated "rec-FMT-GFP virus" was demonstrated to block human type I interferon response and productively infect both cancerous and non-cancerous cells.

The FMT virus was also demonstrated to induce cell death in a manner dependent on the anti-apoptotic threshold of the infected cells, and not on the productivity of the virus infection within the infected cell (see Example 7 and FIG. 7). FMT viral infection of a cell appears to initiate activation (cleavage) of caspase 8, caspase 9, BH3-interacting domain and Poly(ADP-ribose) Polymerase in tumor cells.

In summary, FMT is an exemplary oncolytic virus according to the present disclosure, and which has been demonstrated to have a high therapeutic index against human brain cancer cell lines and patient samples in vitro, and which has a demonstrated potent efficacy when used to treat preclinical models of brain cancer. Accordingly, it is expected that isolated viral particles according to the present disclosure may be used to treat cancer, such as brain cancer (for example glioblastoma). It is also expected that isolated viral particles according to the present disclosure may be used to induce an immunogenic response, such as an anti-cancer response, in a person administered the virus.

Polynucleotide and Amino Acid Sequences

Polynucleotides comprising nucleic acid sequences (e.g., DNA and RNA) and amino acid (e.g., protein) sequences are provided that may be used in a variety of methods and techniques known to those skilled in the art of molecular biology. These include isolated, purified, and recombinant forms of the listed sequences and further include complete or partial forms of the listed sequences. Non-limiting uses for amino acid sequences include making antibodies to proteins or peptides comprising the disclosed amino acid sequences. Non-limiting uses for the polynucleotide sequences include making hybridization probes, as primers for use in the polymerase chain reaction (PCR), for chromosome and gene mapping, and the like. Complete or partial amino acid or polynucleotide sequences can be used in such methods and techniques.

The present disclosure features the identification of polynucleotide sequences, including gene sequences and coding nucleic acid sequences, and amino acid sequences. In addition to the sequences expressly provided in the accompanying sequence listing, also included are polynucleotide sequences that are related structurally and/or functionally. Also included are polynucleotide sequences that hybridize under stringent conditions to any of the polynucleotide sequences in the sequence listing, or a subsequence thereof (e.g., a subsequence comprising at least 100 contiguous nucleotides). Polynucleotide sequences also include sequences and/or subsequences configured for RNA production and/or translation, e.g., mRNA, antisense RNA, sense RNA, RNA silencing and interference configurations, etc.

Polynucleotide sequences that are substantially identical to those provided in the sequence listing can be used in the compositions and methods disclosed herein. Substantially identical or substantially similar polynucleotide sequences are defined as polynucleotide sequences that are identical, on a nucleotide by nucleotide basis, with at least a subsequence of a reference polynucleotide. Such polynucleotides can include, e.g., insertions, deletions, and substitutions relative to any of those listed in the sequence listing. For example, such polynucleotides are typically at least about 70% identical to a reference polynucleotide selected from those in the sequence listing, or a subsequence thereof. For example, at least 7 out of 10 nucleotides within a window of comparison are identical to the reference sequence selected. Furthermore, such sequences can be at least about 70%, at least about 75%, at least about 80%, at least about 85%, at least about 90%, at least about 95%, at least about 98%, at least about 99%, or at least about 99.5%, identical to the reference sequence. Subsequences of these polynucleotides can include at least about 5, at least about 10, at least about 15, at least about 20, at least about 25, at least about 50, at least about 75, at least about 100, at least about 500, about 1000 or more, contiguous nucleotides or complementary subsequences. Such subsequences can be, e.g., oligonucleotides, such as synthetic oligonucleotides, isolated oligonucleotides, or full-length genes or cDNAs. Polynucleotide sequences complementary to any of the described sequences are included.

Amino acid sequences include the amino acid sequences represented in the sequence listing, and subsequences thereof. Also included are amino acid sequences that are highly related structurally and/or functionally. For example, in addition to the amino acid sequences in the sequence listing, amino acid sequences that are substantially identical can be used in the disclosed compositions and methods. Substantially identical or substantially similar amino acid sequences are defined as amino acid sequences that are identical, on an amino acid by amino acid basis, with at least a subsequence of a reference amino acid sequence. Such amino acid sequences can include, e.g., insertions, deletions, and substitutions relative to any of the amino acid sequences in the sequence listing. For example, such amino acids are typically at least about 70% identical to a reference amino acid sequence, or a subsequence thereof. For example, at least 7 out of 10 amino acids within a window of comparison are identical to the reference amino acid sequence selected. Frequently, such amino acid sequences are at least about 70%, at least about 75%, at least about 80%, at least about 85%, at least about 90%, at least about 95%, at least about 98%, at least about 99%, or at least about 99.5%, identical to the reference sequence. Subsequences of the amino acid sequences can include at least about 5, at least about 10, at least about 15, at least about 20, at least about 25, at least about 50, at least about 75, at least about 100, at least about 500, about 1000 or more, contiguous amino acids. Conservative variants of amino acid sequences or subsequences are also possible. Amino acid sequences can be immunogenic, enzymatically active, enzymatically inactive, and the like.

Where the polynucleotide sequences are translated to form a polypeptide or subsequence of a polypeptide, nucleotide changes can result in either conservative or non-conservative amino acid substitutions. Conservative amino acid substitutions refer to the interchangeability of residues having functionally similar side chains. Conservative substitution tables providing functionally similar amino acids are well known in the art. Table 1 sets forth examples of six groups containing amino acids that are "conservative substitutions" for one another. Other conservative substitution charts are available in the art, and can be used in a similar manner.

TABLE 1

| Conservative Substitution Group | | | | |
|---|---|---|---|---|
| 1 | Alanine (A) | Serine (S) | Threonine (T) | |
| 2 | Aspartic acid (D) | Glutamic acid(E) | | |
| 3 | Asparagine (N) | Glutamine (Q) | | |
| 4 | Arginine (R) | Lysine (K) | | |
| 5 | Isoleucine (I) | Leucine (L) | Methionine (M) | Valine (V) |
| 6 | Phenylalanine (F) | Tyrosine (Y) | Tryptophan (W) | |

One of skill in the art will appreciate that many conservative substitutions yield functionally identical constructs. For example, as discussed above, owing to the degeneracy of the genetic code, "silent substitutions" (i.e., substitutions in a polynucleotide sequence which do not result in an alteration in an encoded polypeptide) are an implied feature of every polynucleotide sequence which encodes an amino acid. Similarly, "conservative amino acid substitutions," in one or a few amino acids in an amino acid sequence (e.g., about 1%, 2%, 3%, 4%, 5%, 6%, 7%, 8%, 9%, 10% or more) are substituted with different amino acids with highly similar properties, are also readily identified as being highly similar to a disclosed construct. Such conservative variations of each disclosed sequence are also contemplated.

Methods for obtaining conservative variants, as well as more divergent versions of the polynucleotide and amino acid sequences, are widely known in the art. In addition to naturally occurring homologues which can be obtained, e.g., by screening genomic or expression libraries according to any of a variety of well-established protocols, see, e.g., Ausubel et al. Current Protocols in Molecular Biology (supplemented through 2004) John Wiley & Sons, New York ("Ausubel"); Sambrook et al. Molecular Cloning—A Laboratory Manual (2nd Ed.), Vol. 1-3, Cold Spring Harbor Laboratory, Cold Spring Harbor, N.Y., 1989 ("Sambrook"), and Berger and Kimmel Guide to Molecular Cloning Techniques, Methods in Enzymology volume 152 Academic Press, Inc., San Diego, Calif. ("Berger"), additional variants can be produced by any of a variety of mutagenesis procedures. Many such procedures are known in the art, including site directed mutagenesis, oligonucleotide-directed mutagenesis, and many others. For example, site directed mutagenesis is described, e.g., in Smith (1985) "In vitro mutagenesis" Ann. Rev. Genet. 19:423-462, and references therein, Botstein & Shortie (1985) "Strategies and applications of in vitro mutagenesis" Science 229:1193-1201; and Carter (1986) "Site-directed mutagenesis" Biochem. J. 237:1-7. Oligonucleotide-directed mutagenesis is described, e.g., in Zoller & Smith (1982) "Oligonucleotide-directed mutagenesis using M13-derived vectors: an efficient and general procedure for the production of point mutations in any DNA fragment" Nucleic Acids Res.

10:6487-6500). Mutagenesis using modified bases is described e.g., in Kunkel (1985) "Rapid and efficient site-specific mutagenesis without phenotypic selection" Proc. Natl. Acad. Sci. USA 82:488-492, and Taylor et al. (1985) "The rapid generation of oligonucleotide-directed mutations at high frequency using phosphorothioate-modified DNA" Nucl. Acids Res. 13: 8765-8787. Mutagenesis using gapped duplex DNA is described, e.g., in Kramer et al. (1984) "The gapped duplex DNA approach to oligonucleotide-directed mutation construction" Nucl. Acids Res. 12: 9441-9460). Point mismatch mutagenesis is described, e.g., by Kramer et al. (1984) "Point Mismatch Repair" Cell 38:879-887). Double-strand break mutagenesis is described, e.g., in Mandecki (1986) "Oligonucleotide-directed double-strand break repair in plasmids of *Escherichia coli*: a method for site-specific mutagenesis" Proc. Natl. Acad. Sci. USA, 83:7177-7181, and in Arnold (1993) "Protein engineering for unusual environments" Current Opinion in Biotechnology 4:450-455). Mutagenesis using repair-deficient host strains is described, e.g., in Carter et al. (1985) "Improved oligonucleotide site-directed mutagenesis using M13 vectors" Nucl. Acids Res. 13: 4431-4443. Mutagenesis by total gene synthesis is described e.g., by Nambiar et al. (1984) "Total synthesis and cloning of a gene coding for the ribonuclease S protein" Science 223: 1299-1301. DNA shuffling is described, e.g., by Stemmer (1994) "Rapid evolution of a protein in vitro by DNA shuffling" Nature 370:389-391, and Stemmer (1994) "DNA shuffling by random fragmentation and reassembly: In vitro recombination for molecular evolution," Proc. Natl. Acad. Sci. USA 91:10747-10751.

Many of the above methods are further described in Methods in Enzymology Volume 154, which also describes useful controls for trouble-shooting problems with various mutagenesis methods. Kits for mutagenesis, library construction and other diversity generation methods are also commercially available. For example, kits are available from, e.g., Amersham International plc (Piscataway, N.J.) (e.g., using the Eckstein method above), Bio/Can Scientific (Mississauga, Ontario, CANADA), Bio-Rad (Hercules, Calif.) (e.g., using the Kunkel method described above), Boehringer Mannheim Corp. (Ridgefield, Conn.), Clonetech Laboratories of BD Biosciences (Palo Alto, Calif.), DNA Technologies (Gaithersburg, Md.), Epicentre Technologies (Madison, Wis.) (e.g., the 5 prime 3 prime kit); Genpak Inc. (Stony Brook, N.Y.), Lemargo Inc (Toronto, CANADA), Invitrogen Life Technologies (Carlsbad, Calif.), New England Biolabs (Beverly, Mass.), Pharmacia Biotech (Peapack, N.J.), Promega Corp. (Madison, Wis.), QBiogene (Carlsbad, Calif.), and Stratagene (La Jolla, Calif.) (e.g., QuickChange™ site-directed mutagenesis kit and Chameleon™ double-stranded, site-directed mutagenesis kit).

Determining Sequence Relationships

Similar sequences can be objectively determined by any number of methods, e.g., percent identity, hybridization, immunologically, and the like. A variety of methods for determining relationships between two or more sequences (e.g., identity, similarity and/or homology) are available and well known in the art. Methods include manual alignment, computer assisted sequence alignment, and combinations thereof, for example. A number of algorithms (which are generally computer implemented) for performing sequence alignment are widely available or can be produced by one of skill. These methods include, e.g., the local homology algorithm of Smith and Waterman (1981) Adv. Appl. Math. 2:482; the homology alignment algorithm of Needleman and Wunsch (1970) J. Mol. Biol. 48:443; the search for similarity method of Pearson and Lipman (1988) Proc. Natl. Acad. Sci. (USA) 85:2444; and/or by computerized implementations of these algorithms (e.g., GAP, BESTFIT, FASTA, and TFASTA in the Wisconsin Genetics Software Package Release 7.0, Genetics Computer Group, 575 Science Dr., Madison, Wis.).

For example, software for performing sequence identity (and sequence similarity) analysis using the BLAST algorithm is described in Altschul et al. (1990) J. Mol. Biol. 215:403-410. This software is publicly available, e.g., through the National Center for Biotechnology Information on the internet at ncbi.nlm.nih.gov. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP (BLAST Protein) program uses as defaults a wordlength (W) of 3, an expectation (E) of 10, and the BLOSUM62 scoring matrix (see, Henikoff & Henikoff (1989) Proc. Natl. Acad. Sci. USA 89:10915).

Additionally, the BLAST algorithm performs a statistical analysis of the similarity between two sequences (see, e.g., Karlin & Altschul (1993) Proc. Nat'l. Acad. Sci. USA 90:5873-5787). One measure of similarity provided by the BLAST algorithm is the smallest sum probability (p(N)), which provides an indication of the probability by which a match between two nucleotide or amino acid sequences would occur by chance. For example, a nucleic acid is considered similar to a reference sequence (and, therefore, in this context, homologous) if the smallest sum probability in a comparison of the test nucleic acid to the reference nucleic acid is less than about 0.1, or less than about 0.01, and or even less than about 0.001.

Another example of a sequence alignment algorithm is PILEUP, which creates a multiple sequence alignment from a group of related sequences using progressive, pairwise alignments. It can also plot a tree showing the clustering relationships used to create the alignment. PILEUP uses a simplification of the progressive alignment method of Feng & Doolittle (1987) J. Mol. Evol. 35:351-360. The method used is similar to the method described by Higgins & Sharp (1989) CABIOS 5:151-153. The program can align, e.g., up to 300 sequences of a maximum length of 5,000 letters. The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. The final alignment is achieved by a series of progressive, pairwise alignments. The program can also be used to plot a dendogram or tree representation of clustering relationships. The program is run by designating specific sequences and their amino acid or nucleotide coordinates for regions of sequence comparison.

An additional example of an algorithm that is suitable for multiple DNA, or amino acid, sequence alignments is the CLUSTALW program (Thompson, J. D. et al. (1994) Nucl. Acids. Res. 22: 4673-4680). CLUSTALW performs multiple pairwise comparisons between groups of sequences and assembles them into a multiple alignment based on homology. Gap open and Gap extension penalties can be, e.g., 10 and 0.05 respectively. For amino acid alignments, the BLOSUM algorithm can be used as a protein weight matrix. See, e.g., Henikoff and Henikoff (1992) Proc. Natl. Acad. Sci. USA 89: 10915-10919.

Polynucleotide hybridization similarity can also be evaluated by hybridization between single stranded (or single stranded regions of) nucleic acids with complementary or partially complementary polynucleotide sequences. Hybridization is a measure of the physical association between nucleic acids, typically, in solution, or with one of the nucleic acid strands immobilized on a solid support, e.g., a membrane, a bead, a chip, a filter, etc. Nucleic acid hybridization occurs based on a variety of well characterized physico-chemical forces, such as hydrogen bonding, solvent exclusion, base stacking, and the like. Numerous protocols for nucleic acid hybridization are well known in the art. An extensive guide to the hybridization of nucleic acids is found in Tijssen (1993) Laboratory Techniques in Biochemistry and Molecular Biology—Hybridization with Nucleic Acid Probes, part I, chapter 2, "Overview of principles of hybridization and the strategy of nucleic acid probe assays," (Elsevier, N.Y.), as well as in Ausubel et al. Current Protocols in Molecular Biology (supplemented through 2004) John Wiley & Sons, New York ("Ausubel"); Sambrook et al. Molecular Cloning—A Laboratory Manual (2nd Ed.), Vol. 1-3, Cold Spring Harbor Laboratory, Cold Spring Harbor, N.Y., 1989 ("Sambrook"), and Berger and Kimmel Guide to Molecular Cloning Techniques, Methods in Enzymology volume 152 Academic Press, Inc., San Diego, Calif. ("Berger"). Hames and Higgins (1995) Gene Probes 1, IRL Press at Oxford University Press, Oxford, England (Hames and Higgins 1) and Hames and Higgins (1995) Gene Probes 2, IRL Press at Oxford University Press, Oxford, England (Hames and Higgins 2) provide details on the synthesis, labeling, detection and quantification of DNA and RNA, including oligonucleotides.

Conditions suitable for obtaining hybridization, including differential hybridization, are selected according to the theoretical melting temperature (Tm) between complementary and partially complementary nucleic acids. Under a given set of conditions, e.g., solvent composition, ionic strength, etc., the. Tm is the temperature at which the duplex between the hybridizing nucleic acid strands is 50% denatured. That is, the Tm corresponds to the temperature corresponding to the midpoint in transition from helix to random coil; it depends on the length of the polynucleotides, nucleotide composition, and ionic strength, for long stretches of nucleotides.

After hybridization, unhybridized nucleic acids can be removed by a series of washes, the stringency of which can be adjusted depending upon the desired results. Low stringency washing conditions (e.g., using higher salt and lower temperature) increase sensitivity, but can product nonspecific hybridization signals and high background signals. Higher stringency conditions (e.g., using lower salt and higher temperature that is closer to the T.sub.m) lower the background signal, typically with primarily the specific signal remaining, See, also, Rapley, R. and Walker, J. M. eds., Molecular Biomethods Handbook (Humana Press, Inc. 1998).

"Stringent hybridization wash conditions" or "stringent conditions" in the context of nucleic acid hybridization experiments, such as Southern and northern hybridizations, are sequence dependent, and are different under different environmental parameters. An extensive guide to the hybridization of nucleic acids is found in Tijssen (1993), supra, and in Hames and Higgins 1 and Hames and Higgins 2, supra.

An example of stringent hybridization conditions for hybridization of complementary nucleic acids which have more than 100 complementary residues on a filter in a Southern or northern blot is 2×SSC, 50% formamide at 42° C., with the hybridization being carried out overnight (e.g., for approximately 20 hours). An example of stringent wash conditions is a 0.2×SSC wash at 65° C. for 15 minutes (see Sambrook, supra for a description of SSC buffer). Often, the wash determining the stringency is preceded by a low stringency wash to remove signal due to residual unhybridized probe. An example low stringency wash is 2×SSC at room temperature (e.g., 20° C. for 15 minutes).

In general, a signal to noise ratio of at least 2.5×-5× (and typically higher) than that observed for an unrelated probe in the particular hybridization assay indicates detection of a specific hybridization. Detection of at least stringent hybridization between two sequences indicates relatively strong structural similarity to those provided in the sequence listings herein.

Generally, "highly stringent" hybridization and wash conditions are selected to be about 5° C. or less lower than the thermal melting point (Tm) for the specific sequence at a defined ionic strength and pH (as noted below, highly stringent conditions can also be referred to in comparative terms). Target sequences that are closely related or identical to the nucleotide sequence of interest (e.g., "probe") can be identified under stringent or highly stringent conditions. Lower stringency conditions are appropriate for sequences that are less complementary.

For example, in determining stringent or highly stringent hybridization (or even more stringent hybridization) and wash conditions, the stringency of the hybridization and wash conditions is gradually increased (e.g., by increasing temperature, decreasing salt concentration, increasing detergent concentration, and/or increasing the concentration of organic solvents, such as formamide, in the hybridization or wash), until a selected set of criteria are met. For example, the stringency of the hybridization and wash conditions is gradually increased until a probe comprising one or more of the present polynucleotide sequences, or a subsequence thereof, and/or complementary polynucleotide sequences thereof, binds to a perfectly matched complementary target, with a signal to noise ratio that is at least 2.5×, and optionally 5×, or 10×, or 100× or more, as high as that observed for hybridization of the probe to an unmatched target, as desired.

Using subsequences derived from the nucleic acids listed in the sequence listing, novel target nucleic acids can be obtained; such target nucleic acids are also a feature of the invention. For example, such target nucleic acids include sequences that hybridize under stringent conditions to an oligonucleotide probe that corresponds to a unique subsequence of any of the polynucleotides in the sequence listing, or a complementary sequence thereof; the probe optionally encodes a unique subsequence in any of the amino acid sequences of the sequence listing.

For example, hybridization conditions are chosen under which a target oligonucleotide that is perfectly complementary to the oligonucleotide probe hybridizes to the probe with at least about a 5-10× higher signal to noise ratio than for hybridization of the target oligonucleotide to a negative control non-complimentary nucleic acid. Higher ratios of signal to noise can be achieved by increasing the stringency of the hybridization conditions such that ratios of about 15×, 20×, 30×, 50× or more are obtained. The particular signal will depend on the label used in the relevant assay, e.g., a fluorescent label, a calorimetric label, a radioactive label, or the like.

Vectors, Promoters and Expression Systems

Polynucleotide sequences of the present disclosure can be in any of a variety of forms, e.g., expression cassettes, vectors, plasmids, viral particles, or linear nucleic acid sequences. For example, vectors, plasmids, cosmids, bacterial artificial chromosomes (BACs), YACs (yeast artificial chromosomes), phage, viruses and nucleic acid segments can comprise the present nucleic acid sequences or subsequences thereof. These nucleic acid constructs can further include promoters, enhancers, polylinkers, regulatory genes, etc. Thus, the present disclosure also relates, e.g., to vectors comprising the polynucleotides disclosed herein, host cells that incorporate these vectors, and the production of the various disclosed polypeptides (including those in the sequence listing) by recombinant techniques.

In accordance with these aspects, the vector may be, for example, a plasmid vector, a single or double-stranded phage vector, or a single or double-stranded RNA or DNA viral vector. Such vectors may be introduced into cells as polynucleotides, preferably DNA, by well known techniques for introducing DNA and RNA into cells. The vectors, in the case of phage and viral vectors, also may be and preferably are introduced into cells as packaged or encapsidated virus by well known techniques for infection and transduction. Viral vectors may be replication competent or replication defective. In the latter case, viral propagation generally will occur only in complementing host cells.

In some examples, vectors include those useful for expression of polynucleotides and polypeptides of the present invention. Generally, such vectors comprise cis-acting control regions effective for expression in a host, operably linked to the polynucleotide to be expressed. Appropriate trans-acting factors are supplied by the host, supplied by a complementing vector or supplied by the vector itself upon introduction into the host.

In certain examples in this regard, the vectors provide for protein expression. Such preferred expression may be inducible expression, temporally limited expression, or expression restricted to predominantly certain types of cells, or any combination of the above. Some embodiments of inducible vectors can be induced for expression by environmental factors that are easy to manipulate, such as temperature and nutrient additives. A variety of vectors suitable to this aspect, including constitutive and inducible expression vectors for use in prokaryotic and eukaryotic hosts, are well known and employed routinely by those of skill in the art. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as rhabdoviruses, baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids and binaries used for *Agrobacterium*-mediated transformations.

Vectors can include a selectable marker and a reporter gene. For ease of obtaining sufficient quantities of vector, a bacterial origin that allows replication in *E. coli* can be used. The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Useful plant binary vectors include BIN19 and its derivatives available from Clontech. These vectors are listed solely by way of illustration of the many commercially available and well-known vectors that are available to those of skill in the art. It will be appreciated that any other plasmid or vector suitable for, for example, introduction, maintenance, propagation or expression of one or more polynucleotides and/or polypeptides as provided in the present sequence listing, including variants thereof as described, in a host may be used.

In general, expression constructs will contain sites for transcription initiation and termination, and, in the transcribed region, a ribosome-binding site for translation when the construct encodes a polypeptide. The coding portion of the mature transcripts expressed by the constructs will include a translation-initiating AUG at the beginning and a termination codon appropriately positioned at the end of the polypeptide to be translated. In addition, the constructs may contain control regions that regulate as well as engender expression. Generally, in accordance with many commonly practiced procedures, such regions will operate by controlling transcription, such as transcription factors, repressor binding sites and termination signals, among others. For secretion of a translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Transcription of the DNA (e.g., encoding the polypeptides) of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at by 100 to 270, the cytomegalovirus early promoter enhancer, the polyoma enhancer on the late side of the replication origin, and adenovirus enhancers. Additional enhancers useful in the invention to increase transcription of the introduced DNA segment, include, inter alia, viral enhancers like those within the 35S promoter, as shown by Odell et al., Plant Mol. Biol. 10:263-72 (1988), and an enhancer from an opine gene as described by Fromm et al., Plant Cell 1:977 (1989). The enhancer may affect the tissue-specificity and/or temporal specificity of expression of sequences included in the vector.

Termination regions also facilitate effective expression by ending transcription at appropriate points. Useful terminators include, but are not limited to, pinII (see An et al., Plant Cell 1(1):115-122 (1989)), glb1 (see Genbank Accession #L22345), gz (see gzw64a terminator, Genbank Accession #S78780), and the nos terminator from *Agrobacterium*. The termination region can be native with the promoter nucleotide sequence, can be native with the DNA sequence of interest, or can be derived from another source. For example, other convenient termination regions are available from the Ti-plasmid of *A. tumefaciens*, such as the octopine synthase and nopaline synthase termination regions. See also: Guerineau et al. (1991) Mol. Gen. Genet. 262:141-144; Proudfoot (1991) Cell 64:671-674; Sanfacon et al. (1991) Genes Dev. 5:141-149; Mogen et al. (1990) Plant Cell 2:1261-1272; Munroe et al. (1990) Gene 91:151-158; Belles et al. 1989) Nucleic Acids Res. 17:7891-7903; and Joshi et al. (1987) Nucleic Acid Res. 15:9627-9639.

Among known eukaryotic promoters suitable for generalized expression are the CMV immediate early promoter, the HSV thymidine kinase promoter, the early and late SV40 promoters, the promoters of retroviral LTRs, such as those of the Rous sarcoma virus ("RSV"), metallothionein promoters, such as the mouse metallothionein-I promoter and various plant promoters, such as globulin-1. The native promoters of the polynucleotide sequences listing in the sequence listing may also be used. Representatives of prokaryotic promoters include the phage lambda PL promoter, the *E. coli* lac, trp and tac promoters to name just a few of the well-known promoters.

Isolated or recombinant viruses, virus infected cells, or cells including one or more portions of the present polynucleotide sequences and/or expressing one or more portions of the present amino acid sequences are also contemplated.

A polynucleotide, optionally encoding the heterologous structural sequence of an amino acid sequence as disclosed, generally will be inserted into a vector using standard techniques so that it is operably linked to a promoter for expression. Operably linked, as used herein, includes reference to a functional linkage between a promoter and a second sequence, wherein the promoter sequence initiates and mediates transcription of the DNA corresponding to the second sequence. Generally, operably linked means that the polynucleotide sequence being linked is contiguous and, where necessary to join two protein coding regions, contiguous and in the same reading frame. When the polynucleotide is intended for expression of a polypeptide, the polynucleotide will be positioned so that the transcription start site is located appropriately 5' to a ribosome binding site. The ribosome-binding site will be 5' to the AUG that initiates translation of the polypeptide to be expressed. Generally, there will be no other open reading frames that begin with an initiation codon, usually AUG, and lie between the ribosome binding site and the initiation codon. Also, generally, there will be a translation stop codon at the end of the polypeptide and there will be a polyadenylation signal in constructs for use in eukaryotic hosts. Transcription termination signals appropriately disposed at the 3' end of the transcribed region may also be included in the polynucleotide construct.

For nucleic acid constructs designed to express a polypeptide, the expression cassettes can additionally contain 5' leader sequences. Such leader sequences can act to enhance translation. Translation leaders are known in the art and include: picornavirus leaders, for example: EMCV leader (Encephalomyocarditis 5' noncoding region), Elroy-Stein et al. (1989) Proc. Nat. Acad. Sci. USA 86:6126-6130; potyvirus leaders, for example, TEV leader (Tobacco Etch Virus), Allison et al. (1986); MDMV leader (Maize Dwarf Mosaic Virus), Virology 154:9-20; human immunoglobulin heavy-chain binding protein (BiP), Macejak et al. (1991) Nature 353:90-94; untranslated leader from the coat protein mRNA of alfalfa mosaic virus (AMV RNA 4), Jobling et al. (1987) Nature 325:622-625); tobacco mosaic virus leader (TMV), Gallie et al. (1989) Molecular Biology of RNA, pages 237-256; and maize chlorotic mottle virus leader (MCMV) Lommel et al. (1991) Virology 81:382-385. See also Della-Cioppa et al. (1987) Plant Physiology 84:965-968. The cassette can also contain sequences that enhance translation and/or mRNA stability such as introns. The expression cassette can also include, at the 3' terminus of the isolated nucleotide sequence of interest, a translational termination region.

In those instances where it is desirable to have the expressed product of the polynucleotide sequence directed to a particular organelle or secreted at the cell's surface the expression cassette can further comprise a coding sequence for a transit peptide. Such transit peptides are well known in the art and include, but are not limited to: the transit peptide for the acyl carrier protein, the small subunit of RUBISCO, plant EPSP synthase, and the like.

In making an expression cassette, the various DNA fragments can be manipulated so as to provide for the polynucleotide sequences in the proper orientation and, as appropriate, in the proper reading frame. Toward this end, adapters or linkers can be employed to join DNA fragments or other manipulations can be involved to provide for convenient restriction sites, removal of superfluous DNA, removal of restriction sites, or the like. For this purpose, in vitro mutagenesis, primer repair, restriction digests, annealing, and resubstitutions such as transitions and transversions, can be employed.

Introduction of a construct into a host cell can be effected by calcium phosphate transfection, DEAE-dextran mediated transfection, microinjection, cationic lipid-mediated transfection, electroporation, transduction, scrape loading, ballistic introduction, infection or other methods. Such methods are described in many standard laboratory manuals, such as Davis et al., Basic Methods in Molecular Biology, (1986) and Sambrook et al., Molecular Cloning—A Laboratory Manual, 2nd Ed., Cold Spring Harbor Laboratory Press, Cold Spring Harbor, N.Y. (1989).

Representative examples of appropriate hosts include bacterial cells, such as streptococci, staphylococci, *E. coli, streptomyces* and *Salmonella typhimurium* cells; fungal cells, such as yeast cells and *Aspergillus* cells; insect cells such as *Drosophila* S2 and *Spodoptera* Sf9 cells; animal cells such as CHO, COS and Bowes melanoma cells; and plant cells.

The host cells can be cultured in conventional nutrient media, which may be modified as appropriate for, inter alia, activating promoters, selecting transformants or amplifying genes. Culture conditions, such as temperature, pH and the like, previously used with the host cell selected for expression generally will be suitable for expression of nucleic acids and/or polypeptides, as will be apparent to those of skill in the art. Mature proteins can be expressed in mammalian cells, yeast, bacteria, or other cells under the control of appropriate promoters. Cell-free translation systems can also be employed to produce such proteins using RNAs derived from the polynucleotides disclosed herein.

Following transformation of a suitable host strain and growth of the host strain to an appropriate cell density, where the selected promoter is inducible it is induced by appropriate means (e.g., temperature shift or exposure to chemical inducer) and cells are cultured for an additional period. Cells typically then are harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents; such methods are well known to those skilled in the art.

Compositions and methods of the present disclosure can include administering the polynucleotides and/or amino acids as provided herein. For example, treatments for glioblastoma can include administering one or more of the polynucleotides and/or amino acids. The one or more polynucleotides and/or amino acids may be in an isolated form or may be part of a composition, including a viral particle. In various embodiments, the administering can take the following forms: intradermal, transdermal, parenteral, intravascular, intravenous, intramuscular, intranasal, subcutaneous, regional, percutaneous, intratracheal, intraperitoneal, intraarterial, intravesical, intratumoral, inhalation, perfusion, lavage, direct injection, alimentary, oral, or intracranial administration.

Materials and Methods

Cell lines: U87MG, U343, U373, SF268, SF265, SF539, SNB19, SNB75, Vero, U118, normal human astrocytes (NHA), CT-2A, DBT, GL261 and human GM38 primary fibroblasts (National Institute of General Medical Sciences Mutant Cell Repository, Camden, N.J.) were propagated in Dulbecco's modified Eagle's medium (Hyclone, Logan, Utah) supplemented with 10% fetal calf serum (Cansera, Etobicoke, Ontario, Canada).

Viability Assays: The indicated cell lines were plated at a density of 10 000 cells/well into 96 well plates. The next day cells were infected with the rMarabaWT, or FMT at various multiplicity of infections (0.0001-10 pfu/cell). Following a 48 hour incubation Alamar Blue (Resazurin sodium salt (Sigma-Aldrich)) was added to a final concentration of 20 μg/ml. After a 6 hour incubation the absorbance was read at a wavelength of 573 nm.

Plaque assays: Vero cells were plated at a density of 5e5 cells per/well of a 6 well dish. The next day 100 l of serial viral dilutions were prepared and added for 1 hour to Vero cells. After viral adsorption 2 ml of agarose overlay was added (1:1 1% agarose: 2×DMEM and 20% FCS). Plaques were counted the following day.

Interferon bioassay: PC-3 cells were infected with rMarabaWT, ΔM51 or FMT, at a multiplicity of infection of 3 pfu/cell for 24 hours. The following day supernatant was acid neutralized with 0.25N HCl overnight at 4° C. followed by the addition of 0.25 NaOH to adjust the pH to 7. Vero cells were incubated with the neutralized supernatant for 24 hours and subsequently infected rMaraba WT with a multiplicity of infection ranging from 0.0001 to 100 pfu/cell. Any interferon secreted by the PC-3 cells in response to Maraba or the attenuated mutants would subsequently protect the Vero cells from infection with Maraba. After 24 hours, survival was quantitated using a crystal violet assay. Briefly cells were incubated with 1% crystal violet solution, washed, dried, resuspended in 1% SDS and read at a wavelength of 595 nm.

Determination of in vivo toxicity: For the intracranial (IC) route of administration (roa), groups of 6-8 week old female BALB/c mice (n=5/group) were given a single IC infusion of the indicated viruses in log increments per group ranging from $10^2$-$10^7$ pfu. For the intravenous (IV) roa, groups of five 6-8 week old female BALB/c mice were given a single IV injection of the indicated viruses into the tail vein, in half log increments per group ranging from $3\times10^6$-$3\times10^9$ pfu, diluted into 100 μL per injection. Following IC or IV injections, mice were monitored daily for signs of distress including weight loss, piloerection, hind-limb paralysis and respiratory distress. The median lethal dose (LD50) was calculated using the Spearman Karber method, while the maximal tolerable dose (MTD) was denoted as the highest dose not resulting in a single animal death.

Imaging glioblastoma in an animal model: U87MG and CT2A cells were adapted for bioluminescent imaging by transducing with lentivirus containing firefly luciferase (FLUC) and transfecting FLUC plasmid respectively. U87MG FLUC and CT2A FLUC cells were injected IC into CD1 nude and C57BL/6 respectively. Animals with FLUC expressing tumours were monitored for tumour progression using the live imaging IVIS Xenogen 200 system after an IP injection of luciferin (Gold Biotechnology Inc). The animals were monitored for signs of distress including survival, weight loss, morbidity, piloerection, hind-limb paralysis and respiratory distress.

Mouse syngeneic glioblastoma tumour models: Brain tumours were established by a single stereotactic injection with CT-2A mouse glioma cells into 6-8 week old C57BL/6 animals. Five days post injection. On Day 19 C57BL/6 mice bearing CT-2A tumours were IV treated with 6 doses of FMT ($5\times10^8$ pfu/dose thrice weekly) or injected stereotactically with FMT ($2\times10^7$ in a volume of 50 μl) using an infusion pump (rate=3 μl/min). Some C57BL/6 animals were sacrificed at day 19 and images were captured on a Nikon dissecting microscope. The remaining animals were monitored for survival.

Human glioblastoma xenograft model: Human ovarian U87MG cells were adapted for bioluminescent imaging at which time 1e6 U87MG cells were injected IC into 6-8 week old athymic CD-1 nude mice. Untreated CD-1 animals develop tumours at about day 15-21. Mice were either treated with a single intravenous (tail vein) injection performed on day 14 with FMT ($5\times10^8$), or treated IC with the same viruse at a dose of $2\times10^7$ pfu. Animals were monitored for survival and for signs of distress including weight loss, morbidity, piloerection, hind-limb paralysis and respiratory distress. Tumour imaging was captured with a Xenogen 200 IVIS system (Caliper LS, USA).

Rotorod: Balb/C mice were tested for motor function/performance on a rotating rod apparatus prior to IC viral administration. Mice were placed on a rotorod for 3 trials per day for 4 consecutive days. After allowing the animals 0.5 min to adjust to the apparatus, the rod was accelerated in a linear fashion 0.1 rpm/s. Latency to fall was measured in minutes. The animals were divided into groups of 3. Motor function one week post surgery in uninjected (Naïve), PBS and FMT IC treated animals. Standard error of the mean was calculated.

Nucleic Acid Sequencing: FMT sequencing was performed at the Ontario Institute for Cancer research (Toronto, Canada) on FMT cDNA which was generated using a shotgun approach with random hexamers on trizol extracted and RNeasy purified FMT RNA.

Protein sequencing: FMT virus was amplified in Vero cells to high titer (~$10^{11}$ pfu/mL), purified, and lysed with 5× Laemmli sample buffer (60 mM Tris-Cl pH 6.8, 2% SDS, 10% glycerol, 5% β-mercaptoethanol, 0.01% bromophenol blue) and separated on 12% SDS-PAGE gels. Replicate gels were stained with either coomasie blue or silver, and nine bands were extracted for peptide sequencing.

Manufacturing and rescuing recombinant FMT virus: Recombinant FMT was produced as described recently for Maraba virus25. Briefly, FMT virus complementary DNA (cDNA) was amplified in three separate RT-PCR reactions yielding overlapping fragments that were stitched together using internal restriction sites. The full length ~11 Kb cDNA was then cloned into a modified LC-KAN vector (Lucigen, Middleton, Wis.) carrying a T7 promoter upstream of the 5'-antigenomic leader sequence and immediately downstream of the 3'-terminator a modified hepatitis delta virus ribozyme and T7 polymerase termination signal sequence. A549 lung carcinoma cells seeded at $3.0\times10^5$ cells/well in 6-well plates were infected 24 hr later with vaccinia virus (moi=10) expressing the T7 RNA polymerase37 in OptiMeM medium for 1.5 hours. Following removal of the vaccinia virus, each well was transfected with LC-KAN FMT (2 μg) together with pCl-Neo constructs encoding for FMT "N" (1

μg), "P" (1.25 μg), and L (0.25 μg) with lipofectamine 2000 (5 μl per well) according to the manufacturer's instructions. The transfection reagent was removed 5 hr later and replaced with DMEM containing 10% HI-FBS. At 48 hours following the transfection, medium was collected (pooled from two plates), filtered (0.2 μm) to remove contaminating vaccinia virus, and 1 ml was used to infect SNB19 glioblastoma cells in each well of a 6-well plate. Cytopathic effects and GFP expression visible 24-48 hours later were indicative of a successful rescue. Recombinant FMT underwent three rounds of plaque purification (on SNB19 cells), before scale up, purification on sucrose cushion, and resuspension in PBS containing 15% glucose.

Phylogenetic Analysis: Phylogenetic relationships between rhabdoviruses based on a Muscle alignment of L protein amino acid sequences, and using the paramyxovirus Measles Edmonston strain as the outgroup. The tree was generated by the neighbor-joining method and bootstrap values (indicated for each branch node) were estimated using 1000 tree replicas. Branch lengths are proportional to genetic distances. The scale bar corresponds to substitutions per amino acid site.

Immunoblotting: Cells were lysed (50 mM Tris-HCl; 150 mM NaCl; 1% Triton X-100; 1% SDS) and protein quantified using the Lowry assay (Bio-Rad). Total cell lysates were prepared in SDS sample buffer, and 5-50 μg of total protein was separated by SDS-PAGE on Bis-Tris gels (ranging from 8-15%) and transferred to nitrocellulose or PVDF membranes. Membranes were probed with primary antibodies diluted in 5% skim milk powder (SMP) or 5% Bovine Serum Albumen (BSA) overnight at 4 deg C, followed by horse radish peroxidase-conjugated secondary antibodies diluted in 5% SMP for 1 hr at room temperature. The following primary antibodies were used: rabbit anti-PARP (Cell Signaling, 9542); mouse anti-caspase 3 (Cell Signaling, 9668); mouse anti-caspase 8 (Enzo Life Sciences, 12F5); rabbit anti-caspase 9 (Cell Signaling, 9502); rabbit anti-BID (Cell Signaling, 2002); mouse anti-GAPDH (R&D Systems). A polylonal anti-FMT antibody was generated in rabbits (Capralogics Inc.) using purified, UV-inactivated FMT virus. Protein bands were visualized using SuperSignal West Pico Chemiluminescent Substrate System (Pierce Biotechnology)

CD8+ T cell depletion: The brains of 7 week old C57BL/6 mice were stereotactically implanted with 2e5 CT2A cells that express firefly luciferase (CT2Afluc). Mice were treated with 2e7 PFU of Farmington virus at the site of tumour implantation 7 days later. For CD8+ T cell depletion studies, 200 μg of anti-mouse CD8 antibody (clone 2.43) was injected intraperitoneally (IP) one day prior to virus treatment and 100 μg on the day of treatment. A maintenance dose of 100 μg every 3 days was given for the following 2 weeks.

Statistics: For Kaplan Meier plots, survival plots were compared using Mantel-Cox Log rank analysis (Graphpad Prism).

EXAMPLES

Example 1

Farmington Virus is not a Vesiculovirus

Figure 1F:
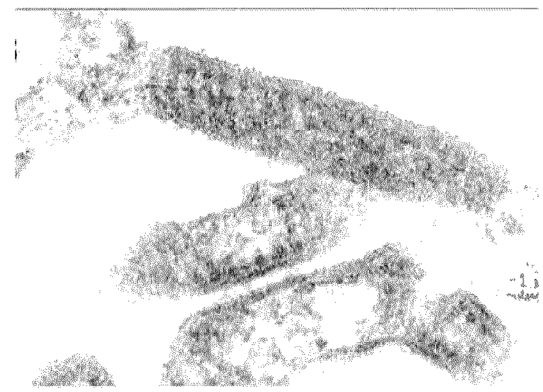

The full-length genomic sequence for FMT was determined. The sequence of the complementary DNA (cDNA) polynucleotide produced by FMT is shown in SEQ ID NO: 1. The RNA polynucleotide of FMT is shown in SEQ ID NO: 2. Five putative open reading frames were identified in the genomic sequence. Additional ORFs may be present in the virus that have not yet been identified. The sequences of the corresponding proteins are shown in SEQ ID NOs: 3, 4, 5, 6 and 7, and the encoding DNA sequences are shown in SEQ ID NOs: 8, 9, 10, 11 and 12, respectively. Phylogenetic analysis of the full-length genomic sequence was performed by aligning the amino acid sequence of the putative FMT L protein to the L protein sequences of representative members from the 6 genera of Rhabdoviridae (FIG. 1). The alignment demonstrated that FMT did not appear to belong to the current 6 genera schema of the Rhabdoviridae family. FMT virus appears to be more divergent from the currently known rhabdoviruses. While we did detect some sequence homology (~50% identity) between a short segment of the L protein of FMT and lettuce necrosis yellow virus, we were unable to detect any homology of the 4 remaining FMT putative open reading frames (ORFs) (N, P, G, M) to any sequences in the NCBI database. This suggests that FMT, which was originally classified incorrectly as a vesiculovirus (Tesh et al. Emerging Infect. Dis. 2002), may in fact constitute the type member of a new genus within the Rhabdoviridae family (FIG. 1; and see Table 2 and accompanying Sequence Listing file).

TABLE 2

Description of Sequences.

| | | |
|---|---|---|
| SEQ ID NO. 1 | Farmington rhabdovirus-DNA | cDNA produced by the FMT rhabdovirus |
| SEQ ID NO. 2 | Farmington rhabdovirus-RNA | |
| SEQ ID NO. 3 | Farmington rhabdovirus ORF 1 | The promoter is at position 134 to 149 and the encoding sequence is at positions 206 to 1444 of SEQ ID NO: 1 |
| SEQ ID NO. 4 | Farmington rhabdovirus ORF 2 | The promoter is at position 1562 to 1578 and the encoding sequence is at positions 1640 to 2590 of SEQ ID NO: 1 |
| SEQ ID NO. 5 | Farmington rhabdovirus ORF 3 | The promoter is at positions 2799 to 2813 and the encoding sequence is at positions 2894 to 3340 of SEQ ID NO: 1 |
| SEQ ID NO. 6 | Farmington rhabdovirus ORF 4 | The promoter is at positions 3457 to 3469 and the encoding sequence is at positions 3603 to 5717 of SEQ ID NO: 1 |
| SEQ ID NO. 7 | Farmington rhabdovirus ORF 5 | The promoter is at positions 5766 to 5780 and the encoding sequence is at positions 5832 to 12221 of SEQ ID NO: 1 |

SEQ ID NO: 3 is encoded by SEQ ID NO: 8 (i.e. the encoding sequence of positions 206 to 1444 of SEQ ID NO: 1). SEQ ID NO: 4 is encoded by SEQ ID NO: 9 (i.e. the encoding sequence of positions 1640 to 2590 of SEQ ID NO: 1). SEQ ID NO: 5 is encoded by SEQ ID NO: 10 (i.e. the encoding sequence of positions 2894 to 3340 of SEQ ID NO: 1). SEQ ID NO: 6 is encoded by SEQ ID NO: 11 (i.e. the encoding sequence of positions 3603 to 5717 of SEQ ID NO: 1). SEQ ID NO: 7 is encoded by SEQ ID NO: 12 (i.e. the encoding sequence of positions 5832 to 12221 of SEQ ID NO: 1).

FIG. 1 shows A) Schematic of where FMT was first isolated in 1969. B) Amino acid Blast alignment of 5 FMT ORFs reveals no sequence homology to any other sequences in the database except for the L protein which is ~45% similar to plant rhabdovirus: Lettuce Necrotic yellow virus (LNYV). C) Commassie stained SDS PAGE gel of FMT virus showing 4 of the 5 predicted FMT ORF proteins. These bands were excised from the gel and their identity confirmed through protein sequencing by tandem mass spectrometry. D) Phylogenic tree derived from the amino acid sequences of the polymerase genes of various rhabdoviruses. The Measles paramyxovirus was included as a non-family control. All previous oncolytic rhabdoviruses have been identified from the vesiculovirus genus (VSV, Maraba). Unexpectedly, Farmington virus appears to cluster with the plant infecting cytorhabdoviruses. E) We have built a recombinant system for the FMT platform that allows us complete control of the genetic make-up of the virus. We show here the generation of a fully replicative GFP expressing FMT strain as an example. F) Electron microgram of FMT bullet shaped virion measuring 55 nm×150 nm. (adapted from Tesh et al. Emerging Infect. Dis. 2002).

Example 2

Farmington Virus does not Demonstrate Neurotoxicity

FMT demonstrated profound attenuation in non-transformed cells in vitro. To ascertain whether the observed attenuation in vitro translates to safety in vivo, we injected stereotaxically into the right striatum of the brain increasing doses of rhabdoviruses and monitored for signs of neurotoxicity (including weight loss, piloerection, hind leg paralysis, morbidity and mortality). FMT had an $LD_{50}$ of approximately $1\times10^9$ in contrast the other rhabdoviruses displayed $LD_{50}$ of approximately $10^2$. (FIG. 2A). The Maximum Tolerated Dose (MTD) was determined to be the highest dose not resulting in durable morbidity. (FIG. 2A). For FMT the MTD was approximately $1\times10^{7.5}$ pfu while for the other rhabdoviruses the $LD_{50}$ occurred at such a low dose of virus the MTD was impossible to determine. These animals displayed clinical signs of a CNS infection with rapid and progressive weight loss, hind leg paralysis and had significant titres of virus in their brain just prior to death (data not shown).

Although we found no acute neurotoxicity from IC treatment with FMT, we wished to assess the cognitive and motor function of the mice several days after virus infection. Therefore, we assessed the motor function before and after treatment with these wild-type FMT virus using a rotorod apparatus (FIG. 2B). Specifically, we measured the latency of these animals to fall from a slowly accelerating rod. We show that there is no significant difference in the latency to fall between the mock-infected animals or virus infected animals, 1 week prior and 1 week post injection (FIG. 2B).

Figures 2C, 2D:
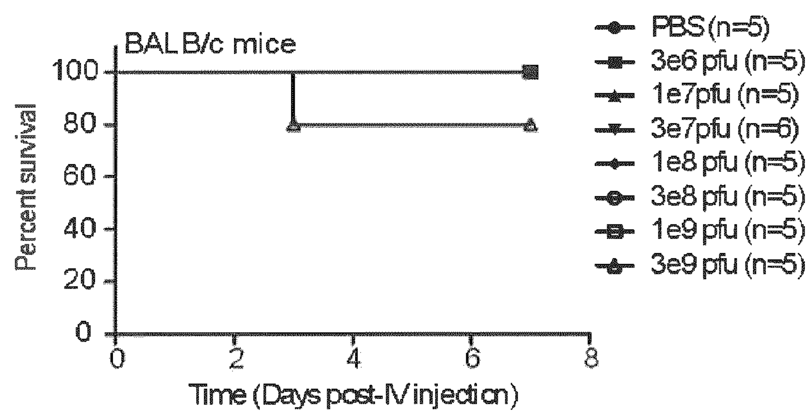
FIG. 2. FMT Safety Profile: A) Intracranial neurotoxicity screen for rhabdoviruses; B) Motor function assessment by time on rotorod after intracerebral injection of FMT in Balb/C mice; C) FMT MTD determination in Balb/C mice injected IV with increasing doses (3xe6 pfu-3e9 pfu) of FMT virus; D) Detection of viable FMT virus 3 months post-inoculation; E) Histopathology of Brain following intracerebral inoculation with FMT, VSV or PBS.
Figure 2E:
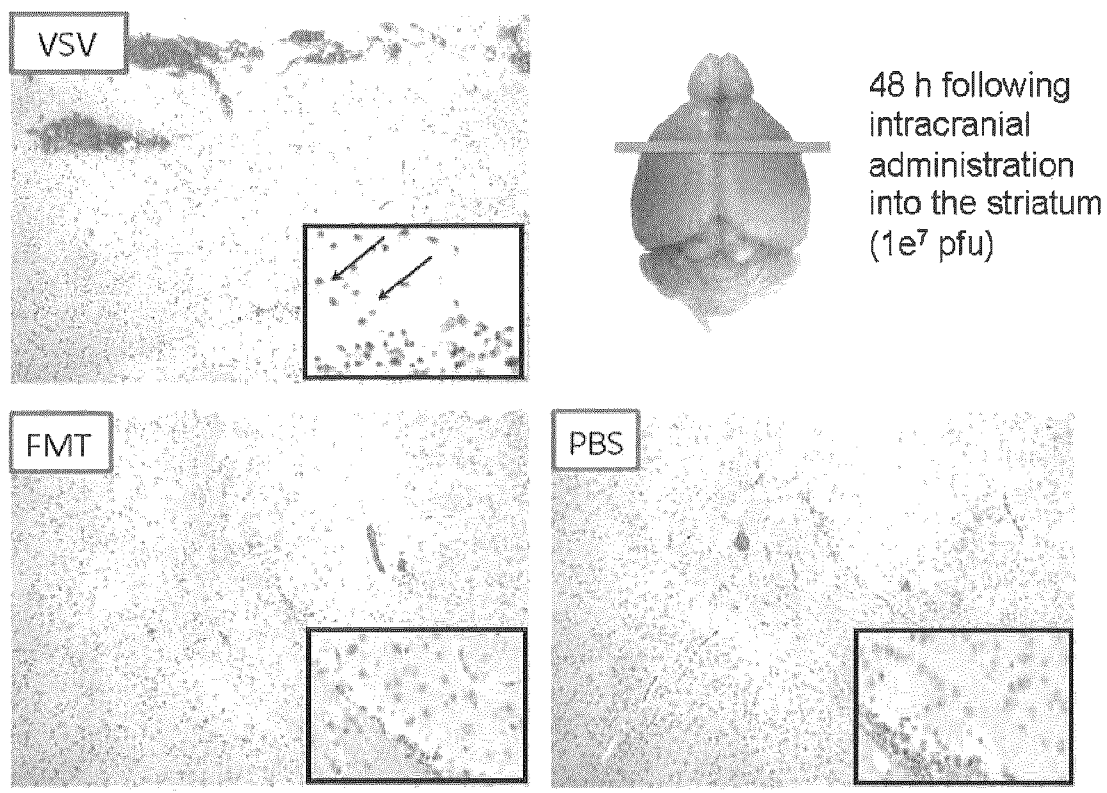

In addition to intracranial toxicity, we evaluated the toxicity of FMT when administered intravenously (IV) in immunocompetent mice with escalating doses of virus (FIG. 2C). FMT is well tolerated IV and never reaches an $LD_{50}$ even at our highest dose $3\times10^9$ pfu which is comparable to an attenuated version of Maraba we described in Brun, J. et al. Identification of Genetically Modified Maraba Virus as an Oncolytic Rhabdovirus. Mol Ther 18, 1440 (2010). FMT animals IV dosed at greater than $3\times10^8$ pfu displayed transient weight loss and moderate piloerection, which resolved 5-7 days post treatment (data not shown). No detectable titres were observed from brain homogenates taken from FMT treated animals 3 months post IV treatment (FIG. 2D). In addition, following administration of high doses of FMT ($1\times10^7$ pfu) in the brain, we found no signs of cell death and comparable inflammatory responses to those of saline injected control mice (FIG. 2E). This differed dramatically from VSV injected animals, which displayed a striking increase in inflammatory cells, condensed nuclei, and a perforated morphology. Due to its lack of neurotoxicity and potent CNS tumour killing capacity, we elected to proceed with FMT as a platform to develop as a novel oncolytic against GBM.

FIG. 2 shows the FMT Safety Profile A) Groups of 5 Balb/C mice were injected sterotaxically into the right striatum of the brain with increasing doses of rhabdoviruses as indicated and monitored for signs of distress including weight loss, piloerection, hind leg paralysis, morbidity and mortality. Maximal Tolerable Dose (MTD) was determined to be the highest dose not resulting in durable morbidity as measured by behaviour and weight. $LD_{50}$ was determined using the Spearman Karber method. FMT is unique among rhabdoviruses as a non-neurotoxic virus. B) To detect any cognitive deficiencies in the striatum, motor function was assessed by rotorod apparatus which measures latency to fall off an accelerating rod. Motor function is indistinguishable from controls after intracerebral injection of FMT. C) Groups of 3-5 Balb/C mice were injected once intravenously in half log increments of virus ranging from $3\times10^6$ pfu to $3\times10^9$ pfu. The animals were monitored for signs of distress including weight loss, morbidity, piloerection, hind-limb paralysis and respiratory distress. FMT shows a very high MTD of $1\times10^9$ pfu when delivered systemically. D) Animals sacrificed 3 months post-intracerebral inoculation demonstrate no viable virus in the brain homogenates. Limit of detection is 101. E) Balb/C mice were inoculated intracerebrally with the indicated viruses ($1\times10^7$ pfu) and sacrificed 2 days post treatment. Little to no inflammation is visible and no cell loss is detectable following FMT treatment. This is in contrast to VSV which shows significant neuronal loss (empty spaces, inset).

Example 3

Farmington Virus Potently and Selectivity Kills Brain Tumour Cells

Figure 3B:
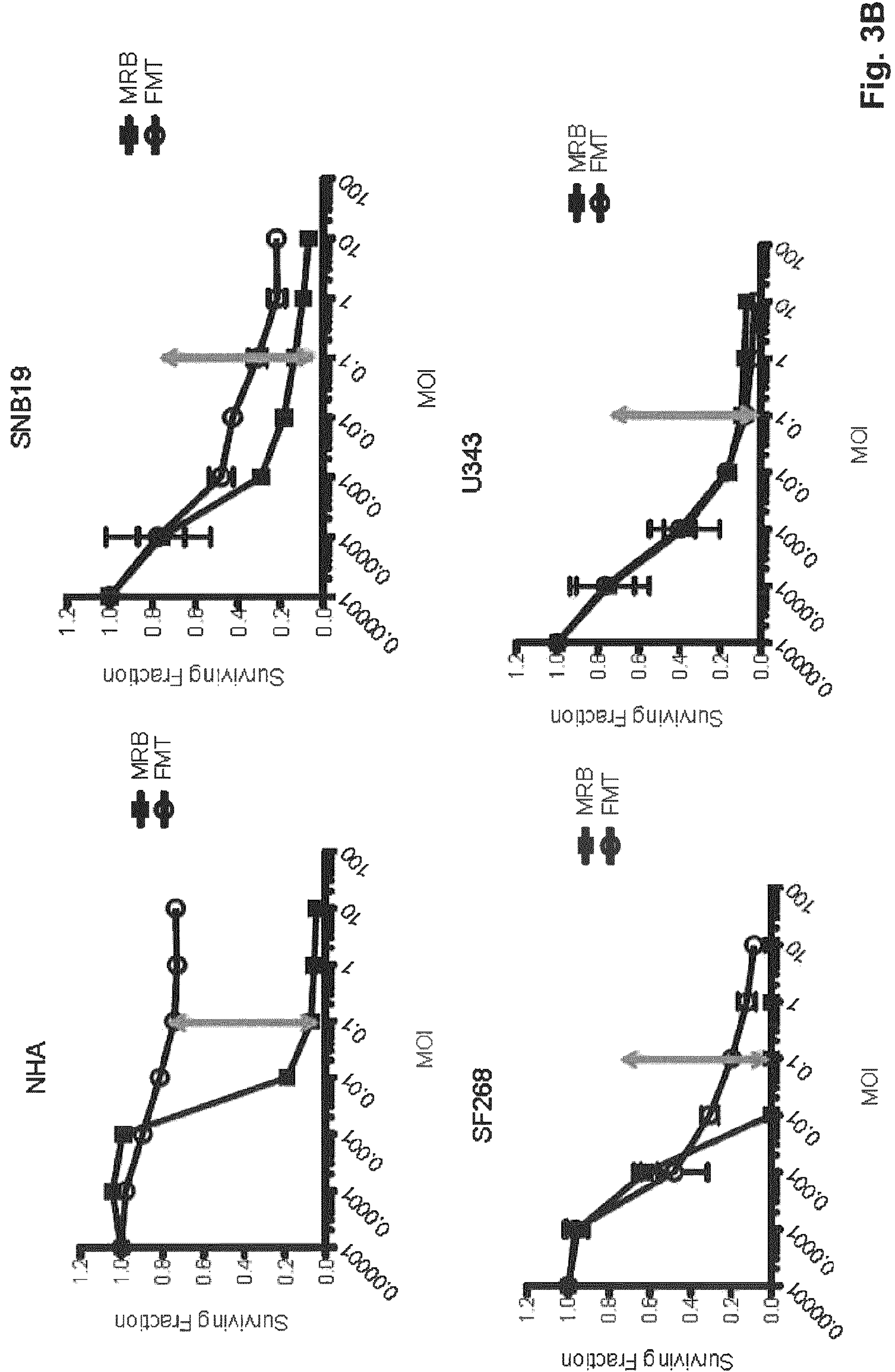
FIG. 3. FMT Potently and Selectively Kills Brain Tumour Cells: A) Summary of FMT virus cytotoxicity in vitro; B) FMT is a potent and selective killer of GBM cell lines; C) Assessment of FMT potency against tumour and normal cells.

Wild-type FMT isolates demonstrate attenuation in normal primary cells while maintaining potent glioma cell killing capacity (FIG. 3A). To evaluate the clinical relevance of our novel oncolytic rhabdoviruses to treat brain cancer, we examined whether FMT could kill freshly derived patient tumour samples. Cell cultures isolated from 3 patients with primary glioblastoma multiforme were infected with FMT and 48 h later, viability assays demonstrated that FMT virus was potently cytotoxic to 2 of 3 patient tumour explants (FIG. 3A). To test the killing capacity of the FMT isolates we performed cell killing assays on normal human astrocytes (NHA) and 3 GBM tumour cell lines (FIG. 3B). While wild type MRB was very potent against all of the GBM cell lines, it was also highly lytic against both primary normal human astrocytes (NHA). Remarkably, FMT demonstrated the greatest therapeutic index, with potency rivaling MRB in the majority of GBM lines while remaining highly attenuated in NHA and GM38 primary cell lines (FIG. 3C). This demonstrates that FMT virus is a potent and selective oncolytic virus when tested against brain cancer cell lines.

In FIG. 3 we show A) Summary of FMT in vitro cytotoxicity showing potent activity against primary glioblastoma patient samples and established human and mouse brain tumour cell lines, while remaining attenuated against normal cells. B) FMT is a potent and selective killer of glioblastoma cell lines. Viability was assayed using Alamar blue assay 72 h post treatment. Error bars represent SEM of 4 biological replicates. C) Detailed assessment of FMT potency against tumour and normal cells. EC50 (moi=multiplicity of infection) represents the the ratio of virus:cell required to kill 50% of cultured cells in a 72 time frame as measured using an Alamar Blue viability assay.

Example 4

Figure 4A:
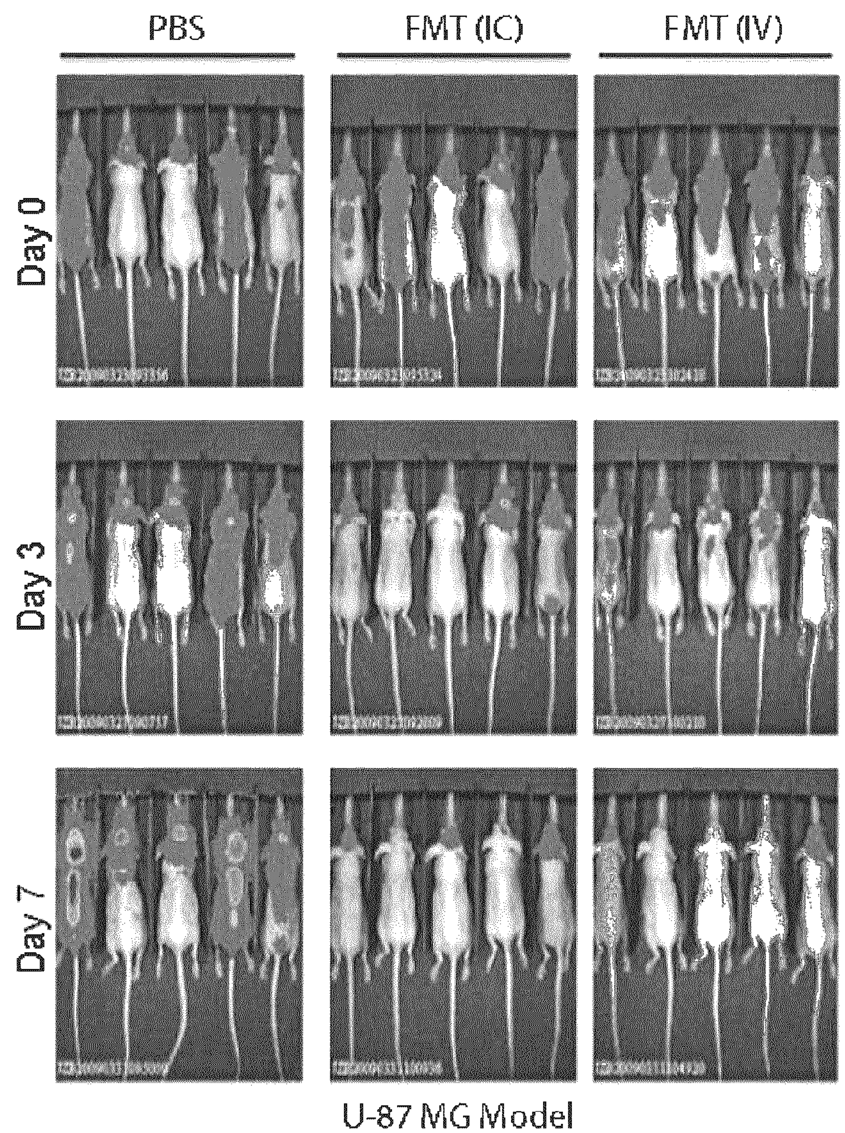
FIG. 4. FMT In Vivo Efficacy in Preclinical Models of GBM: A) U-87 MG Human Glioma Xenograft Model; B) Kaplan Meier survival plot of animals treated with a single dose IC (1e5 pfu) or IV (5e8 pfu); C) Fluorescence micrograph of mock infected mouse brain (with GFP tagged U87MG tumour) versus FMT treated mouse brain; D) Late Syngeneic mouse GBM model using the CT2A cell line treated both IC and IV with FMT or PBS.
Figure 4B:
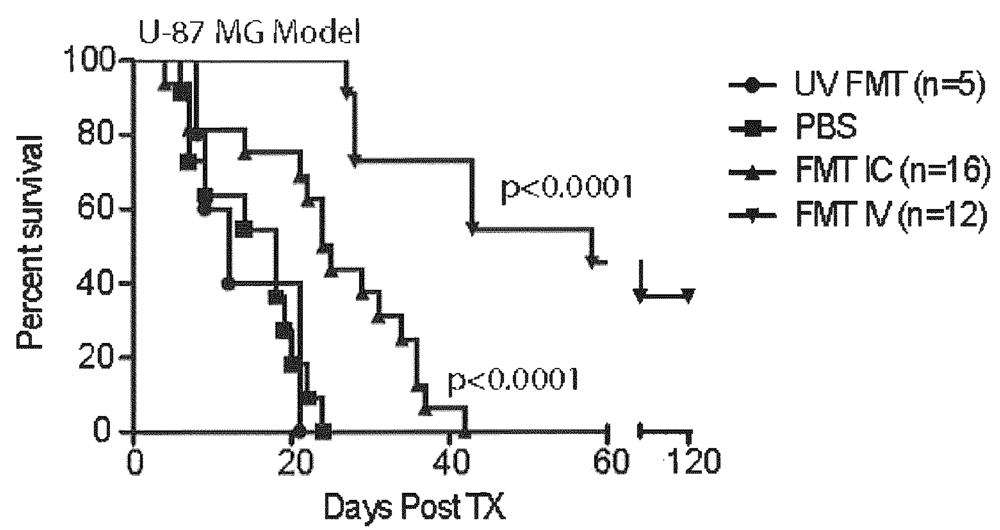
Figure 4C:
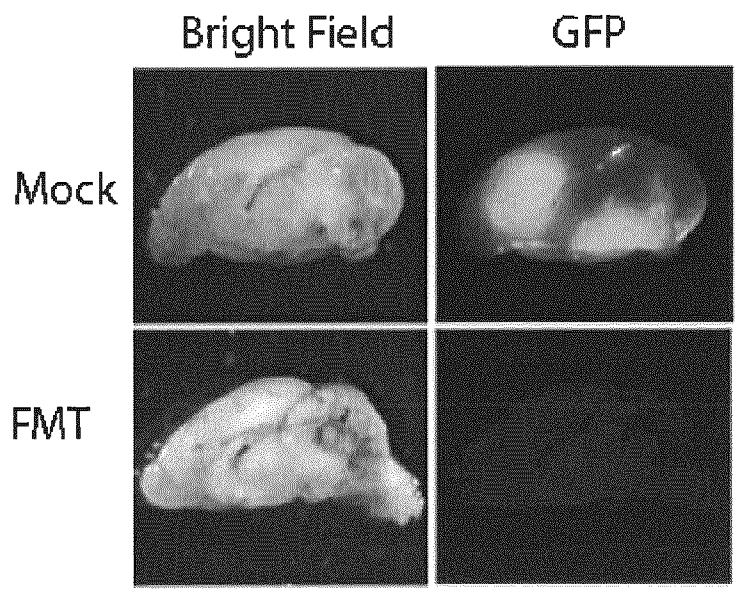
Figure 4D:
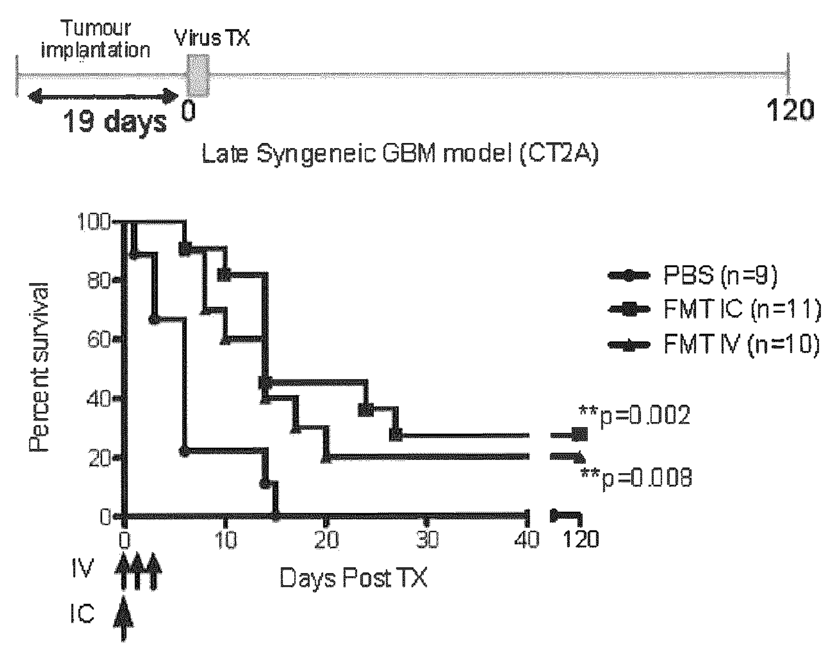

Farmington Virus is Efficacious in Xenograft and Syngeneic Models of Glioblastoma We next sought to determine the in vivo efficacy of our candidate viruses in mouse models of glioblastoma. After adapting human U87MG glioma cells for bioluminescent imaging, we established an intracerebral U87MG glioma model in athymic mice and we examined the IV and IC efficacy of FMT in this model (FIG. 4A-B). Specifically, animals were treated with a single FMT dose IC ($1\times10^5$) or IV ($5\times10^8$ pfu) 14 days post implantation. Three days after the first treatment we observed a significant decrease in tumour burden with a greater decrease observed by day 7 (FIG. 4A). Interestingly the spinal metastases in this model are completely cleared in all tumour bearing animals. In contrast, animals treated with UV inactivated virus had a significant increase in tumour burden by day 7 at which point they started exhibiting neurological symptoms from their brain tumours (FIG. 4B). All IV treated animals responded to treatment with 4 of 11 durably cured and surviving beyond 100 days post treatment. Most IC treated animals responded to treatment (10 of 16) with a significant (~2 fold) increase in time to death. Moreover we also used fluorescent microscopy to visualize tumour explants of mock-infected animals and durably cured animals. While we detect a strong GFP expressing glioma tumour in mock-infected animals, there is a clear absence of GFP signal in FMT treated animals (FIG. 4C). To complement our studies of viral efficacy in immunocompromised animals, we tested FMT in a mouse CT-2A syngeneic glioma model. Unlike xenograft models in which human gliomas grow expansively, CT-2A gliomas are infiltrative similar to what is observed clinically. We established the CT-2A glioma model by stereotactically injecting $2\times10^5$ cells into the striatum (right frontal lobe) of C57BL/6 mice. Since treatments typically commence in human patients after they present with clinical symptoms of GBM, we sought to examine the effect of FMT at exactly the time when animals exhibit outward symptoms. In the CT-2A animals begin to show symptoms 15-20 days post implantation. These symptoms include increased intracranial pressure, lethargy, motor function, piloerection, and hunched posture. Accordingly, 19 days post implantation C57BL/6 animals were treated with FMT IV ($5\times10^8$ pfu thrice weekly for 2 weeks) or with a single IC dose of FMT ($2\times10^7$ pfu). Most animals responded to both the treatment regimens, durable cures achieved in 3 of 11 IC and 2 of 10 IV treated animals in this challenging model of advanced GBM (FIG. 4D). Thus FMT virus demonstrates efficacy in preclinical models of brain cancer.

FIG. 4 shows FMT In Vivo Efficacy in Preclinical Models of Glioblastoma A) Bioluminescence-adapted U87MG human gliomblatsoma cells (1e6) were stereotxically implanted into right striatum of CD-1 nude mice. After 2 weeks animals were either treated with a single dose of FMT intravenously (IV—$5\times10^8$ pfu) or intracranially (IC—$1\times10^5$ pfu) and monitored by IVIS bioluminescence imaging. Disseminated tumours in all mice treated with FMT regress rapidly within 3-7 days and become undetectable in the spinal cord. B) Kaplan Meir survival plot of animals treated with a single dose IC ($1\times10^5$ pfu) resulting in a doubling of mean time to death (Log rank test p=0.0001) or IV ($5\times10^8$ pfu) resulting in durable cures in 40% of animals (Log rank test p=0.0001). C) Fluorescence micrograph of a mock infected mouse brain with an orthotopic GFP tagged U87MG tumour (top 2 panels) versus a FMT treated brain (bottom 2 panels). GFP expressing tumour is clearly visible in sagittal sections of untreated mice, while FMT treatment results in no detectable GFP tumour signal, confirming tumour regression. D) Syngeneic mouse glioblastoma tumour model using the CT2A cell line. Here again, tumours were allowed to establish until the point where mice began to die from their tumour burden. Both IC (one dose $2\times10^7$ pfu) and IV (6 doses $5\times10^8$) treatment doubled mean time to death and resulted in >20% durable cures.

Example 5

Farmington Virus Induces Anti-Tumour Immunity

Emerging evidence is demonstrating that the oncolytic effect of many viruses, including oncolytic rhabdoviruses, is due in part to the induction of anti-tumor immunity. To explore the possibility that FMT virus induces multiple mechanisms for tumor destruction in vivo, we asked whether treating immunocompetent tumor-bearing mice with FMT virus evokes anti-tumor immunity. To begin, we performed a "re-challenge" experiment, where C57/BL6 mice previously harboring CT-2A tumors that had been successfully treated with IC FMT virus infusions were injected for a second time with CT-2A cells directly into the brain. In these experiments, previously cured mice uniformly rejected the cells (FIG. 5A), demonstrating that they had acquired long-lasting immunity towards CT-2A antigen(s). Next, we examined the role of cytotoxic T-lymphocytes (CTLs) in the anti-tumor response elicited by FMT virus. Mice were inoculated with CT-2A cells in their brain, and then CTLs were removed using antibodies directed towards CD8 concomitant with FMT virus treatment. Consistent with recent data from other labs using different oncolytic agents, these experiments showed that FMT virus induced complete responses only when CTLs were present (FIG. 5B). Thus, in addition to directly lysing MG cells, these data demonstrate that FMT virus induces a potent and long-lasting CTL-mediated anti-MG immune response in immunocompetent mice.

Figure 5A:
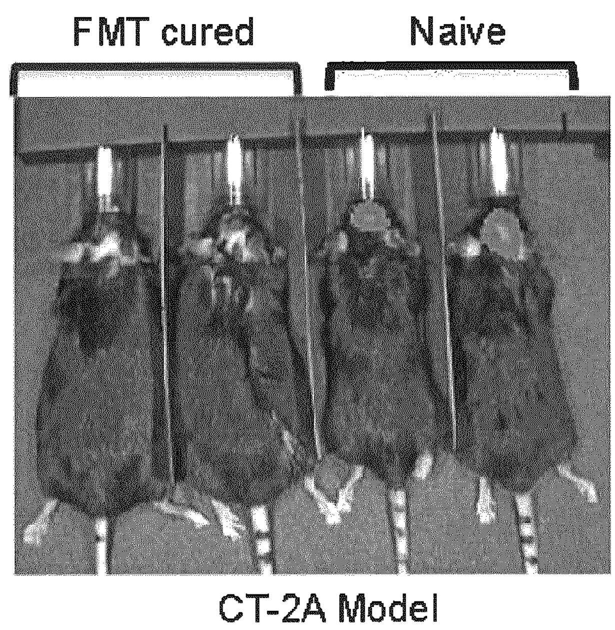
FIG. 5. FMT Virus Induces Anti-Tumour Immunity: A) C57/B6 mice implanted with CT2A murine glioma cells into the striatum and treated with FMT and cured of initial tumour then challenged with CT2A cells implanted into the striatum versus Naive mice implanted with CT2A cells as a control; B) C57/B6 mice implanted with CT2A murine glioma cells into the striatum and allowed to grow tumours received either anti-CD8 polyclonal serum injections to remove CD8+ T cells or matched pre-immune serum as a control then both groups were treated with a single intracranial dose of FMT to induce tumour regressions.
Figure 5B:
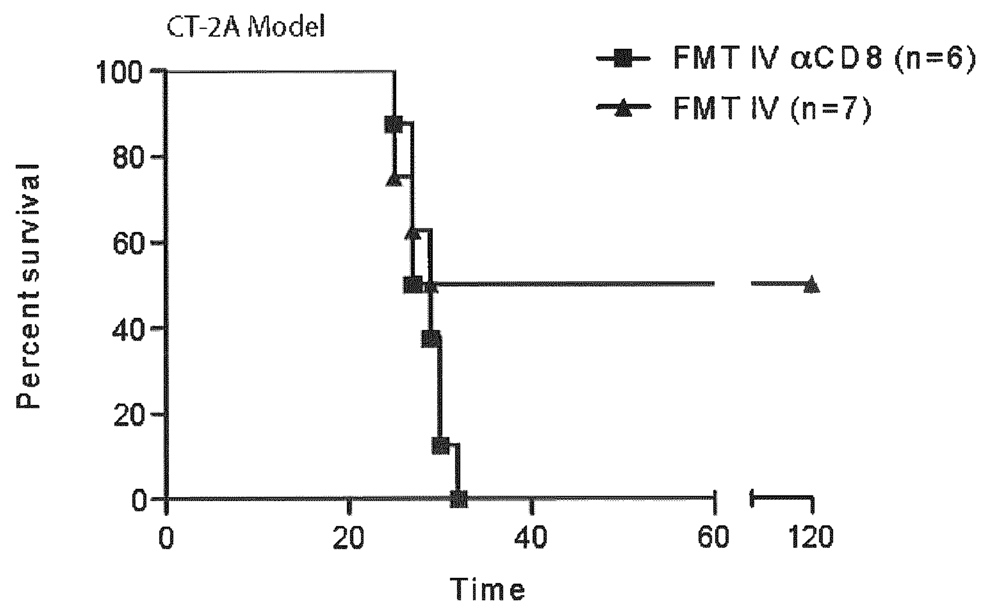

In FIG. 5A, C57/B6 mice were implanted with CT2A murine glioma cells into the striatum ($3\times10^5$ cells). Mice were treated with a single dose of FMT ($2\times10^7$ pfu) and subsequently cured of their initial tumour. After 6 months, these mice were challenged with CT2A cells implanted into the striatum. Naive mice were implanted with CT2A cells as a control. Bioluminescent imaging to monitor CT2A tumour growth showed that mice that had previously been cured of the tumours completely rejected subsequent CT2A tumour growth, while naive mice grew tumours with the expected kinetics. In FIG. 5B) C57/B6 mice were implanted with CT2A murine glioma cells into the striatum ($3\times10^5$ cells) and allowed to grow tumours for 14 days. One group mice received anti-CD8 polyclonal serum injections to remove CD8+ T cells or matched pre-immune serum as a control. Both groups were treated with a single intracranial dose of FMT ($2\times10^7$ pfu) to induce tumour regressions. All mice responded with tumour regression as measured using bioluminescent tumour imaging (not shown), but mice that had been stripped of their CD8+ T cells all eventually regrew tumours and failed therapy.

Example 6

Farmington Virus Productively Infects Tumor and Normal Cells

Figure 6A:
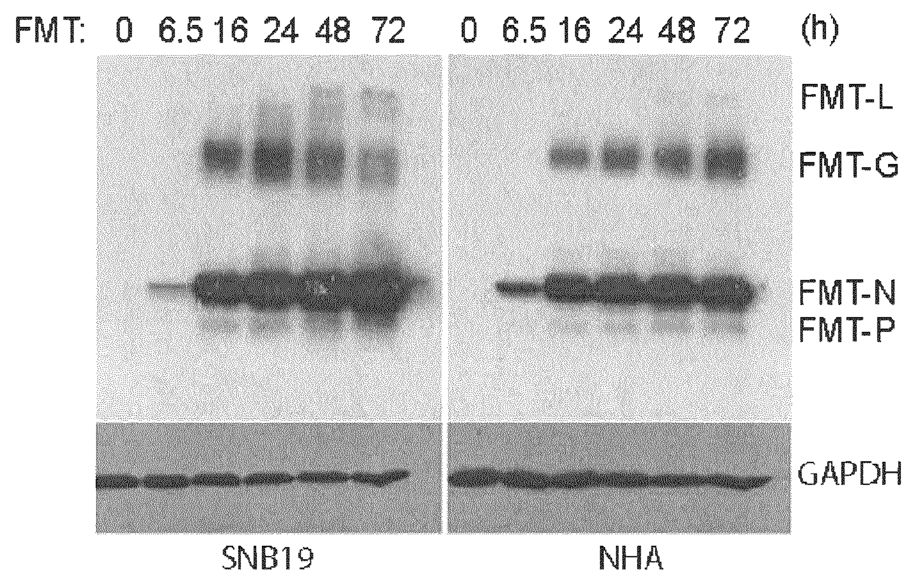
FIG. 6. FMT virus block IFN production and productively infect tumor and normal cells: A) Western blot of human brain tumour cells (SNB19) and primary normal human astrocytes (NHA) showing FMT virus infection and protein production; B) Growth curve of FMT virus production in SNB19 and NHA cells; C) Fluorescence Microscopy of GFP-expressing rec-FMT or Maraba-Δ51 virus added to a GM38 cell monolayer with and without treatment with the type I interferon inhibitor B18R protein derived from vaccinnia virus (VV-B18R); D) Plaque and infectious foci size measured from fluorescence microscopy; E) Interferon bioassay in PC3 cells.
Figure 6B:
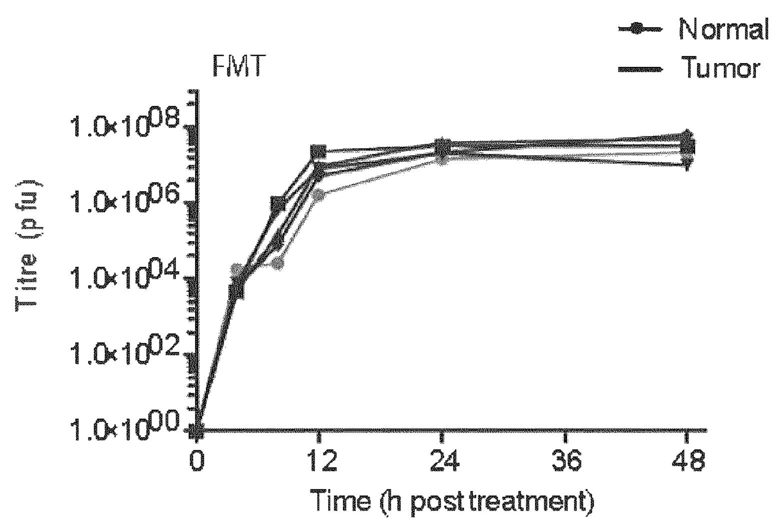

Without exception, the therapeutic index associated with existing oncolytic viruses is due to differential infection and/or productivity in tumor versus normal cells. In the case of rhabdoviruses, current oncolytic strains can "sense" cancer-specific defects in type I IFN signalling, which renders them selectively productive in transformed cells. Unfortunately, current oncolytic rhabdoviruses are highly neurotoxic when delivered local-regionally into the CNS. Given that FMT virus is safe when infused IC and is genetically very distinct from the existing agents, we suspected that its mechanism for tumor-specific destruction must be something other than heightened productivity secondary to IFN defects in tumor cells. To begin to evaluate this hypothesis, we infected SNB19 and NHA cells with rec-FMT-GFP virus and evaluated GFP expression and viral protein production over time. Fluorescence microscopy and immunoblot analyses clearly demonstrated that FMT virus does not distinguish tumor from normal via differential infectivity or viral protein production (FIG. 6A-B). Specifically, both GFP and FMT protein expression became easily detectable 6.5-16 hours after infection and continued to be strongly expressed 72 hours later, irrespective of the transformed state of the infected cell line. In parallel, we performed one-step growth evaluation of FMT virus in various tumor and normal cell lines to examine productivity. These experiments showed that infectious FMT virus particles are produced quickly (within 6.5 hours) and to high titers (~$10^8$ pfu) in both tumor and normal cell lines (FIG. 6B). Collectively, these date demonstrate that, in stark contrast to the existing VSV Δ51 and Maraba MG1 series of oncolytic rhabdoviruses, FMT virus is equally productive in normal as compared to tumor cells.

We thus interrogated the interaction between FMT virus and the type I interferon response. GFP-expressing rec-FMT or Maraba-Δ51 virus was added at low moi to a GM38 cell monolayer, and plaque and infectious foci size were measured. As expected, Maraba-Δ51 infection did not infect or kill GM38 cells unless the innate immune response was blocked a priori by treatment with the type I interferon inhibitor B18R protein derived from vaccinnia virus (VV-B18R; FIG. 6C-D). In contrast, FMT virus formed moderately-sized infectious foci in the GM38 cells, but did not kill them, and was unaffected by B18R pre-treatment. Furthermore, unlike Maraba-Δ51, FMT virus completely blocked type I interferon production in PC3 cells as measured in an interferon bioassay (FIG. 6E). Collectively, these results indicate that, in contrast to the current arsenal of genetically engineered oncolytic rhabdoviruses, FMT virus potently blocks the human type I interferon response and can productively infect both normal and tumor cell lines, which points towards a novel cancer-selective mechanism for this oncolytic agent.

In FIG. 6 is shown A) Western blot demonstrating similar kinetics of FMT virus infection and protein production in both human brain tumour cells (SNB19) and primary normal human astrocytes (NHA). B) Single step growth curve showing identical virus replication and virion productivity from tumour (SNB19) and normal (NHA) cells following infection with FMT. C) Fluorescence Microscopy of GFP-expressing rec-FMT or Maraba-Δ51 virus added to a GM38 cell monolayer, and plaque and infectious foci size were measured showing that Maraba-Δ51 infection did not infect or kill GM38 cells unless the innate immune response was blocked by treatment with the type I interferon inhibitor B18R protein derived from vaccinnia virus (VV-B18R) while FMT virus formed infectious foci in GM38 cells and was unaffected by B18R pre-treatment. D) Size of Infectious foci determined from fluorescence microscopy. E) Interferon bioassay in PC3 cells shows that unlike Maraba-Δ51, FMT blocks type I interferon production.

Example 7

Farmington Virus Selectively Induces Apoptosis in Tumor Cells

Figure 7A:
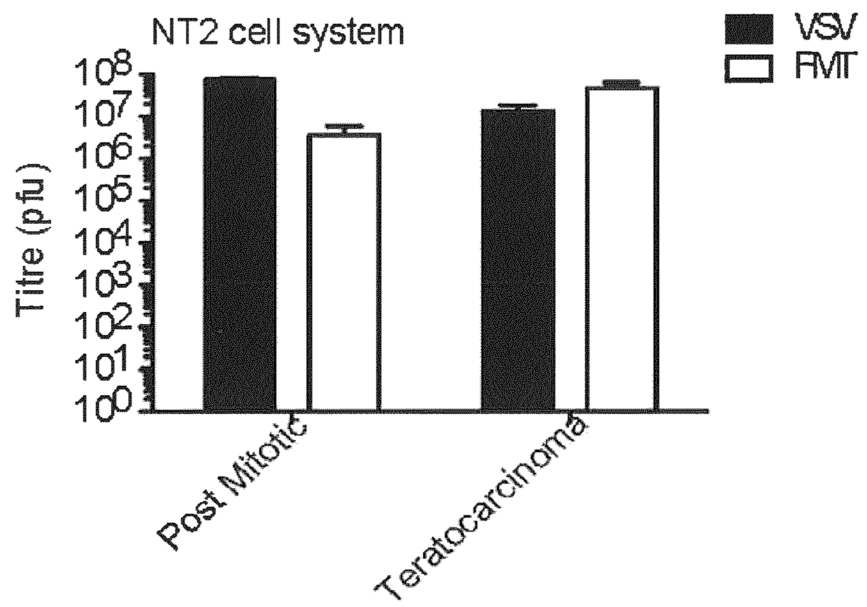
Figure 7B:
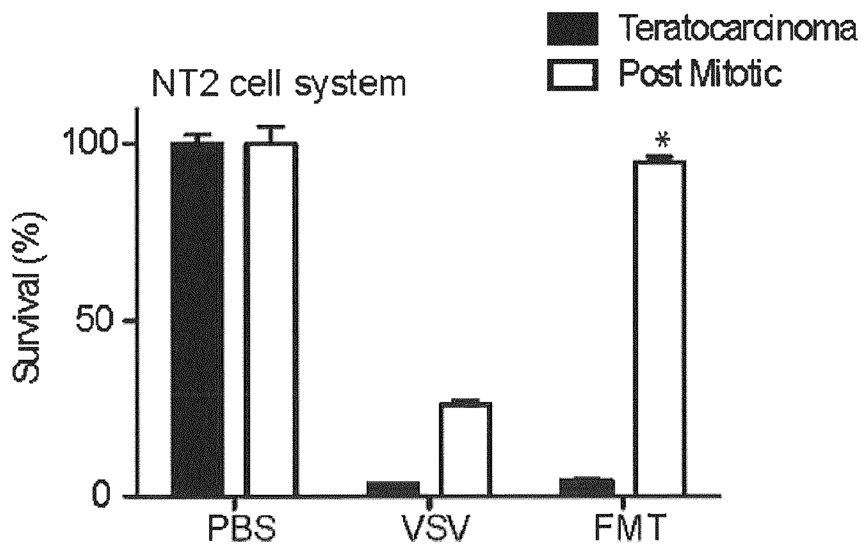
Figure 7C:
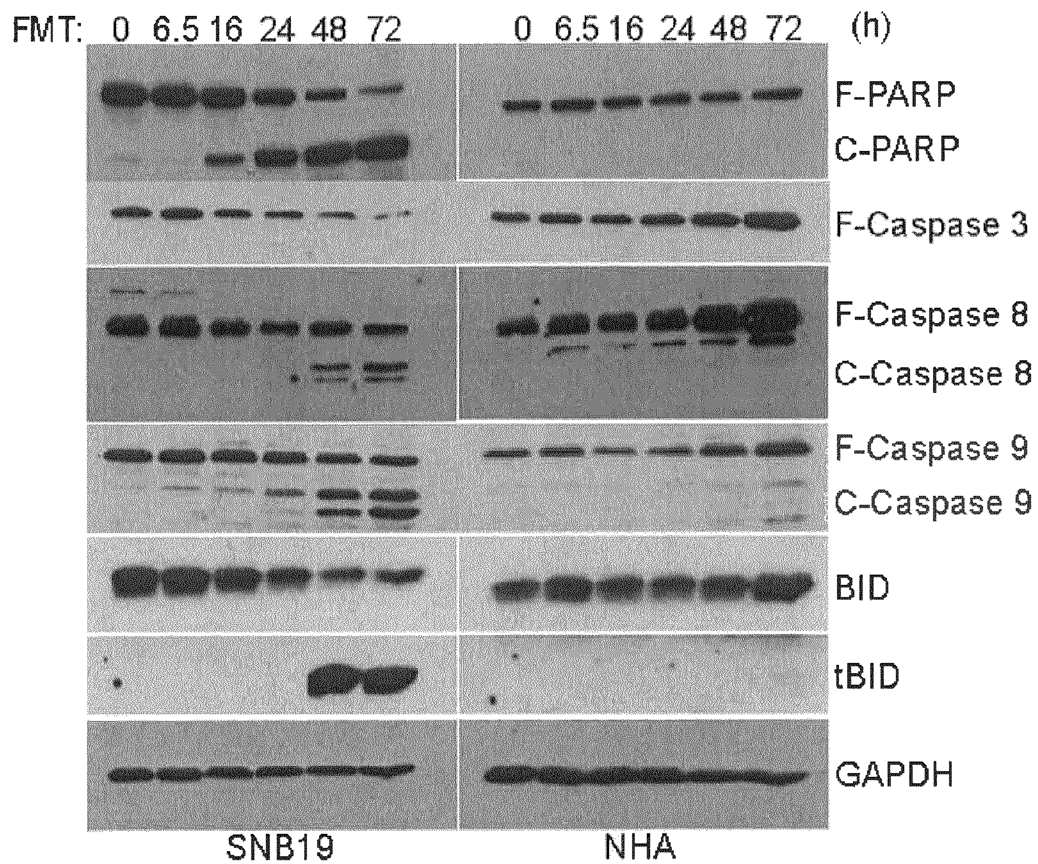
Figure 7D:
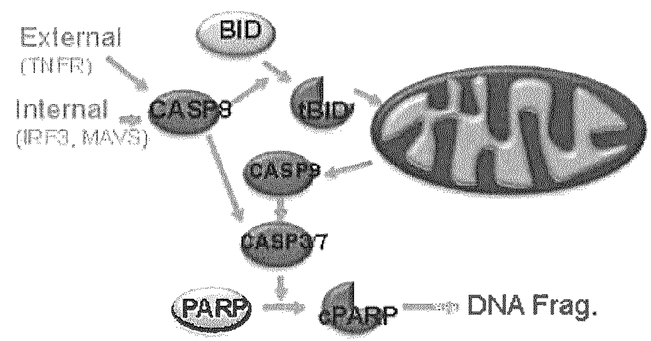

We used the NT2 cell system that consists of transformed NT2 teratocarcinoma cells which can be induced to differentiate into post mitotic neurons with retanoic acid. Following infection with wild type VSV or FMT we observed that these viruses infected and produced infectious progeny to the same degree in either cancerous or non-cancerous forms of the NT2 cells (FIG. 7A). However, although these viruses were potently cytotoxic to malignant NT2 cells, FMT showed almost no cytotoxicity in differentiated post mitotic NT2 cells (FIG. 7B). This indicated that in contrast to other oncolytic rhabdoviruses like VSV, FMT virus appeared to have a unique mechanism of tumour selectivity functioning at the level of cytotoxicity.

Rhabdoviruses kill permissive cells by apoptosis, activated through virus-mediated degradation of key BH3-only proteins, an event which ultimately engages the apical intracellular and extracellular caspases that initiate the irreversible cell death cascade. To ascertain whether FMT virus selectively kills tumor cells via differential induction of apoptosis, we evaluated the activation status of key proteins in the apoptotic heirarchy. As expected, the surrogate apoptosis marker PARP as well as the downstream effector caspase 3 were strongly activated in SNB19 but not NHA cells treated with FMT virus (FIG. 7C), indicating the presence of apoptosis. Moreover, the activator caspases 8 and 9 were engaged in the tumor cells, but not in the normal cells. The NT2 cell system data is consistent with this apoptosis data in the transformed versus normal cell lines showing that cell death induced by FMT virus is dependent not on the productivity of the virus infection within, but rather the anti-apoptotic threshold of, the infected cell.

In FIG. 7A, both pre and post differentiated cell types were permissive to infection by wt VSV and wt FMT virus, producing infectious particles in the $10^6$-$10^8$ range. B) shows that only VSV was cytolytic against the neuron. C) Western blot of several components of the cellular apoptotic signaling cascade following infection of either tumour (SNB19) or normal cells (NHA). FMT appears to initiate the activation (cleavage) of Caspase 8, Caspase 9, BID, and PARP only in tumour cells. To our knowledge, this is the first report of an oncolytic virus whose activity is restricted not at the level of infectivity, but at the level of selective initiation of cell death. D) Schematic of cellular apoptosis signaling cascade. Proteins that are cleaved during activation are depicted in orange and correspond to those included in our western blotting array in panel C.

In the preceding description, for purposes of explanation, numerous details are set forth in order to provide a thorough understanding of the examples. However, it will be apparent to one skilled in the art that these specific details are not required. Equivalent changes, modifications and variations of some examples, materials, compositions and methods can be made within the scope of the present technology, with substantially similar results.

The above-described examples are intended to be exemplary only. Alterations, modifications and variations can be effected to the particular embodiments by those of skill in the art without departing from the scope, which is defined solely by the claims appended hereto.

What is claimed is:

1. A method for inducing an immunogenic response in a patient, the method comprising administering to the patient an isolated viral particle having a genome comprising open reading frames that encode:

a protein comprising SEQ ID NO: 3;

a protein comprising SEQ ID NO: 4;

a protein comprising SEQ ID NO: 5;

a protein comprising SEQ ID NO: 6;

and a protein comprising SEQ ID NO: 7.

2. The method according to claim 1, wherein the isolated viral particle is administered directly to the central nervous system, outside the blood/brain barrier, inside the blood/brain barrier, or any combination thereof.

3. The method according to claim 2, wherein the isolated viral particle is administered to the patient intrathecally, intravenously or via intracranial injection.

4. The method according to claim 1, wherein a cell is infected with the isolated viral particle and the infected cell is administered to the patient.

5. The method according to claim 4, wherein the infected cell is administered directly to the central nervous system, outside the blood/brain barrier, inside the blood/brain barrier, or any combination thereof.

6. The method according to claim 5, wherein the infected cell is administered to the patient intrathecally, intravenously or via intracranial injection.

7. The method according to claim 1, wherein inducing an immunogenic response is against a malignant glioma in the brain of the patient, and wherein the method comprises administration of the isolated viral particle inside the blood/brain barrier.

8. The method according to claim 7, wherein the malignant glioma is a glioblastoma or medulloblastoma.

* * * * *